(12) United States Patent
Schweiger et al.

(10) Patent No.: US 8,202,696 B2
(45) Date of Patent: Jun. 19, 2012

(54) MEANS FOR USE IN TREATING DISEASES CORRELATED WITH OR CAUSED BY NON-PHYSIOLOGICAL LEVELS OF MICROTUBULE-ASSOCIATED PP2AC

(75) Inventors: Susann Schweiger, Berlin (DE); Hans-Hilger Ropers, Berlin (DE); Jennifer Winter, Berlin (DE); Sybille Krauss, Berlin (DE); Vanessa Suckow, Berlin (DE); Rainer Schneider, Wörgl (AT); Alexander Trockenbacher, Innsbruck (AT); John Foerster, Berlin (DE)

(73) Assignee: Max-Planck-Gessellschaft zur Forderung der Wissenschaften E.V., Berlin (DE)

( * ) Notice: Subject to any disclaimer, the term of this patent is extended or adjusted under 35 U.S.C. 154(b) by 436 days.

(21) Appl. No.: 10/514,542

(22) PCT Filed: May 15, 2003

(86) PCT No.: PCT/EP03/05124
§ 371 (c)(1),
(2), (4) Date: May 30, 2006

(87) PCT Pub. No.: WO03/096964
PCT Pub. Date: Nov. 27, 2003

(65) Prior Publication Data
US 2007/0134654 A1 Jun. 14, 2007

Related U.S. Application Data

(60) Provisional application No. 60/380,590, filed on May 15, 2002.

(51) Int. Cl.
*G01N 33/53* (2006.01)
(52) U.S. Cl. ........................................................ 435/7.1
(58) Field of Classification Search .................... 435/7.1
See application file for complete search history.

(56) References Cited

OTHER PUBLICATIONS

Mammalian Target of Rapmycin at http://en.wikipedia.org/wiki/Mammalian_target_of_rapamycin, Jul. 2011.*
Trockenbacher et al., "*MID1*, mutated in opitz syndrome, encodes an ubiquitin ligase that targets phosphatase 2A for degradation", *Nature Genetics*, Nov. 2001; 29(3): 287-294, XP002269767.
Liu et al., "Phosphorylation and microtubule association of the Opitz syndrome protein mid-1 is regulated by protein phosphatase 2A via binding to the regulatory subunit α4", *Proceedings of the National Academy of Sciences of the United States*, Jun. 2001; 98(12): 6650-6655, XP002269768.
Short et al., "MID1 and MID2 homo- and heterodimerise to tether the rapamycin-sensitive PP2A regulatory subunit, Alpha 4, to microtubules: implications for the clinical variability of X-linked Opitz GBBB syndrome and other developmental disorders", *BMC Cell Biology*, Jan. 2002; 3(1): 1-14, XP002269769.
Schweiger et al., "The gene product underlying Opitz Syndrome, MID1, triggers ubiquitin-dependent degradation of phosphatase 2A via binding to its regulatory alpha4 subunit", *European Journal of Human Genetics*, May 2001; 9(Suppl 1): C021, XP009019080.
Everett et al., "Phosphorylation and Microtubule Association of the Opitz Syndrome Protein Midi Is Regulated by Protein Phosphatase 2A via Binding to the Regulatory Subunit of Alpha4", *Circulation*, Oct. 2001; 104(17 Supplement): II.356, XP009025127.
Schweiger et al., "The MIDI/PP2A complex: a key to the pathogenesis of Opitz BBB/G syndrome", *Bioessays*, Apr. 2003; 25(4): 356-366, XP009025013.
Schweiger et al., "The Opitz syndrome gene product, MID1, associates with microtubules", *Proceedings of the National Academy of Sciences of USA*, Mar. 1999; 96(6): 2794-2799, XP002199941.

* cited by examiner

*Primary Examiner* — Karen Carlson
(74) *Attorney, Agent, or Firm* — Pillsbury Winthrop Shaw Pittman LLP

(57) ABSTRACT

The present invention relates to a method of preventing or treating a disease correlated with or caused by non-physiologically increased intracellular levels of the catalytic subunit of microtubule-associated protein phosphatase 2A (PP2Ac) comprising administering to a subject affected by said disease or in danger of developing said disease a pharmaceutically effective amount of a protein selected from the group of MID1 or MID2 or a nucleic acid encoding said protein. The invention further relates to a method of preventing or treating a disease correlated with or caused by non-physiologically decreased intracellular levels of the catalytic subunit of microtubule-associated protein phosphatase 2A (PP2Ac) comprising administering to a subject affected by said disease or in danger of developing said disease a pharmaceutically effective amount of a peptidic fragment of MID1 or MID2 wherein said peptidic fragment comprises amino acids 108-165 (preferably 110-165) of MID1, amino acids 108-165 (preferably 110-165) of MID2 or with an effective amount of a fragment of PP2Ac wherein said fragment comprises the binding site to α4 or of a peptide fragment of α4 comprising amino acids 236-279 or with an effective amount of a nucleic acid molecule encoding said peptide fragment or with an effective amount of a molecule interfering with the interaction of MID1 with α4 or with an effective amount of a molecule interfering with the expression or activity of MID1 and/or α4.

4 Claims, 16 Drawing Sheets

Figure 2:
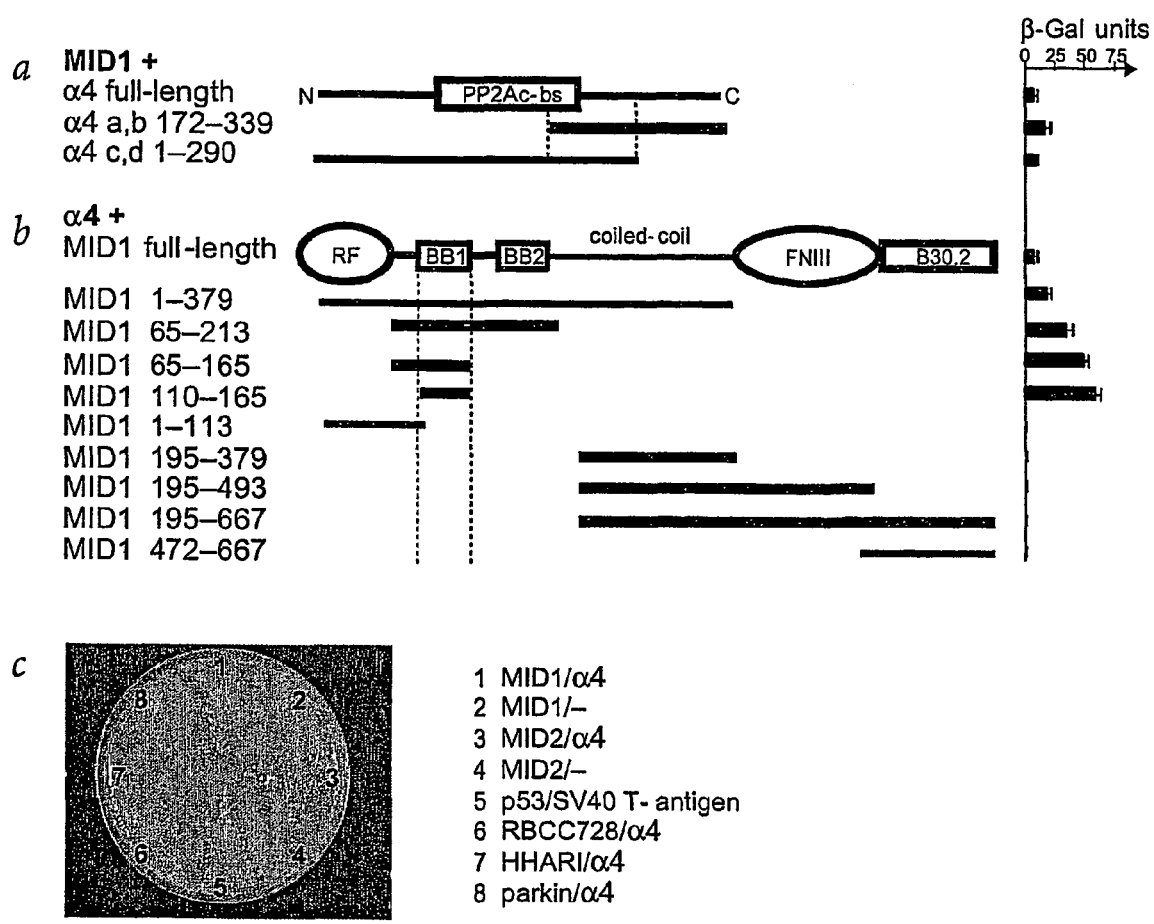

Fig. 1
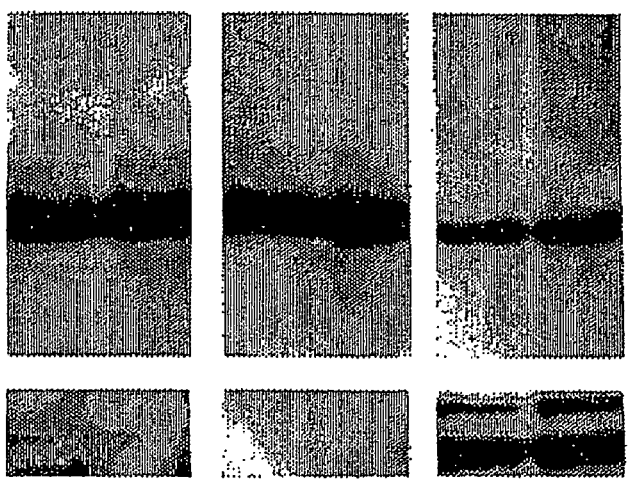
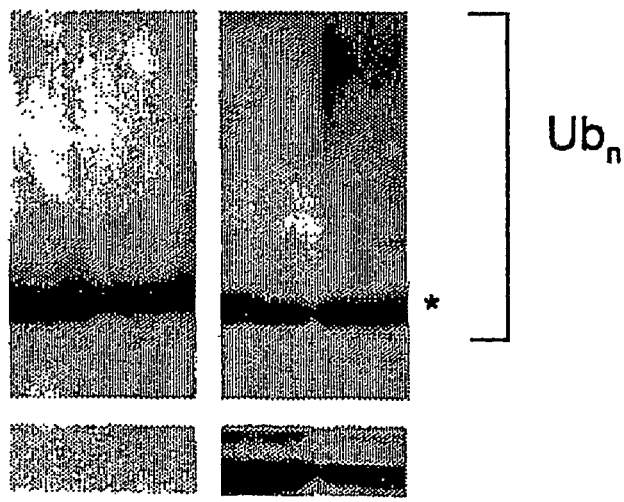

Fig. 9

Tau-1 immunoreactivity (recognizes only dephosphorylated tau):
% average fluorescence in neurons

| analysed cells | mean average % | n |
|---|---|---|
| non-transfected | 100,00 +/-6.15 | 223 |
| Bbox1-transfected* | 158,34 +/-9.40 | 45 |
| Bbox1mut-transfected | 97,39 +/-7.72 | 23 |
| only EGFP-transfected | 98,14 +/-7,5 | 33 | panTau immunoreactivity (recognizes tau phosphorylation-independent)
% average fluorescence in neurons

| analysed cells | mean average % | n |
|---|---|---|
| non-transfected | 100,00 +/-7,9 | 75 |
| Bbox1-transfected | 110,80 +/-11,70 | 12 |
| Bbox1mut-transfected | nd | nd |
| only EGFP transfected | 90,00 +/-5,76 | 34 |

Figure 16
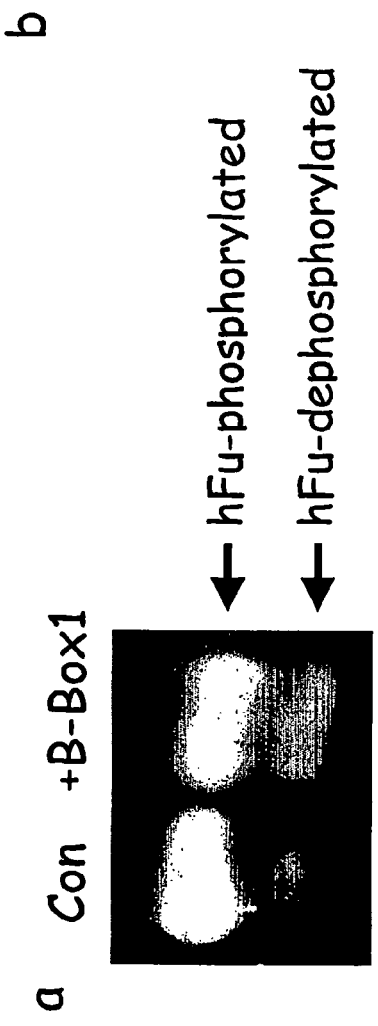
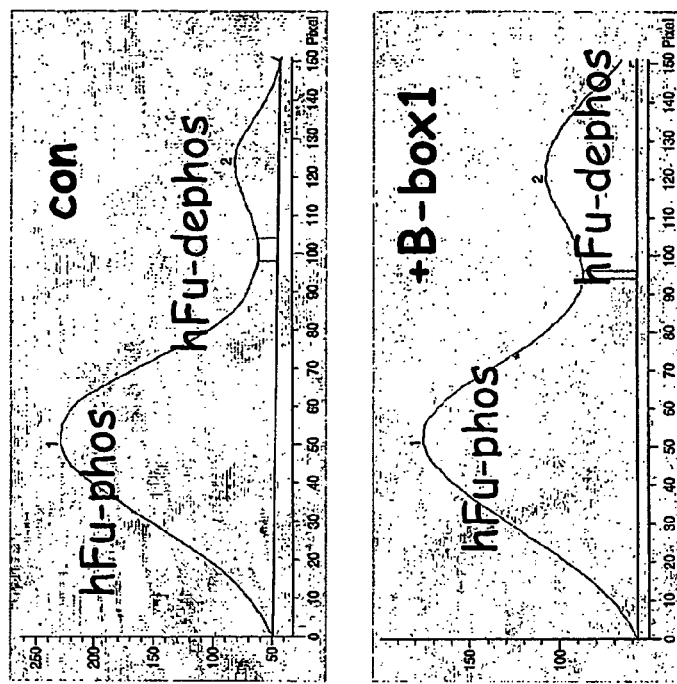
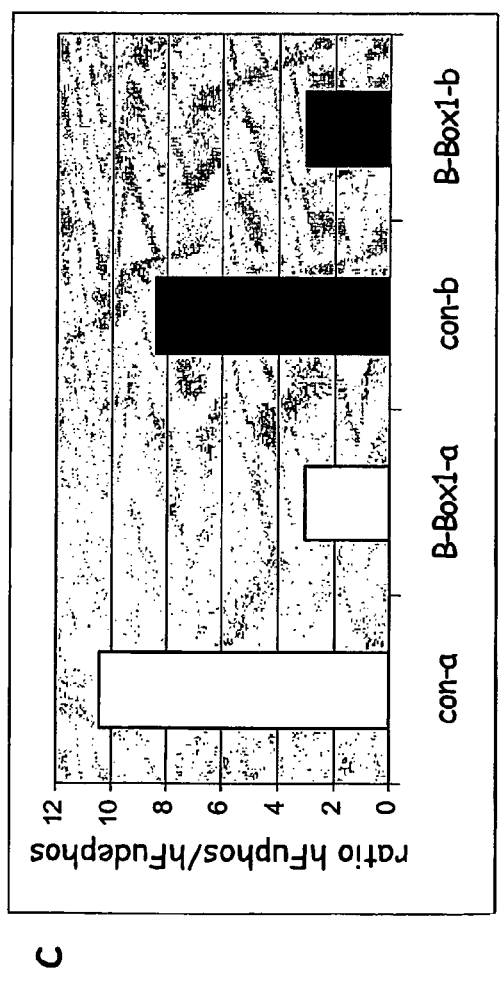

MEANS FOR USE IN TREATING DISEASES CORRELATED WITH OR CAUSED BY NON-PHYSIOLOGICAL LEVELS OF MICROTUBULE-ASSOCIATED PP2AC

This application is the National Phase of International Application PCT/EP03/05124 filed May 15, 2003 which designated the U.S. and that International Application was published under PCT Article 21(2) in English, and claims priority to U.S. Provisional Application No. 60/380,590, filed May 15, 2002.

A variety of documents is cited in this specification. The disclosure content of these prior art documents, including manufacturer's manuals, is herewith incorporated by reference in its entirety. Yet, this is not to be construed as an admission that these documents constitute prior art that is relevant to the patentability of the claimed invention.

BACKGROUND OF THE INVENTION

A variety of diseases are known to be correlated with hyper- or hypophosporylation of proteins. These proteins may be structural proteins or regulatory proteins.

An example of a disease wherein hyperphosporylation of a structural protein is observed is Alzheimer's disease. Here, microtubule-associated tau protein contains unphysiologically high amounts of phosphate residues which may be causative in the formation of paired helical filaments. Further diseases wherein a non-physiological level of phosporylated microtubule-associated proteins is observed include lissencephaly I and Opitz syndrome.

Opitz G/BBB syndrome (MIM 300000) is a congenital disorder that primarily affects the ventral midline. Prominent manifestations include mental retardation associated with dysplasia of the corpus callosum, ocular hypertelorism, cleft lip and palate, tracheo-esophageal fistulas and genitourinary defects. In addition, imperforate anus and hymen and cardiac abnormalities such as tetralogy of Fallot have been described[1]. The condition is genetically heterogeneous: both an X-linked (Xp22.3) and an autosomal locus (22q11.2; MIM145410) have been described[2]. The two forms of the disease are clinically indistinguishable. Using a positional cloning approach, we previously identified a candidate gene for the X-linked form, designated MID1, and found that it is selectively mutant in individuals with from OS[3].

The protein encoded by MID1 comprises five separate domains common to the RING-finger protein family. A sixth, the C-terminal B30.2 domain, occurs in a subset of these proteins. Most of the mutations identified to date in patients linked to OS cluster in that portion of the MID1 gene. Recently, it was shown that MID1 associates with microtubules, which indicates that it has a physiological role in microtubule dynamics. Mutant forms of MID1 do not associate with microtubules but form cytoplasmic clots instead[4].

The N-terminus of MID1 is characterized by a motif (RBCC) consisting of four independent domains: the RING finger, two B-boxes and a coiled-coil domain. This domain structure is conserved throughout the growing family of RING-finger proteins. Formation of macromolecular protein complexes has been described for several of these proteins[5,6], whereas heteromeric protein-protein interaction is ascribed to the RBCC motif[7]. Ubiquitination of target proteins mediated by a RING-finger domain is important in the post-translational regulation of many of proteins[8-11].

By yeast two-hybrid screening with MID1 as bait, it is shown that the α4 protein, a regulatory subunit of protein phosphatase 2A (PP2A)[12] (Sontag, E.; 2001), interacts with the N-terminal region of MID1. Moreover, it is shown that microtubule-associated PP2A[13] is conspicuously upregulated in an embryonic fibroblast cell line derived from an individual with OS. Our data indicate that MID1 is involved in targeting the ubiquitination machinery towards PP2A by binding to its regulatory subunit α4, and that Ser/Thr underphosphorylation of microtubule-associated proteins may be pivotal in the pathogenesis of Opitz syndrome.

Furthermore, it has been shown, that MID1 and MID2 can homo- and heterodimerize and tether α4 to the microtubules, whereby the B-boxes of MID1 and MID2 mediate the interaction with α4 (Short et al.). MID 1 association with microtubules is regulated by dynamic phosphorylation involving MAP kinase and protein phosphatase (Lin et al.).

Whereas the prior art has established that MID1 interacts via α4 with PP2Ac, there has been so far no clue how intracellular amounts of PP2Ac associated with microtubules can effectively be altered. Due to the fact that a number of diseases are correlated with or caused by non-physiological levels of microtubule-associated PP2Ac as mentioned above, there remains a need to provide means and methods of effectively altering these non-physiological intracellular levels of PP2Ac to physiological levels in order to have an effective approach for curing such diseases.

The solution to this technical problem is achieved by providing the embodiments characterized in the claims.

SUMMARY OF THE INVENTION

The present invention relates to a method of preventing or treating a disease correlated with or caused by non-physiologically increased intracellular levels of the catalytic subunit of microtubule-associated protein phosphatase 2A (PP2Ac) comprising administering to a subject affected by said disease or in danger of developing said disease a pharmaceutically effective amount of a protein selected from the group of MID1 or MID2 or a nucleic acid encoding said protein. The invention further relates to a method of preventing or treating a disease correlated with or caused by non-physiologically decreased intracellular levels of the catalytic subunit of microtubule-associated protein phosphatase 2A (PP2Ac) comprising administering to a subject affected by said disease or in danger of developing said disease a pharmaceutically effective amount of a peptidic fragment of MID1 or MID2 wherein said peptidic fragment comprises amino acids 108-165 (preferably 110-165) of MID1, amino acids 108-165 (preferably 110-165) of MID2 or an effective amount of a fragment of PP2Ac that binds to α4 but has no intrinsic phosphatase activity or a peptidic fragment of α4 (preferably amino acids 111-202) comprising the binding site to PP2Ac or a peptidic fragment of α4 comprising amino acids 236-279 or an effective amount of a nucleic acid molecule encoding said peptide fragment or an effective amount of a molecule interfering with the interaction of MID1 or MID2 with α4 or interfering with the interaction between α4 and PP2Ac or an effective amount of a molecule interfering with the regulation of these interactions. Further, the invention relates to a method of identifying a molecule that interferes with the interaction of MID1 or MID2 and α 4 comprising contacting under suitable conditions MID1 or MID2 or a peptidic fragment of MID1 or MID2 wherein said peptidic fragment comprises amino acids 108-165 (preferably 110-165) of MID1 or amino acids 108-165 (preferably 110-165) of MID2 with α4 or a peptide fragment of α4 in the presence of a candidate molecule or an effective amount of a molecule interfering with the expression of activity of MID1, MID2 and/or α4; and assessing whether said candidate molecule interferes with said interaction. Finally, the invention relates to compositions, preferably pharmaceutical compositions, comprising one or more of the above-referenced proteins or peptide fragments thereof or corresponding nucleic acids.

DETAILED DESCRIPTION OF THE INVENTION

The present invention relates to a method of preventing or treating a disease correlated with or caused by non-physiologically increased intracellular levels of the catalytic subunit of microtubule-associated protein phosphatase 2A (PP2Ac) comprising administering to a subject affected by said disease or in danger of developing said disease a pharmaceutically effective amount of a protein selected from the group of MID1 or MID2 or a nucleic acid encoding said protein.

The term "correlated with or caused by" in accordance with the present invention differentiates between the phenotypically observed phenomenon of the correlation of an intracellularly increased level of the catalytic subunit of microtubule-associated protein phosphatase 2A with a disease without necessarily concluding that this disease is caused by said increased levels of the enzyme (but not excluding that the increased level is causative) on the one hand and the causative effect of the increased level of PP2Ac on the onset of the disease on the other hand. Accordingly, in some instances the correlation is based on the causative effect whereas in other cases, the causative effect may be different from the increased level or activity of PP2Ac.

The term "non-physiologically increased intracellular levels" refers to the fact that levels are increased over levels that are found in cells of a subject not affected by the mentioned disease. PP2Ac levels can conveniently be measured by assessing the level of phosphorylation of a target protein. Yet, in many instances a direct measurement of PP2Ac levels is not necessary since the occurrence of non-physiological levels with certain diseases is established or at least suspected. Non-physiologically increased levels are at least 20%, preferably at least 30%, more preferred at least 50%, even more preferred at least 80% and most preferred at least 100% increased as compared to normal, physiological levels of the protein in the same type of cell in the same developmental stage wherein the measurement is taken essentially under the same conditions in both cells.

The term "PP2Ac" refers, in accordance with the present invention, to both, the alpha and beta isoforms of the catalytical subunit of protein phosphatase 2A (Stone et al, 1988; Hemmings et al, 1988) and as further described in the appended references.

The administration to a subject which is preferably a mammal and most preferred a human is done as recommended by the attending physician. Usually the protein referred to above or the nucleic acid encoding said protein would be formulated together with a pharmaceutically acceptable carrier or diluent. The term "composition" as employed herein comprises at least one protein and/or at least one nucleic acid molecule as outlined herein above.

The composition may be in solid, liquid or gaseous form and may be, inter alia, in a form of (a) powder(s), (a) tablet(s), (a) solution(s) or (an) aerosol(s).

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the brain artery or directly into brain tissue. The compositions prepared in accordance with the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 25 mg/kg body weight per dose; however, doses below or above this exemplary range are envisioned, especially considering the aforementioned factors. If the regimen is a continuous infusion, it should also be in the range of 1 µg to 25 mg units per kilogram of body weight per minute. Dosages of nucleic acid molecules, preferably DNA molecules in particular for intravenous administration are from approximately $10^6$-$10^{12}$. DNA may also be administered directly to the target site, e.g., by biolistic delivery to an internal or external target site or by catheter to a site in an artery.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers dextrose, dextrose and sodium chloride, lactated Ringers, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition prepared in accordance with the invention may comprise further agents depending on the specific intended use of the pharmaceutical composition. Said further agents may be drugs acting on the cellular level. It is particularly preferred that said pharmaceutical composition comprises further agents like, e.g. acetylcholine, cholinergic agonists, non-steroidal anti-inflammatory drugs, estrogens, antioxidant vitamins and cholesterol-lowering drugs.

The term "in danger of developing said disease" refers to the fact that the attending physician will diagnose a predisposition to the disease. Such a predisposition may be genetically based, such as Opitz-syndrome, type I lissencephaly of the Miller-Dieker type and X-linked double-cortex syndrome, or its onset may be expected on the basis of certain symptoms observed with the patient.

The term "MID1" refers to a protein that interacts with the α4 subunit of microtubule associated PP2Ac. The protein has been described by biophysical/parameters including the amino acid sequence in Quaderi et al, 1997.

The term "MID2" refers to a protein that has been described with regard to its biophysical/parameters including its amino acid sequence in Buchner et al, 1999.

The α4 protein has been described in the appended literature for example in Trockenbacher et al and references cited therein.

In accordance with the present invention, it was surprisingly found that MID1 and/or MID2 have a regulatory effect on the level of PP2Ac that is associated with microtubules. The N-terminal region of MID1/2 proteins interact as has been detected, in accordance with the present invention, with the α4 protein. Moreover, it is shown that MID1 is involved in targeting the ubiquitination machinery towards PP2Ac by binding to its regulatory subunit α4. The target specificity of the E3 ligase activity of functional MID1 is defined by the selective binding of the B-box 1 domain, one of the five separate domains common to the RING-finger protein family, to α4, which then mediates the binding to PP2Ac.

This finding in accordance with the present invention is particularly surprising and advantageous, since so far PP2Ac as a central cellular regulator was not amendable to external manipulations of the intracellular levels. The present invention is, in addition, surprising and advantageous, since administration of MID1 or MID2 allows the specific targeting of microtubule-associated PP2Ac levels. Insofar, there is no interference with PP2A activity elsewhere in the cell. This has the effect that diseases associated with non-physiological levels of PP2Ac associated with microtubules can be targeted without disturbing the overall activity of PP2A as a key cellular regulator.

Whereas in certain embodiments a protein, optionally in the form of a fusion protein with a heterologous protein or peptide portion can be used in the formulation of the pharmaceutical composition, in alternative embodiments a nucleic acid molecule, preferably a DNA molecule can be used for administration. There are a variety of methods for administering said nucleic acid molecule to a patient in need thereof. These methods include particle bombardment (gene gun technology), ballistic methods and/or methods making use of vectors, e.g. viral vectors as vehicles. Advantageously, the DNA encoding said protein is comprised in a vector, preferably an expression vector.

Said vector may be, for example, a phage, plasmid, viral or retroviral vector. Retroviral vectors may be replication competent or replication defective. In the latter case, viral propagation generally will occur only in complementing host/cells.

The polynucleotides or genes may be joined to a vector containing selectable markers for propagation in a host. Generally, a plasmid vector is introduced in a precipitate such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

In a more preferred embodiment of the vector the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The invention further relates to a method of preventing or treating a disease correlated with or caused by non-physiologically decreased intracellular levels of the catalytic subunit of microtubule-associated protein phosphatase 2A (PP2Ac) comprising administering to a subject affected by said disease or in danger of developing said disease a pharmaceutically effective amount of a peptidic fragment of MID1 or MID2 wherein said peptidic fragment comprises amino acids 108-165 (preferably 110-165) of MID1, amino acids 108-165 (preferably 110-165) of MID2 or an effective amount of a fragment of PP2Ac that binds to α4 but has no intrinsic phosphatase activity or a peptidic fragment of α4 (preferably aminoacids 111-202) comprising the binding site to PP2Ac or a peptidic fragment of α4 comprising amino acids 236-279 or an effective amount of a nucleic acid molecule encoding said peptide fragment or an effective amount of a molecule interfering with the interaction of MID1/MID2 with α4 or interfering with the interaction between α4 and PP2Ac or an effective amount of a molecule interfering with the regulation of these interactions, as for example rapamycin.

The term "non-physiologically decreased intracellular levels" refers to the fact that levels are decreased compared to normal levels and are found in cells of a subject not affected by the mentioned disease. PP2Ac levels can conveniently be measured by assessing the level of phosphorylation of a target protein. Yet, in many instances a direct measurement of PP2Ac levels is not necessary since the occurrence of non-physiological levels with certain diseases is established or at least suspected. Non-physiologically decreased levels are at least 20%, preferably at least 30%, more preferred at least 50%, even more preferred at least 80% and most preferred 90, 95, 98, 99 or 100% decreased as compared to normal, physiological levels of the protein in the same type of cell in the same developmental stage wherein the measurement is taken essentially under the same conditions in both cells.

The term "peptidic fragment" (or "peptide fragment") refers to fragments of the complete proteins having the same or essentially the same amino acid sequence as the corresponding portion of the full length protein. The peptidic fragments may be of varying length wherein the minimal length is preferably the length as given above and preferably have the length and amino acid composition as indicated above. The invention also comprises variants of these peptides fragments which have an altered primary amino acid sequence but retain or essentially retain the function as required by the present inventions. Variations can be effected on the DNA level, for example, by site-directed mutagenesis, followed by expression of the mutated sequence. Binding of the expressed sequence can subsequently be checked using, for example, the methodology described in the appended examples.

In variation to the above and throughout the further embodiments described in this application, the diseases may also be correlated with or caused by decreased activity of PP2Ac instead of decreased levels of PP2Ac. The various methods, compositions and uses of the invention apply mutatis mutandis to diseases correlated with or caused by said decreased activity.

This embodiment of the invention is expected to have wide application in medical therapy. Namely, in accordance with the present invention, fragments of MID1, MID2 and of α4, as well as of PP2Ac could be identified that allow the interaction with the respective binding partner, namely MID1-α4, MID2-α4, and α4-PP2Ac. Surprisingly, it could be shown that the peptidic fragments referred to above have the opposite effect of the administration of the corresponding whole protein. The administration of any of the above recited fragments of MID1/MID2, α4 or PP2Ac is thus expected to lead to the enhancement of microtubule-associated PP2Ac levels inside the cell. Therefore, this embodiment of the invention is suitable for the prevention or treatment of diseases caused by or correlated with decreased PP2Ac levels. It should be noted that this surprising aspect of the invention is also based on the finding that MID1/MID2 direct PP2Ac via the α subunit into the ubiquitin-related degradative pathway.

Alternatively, the interaction between MID1 and α4 or α4 and PP2Ac may be disturbed or abolished by a molecule interfering with the interaction of these two cellular components. Also, an effective amount of a molecule interfering with the expression or activity of MID1 and/or α4 such as an RNAi or an antisense-oligi-nucleotide, can, in accordance with the method of invention, be administered to said subject. All these different modes of administration will lead to the same result, namely an increase of intracellular microtubule-associated PP2Ac levels due to the fact that they influence the regulatory role of MID1/MID2 on the intracellular levels of microtubule-associated PP2Ac.

Without wishing to be bound by any theory, it is presently assumed that the opposite effect obtained by administration of the whole proteins and the above recited peptidic fragments (thereof) are due to the fact that the peptidic fragments do not comprise the complete set-up of structural components (in the case of the MID1/2 the ring-structure) comprised in the whole protein structures and which is responsible for the ubiquitin-related degradation of PP2Ac. As a consequence, the above recited peptidic fragments compete with the complete corresponding full-length proteins for its binding partner and outcompete said full-length proteins. Due to the fact that essential protein structures responsible for the normal targeting into the ubiquitin-related degradation pathway are missing within these peptidic fragments, microtubule-associated PP2Ac is accumulated intracellularly. Most importantly, and in line with the first embodiment of the invention, PP2A levels elsewhere in the cell are not effected by the administration of the above recited compounds. Again, this allows a targeted treatment of diseases caused or correlated with decreased levels of microtubule-associated PP2Ac without disturbing the overall activity of PP2A within the cell.

In variation to the above embodiment, fragments of PP4C or PP6C comprising the binding site for α4 may be administered. Since the binding sites of these PP2Ac-related phosphatases could differ significantly this could enable a specific interference with either PP2Ac or PP4C or PP6C degradation and as these phosphatases have different cellular functions this could lead to more specific effects.

In a preferred embodiment of the method of the present invention said disease is Opitz disease (increased level).

In a further preferred embodiment of the method of the present invention said disease is a neurodegenerative disease or osteoporosis (decreased level).

The term "neurodegenerative disease" refers to diseases that involve the degeneration of neurons by abnormal apoptosis or toxic events like in Parkinson's disease.

In a particularly preferred embodiment of the method of the present invention said disease is Alzheimer's disease or a tauopathy.

The term "tauopathy" refers to diseases involving mostly, but not exclusively genetically altered forms of tau proteins or altered levels of tau proteins.

In an additional preferred embodiment of the method of the present invention said disease is cancer including metastasis. As PP2Ac is a candidate tumor suppressor and is a potent counteractor of many oncogenic pathways and cell motility, elevated levels or activities of this enzyme are potentially prophylactic or therapeutically applicable in oncological diseases in general.

In this respect it could be shown experimentally that the PP2Ac/MID1 complex is involved in the regulation of the sonic hedgehog signalling pathway, a pathway which is supposed to be one of the most important oncogenic pathways (Wicking and McGlinn, 2001).

Overactivity of the shh/Gli-signalling leading to an overexpression of the oncogene Gli1 via the shh/Gli3 pathway has been shown in the prior art to be responsible for the development of Basal Cell Carcinoma and diverse brain tumors (Ruiz i Altaba, 2002). In addition an important role in the evolution of prostate carcinoma and melanoma has been ascribed to it (Mullor et al, 2002). When comparing patients with Opitz BBB/G syndrome and Greig encephalopathia, craniofacial similarities of these two patient groups are striking as both syndromes are characterized by hypertelorism and a broad nasal bridge. Mutations in the Gli3 gene, a central signaling molecule of the sonic-hedgehog pathway, are the underlying genetic defects in patients with Greig enzephalopathia. Moreover, cubitus interruptus, the *drosophila* homologue of the Gli3 protein, is a microtubules associated protein. The subcellular localization and transcriptional activity of said protein is regulated via diverse steps of serine/threonine phosphorylation. Starting from these observations the hypothesis of a regulatory influence of the MID1/PP2A complex on the Gli3 function and consequently on the sonic hedgehog pathway was established. The activity of microtubules associated PP2A, a central serine/threonine phosphatase, can be influenced by different molecules all interfering with the interaction of PP2A with MID1 (e.g. rapamycin, small peptides derived from the interaction domain of MID1 and α4, RNAi and antisense molecules etc., see also below). In immunofluorescense experiments it could furthermore be shown that the intracellular localization of the Gli3 transcription factor can be influenced by these molecules.

It could also be demonstrated that the overexpression of the B-Box1, a peptide derived from the MID1 domain that is responsible for α4 binding, as well as rapamycin-treatment and downregulation of α4 via RNAi of GFP-tagged Gli3-overexpressing HeLa cells led to a significant retention of the active form of Gli3 in the cytosol. Treatment of the GFP-Gli3 plus B-Box overexpressing cells with the PP2A specific inhibitor fostriecin could reverse the observed effect proofing the dependency of the Gli3 localization on PP2A activity.

Furthermore, it could be shown that overexpression of α4 on the other hand led to a significant release of GFP-Gli3 to the nucleus.

One of the most important targets of the Gli3 transcription factor is the patched gene. In order to analyse HeLa cells for Gli3 activity after treatment with the different molecules, semiquantitative RT-PCR of cells overexpressing the B-Box1 and the α4 protein were carried out. The HeLa cells were tested for Gli3-, Gli1-(which is another target of the Gli3 transcription factor) and patched-expression. As expected, B-Box1 expression leads to significant reduction of the patched message while α4 overexpression results in an increase of the patched message.

It could therefore be shown that molecules which interfere with the MID1/PP2A interaction and which lead to the accumulation of PP2Ac are negative effectors of the sonic-hedgehog pathway. This finding provides therefore a promising target for the development of anticarcinogenic drugs interfering with this central oncogenic pathway.

In order to test specific interference with the MID1/PP2A complex for putative anticarcinogenic effects, HeLa cells were transfected with specific anti-α4 RNAi molecules. Depending on the time of exposure, a dramatic decrease in the proliferation of these normally rapidly growing tumor cells was detected in the cells containing anti-α4 RNAi molecules than compared to mock-transfected cells and to cells treated with unspecific RNAi molecules. BrdU-labelling and subsequent FACS-analysis revealed that the reduction of cell numbers resulted from G1-phase arrest rather than from increased apoptosis.

In contrast, downregulation of the MID1 protein, for example via RNAi, resulted in a dramatic induction of apoptosis.

Thus, by interfering with the MID1/PP2A complex, at least two different anticarcinogenic mechanisms (cell arrest and apoptosis) could be induced.

The pharmacologically induced accumulation of PP2Ac by molecules interfering with the function of the MID1/PP2Ac complex (see also below) represents therefore a promising route to the development of novel powerful anticancer drugs.

In this respect, it could also be shown that hFused, which is a kinase-like protein involved in the hedgehog signalling pathway and which can trigger the nuclear translocation of Gli3, is a target of the MID1/PP2A complex. It could clearly be demonstrated that the hFused phosphorylation status can be influenced by the manipulation of the activity of microtubules-associated PP2A via the MID1/α4/PP2A-complex.

In another preferred embodiment of the method of the present invention said disease is an inflammatory disease. Inflammatory diseases include acute inflammatory states, such as sepsis and acute lung injury.

The invention also relates to a method of the present invention wherein said protein or said peptide fragment is fused to TAT or functionally similar peptidic fragments that enable the direct transduction of proteins into cells in vivo (Schwarze et al, 2000).

TAT is a peptidic fragment of the HIV1-TAT protein. If this peptide is fused to another protein it can trigger an efficient direct transduction of this protein into living cells and is thus a particularly advantageous active ingredient administered in accordance with the present invention.

In a further preferred embodiment of the method of the present invention the molecule interfering with the expression of MID1 and/or α 4 is an RNAi.

RNAi is an interfering RNA molecule described, for example, WO 01/75164 or WO 99/32619. The RNAi molecule used in accordance with the present invention preferably has a region of homology with the target gene of about 19 to 23, more preferred of about 21 to 23 consecutive nucleotides. Within this region of homology, the nucleotides are either identical or essentially identical with the corresponding region of the target gene. Administration of the RNAi molecules has been described in the art; see above recited references.

In an additional preferred embodiment of the method of the present invention said molecule interfering with the interaction of MID1 with α4 is a small molecule.

Small molecules may be small inorganic or small organic molecules. Libraries of small molecules are commercially available on the market.

In a preferred embodiment the small molecule is rapamycin.

The interaction of α4 with PP2Ac seems to be regulated by the kinase mTOR. Active mTOR signaling promotes the interaction between α4 and PP2Ac, inhibition of mTOR by rapamycin results in a dissociation of α4 from PP2Ac and leads to an increase in PP2Ac activity (Peterson et al, 1999). In accordance with the findings of the present invention that the α4-PP2Ac interaction is important for the degradation of PP2Ac this observed increase in PP2Ac activity could be caused by increased levels of PP2Ac due to a compromised ubiquitin-dependent degradation. Thus rapamycin or close analogues of are candidate molecules for interfering with the degradation pathway of PP2Ac and as it is a lipophilic molecule that readily passes the blood-brain barrier and shows only limited systemic toxicity it might be therapeutically applicable to enhance the dephosphorylation of tau in Alzheimer's disease. Interestingly, some of the known effects of rapamycin (antiproliferative, antimigratory) are nicely fitting with the profile of a compound that interferes with PP2Ac degradation.

In a different preferred embodiment of the method of the present invention said disease is correlated with or caused by apoptosis. These diseases include especially diseases that involve enhanced apoptosis of specific cells, such as developmental diseases but also degenerative diseases like keratoconus, retinal degeneration, degenerative arthritis, intoxication, Huntington's and Parkinson's disease.

The invention further relates to a composition comprising a protein selected from the group of MID1 or MID2 or a nucleic acid encoding said protein.

The composition of the present invention comprises the above recited ingredients alone or in combination in one or more containers. The proteinaceous matter may be in freeze dried form or contained in an aqueous, preferably buffered solution. Appropriate buffers include physiological saline. In any case, it is preferred that the ingredients of the composition of the invention are maintained in a sterile environment. The nucleic acid molecule may also be maintained in the composition in freeze dried or in aqueous, preferably buffered solution.

The invention also relates to a composition comprising a peptidic fragment of MID1 or MID2 wherein said peptidic fragment comprises amino acids 108-165 (preferably 110-165) of MID1 or amino acids 108-165 (preferably 110-165) of MID2 or an effective amount of a fragment of PP2Ac that binds to α4 but has no intrinsic phosphatase activity or a peptidic fragment of α4 (preferably amino acids 111-202)

comprising the binding site to PP2Ac or a peptidic fragment of α4 comprising amino acids 236-279 or an effective amount of a nucleic acid molecule encoding said peptide fragment or an effective amount of a molecule interfering with the interaction of MID1/MID2 with α4 or interfering with the interaction between α4 and PP2Ac or an effective amount of a molecule interfering with the regulation of these interactions, preferably, rapamycin or an effective amount of a molecule interfering with the expression or activity of MID1, MID2 and/or α4.

In a preferred embodiment of the method of the present invention said composition is a pharmaceutical composition.

As regards the particular formulation of the pharmaceutical composition and the optional further ingredients, it is referred to the description provided herein the above.

Further, the invention relates to a method of identifying a molecule that interferes with the interactions between either MID1 and α4 or α4 and PP2ac (or PP4C/PP6C) comprising
  (a) contacting under suitable conditions MID1 or MID2 or a peptidic fragment of MID1 or MID2 wherein said peptidic fragment comprises amino acids 108-165 (preferably 110-165) of MID1 or aminoacids 108-165 (preferably 110-165) of MID2 with α4 or a peptidic fragment of α4 preferably comprising amino acids 236-279 or contacting α4 or a peptidic fragment of α4 preferably comprising amino acids 236-279 with PP2Ac or PP4C or PP6C or a peptidic fragment of PP2Ac or PP4C or PP6c in the presence of a candidate molecule; and
  (b) assessing whether said candidate molecule interferes with said interaction.

The term "suitable conditions" refers to conditions that allow an interaction of the various molecules. An example of such conditions are physiological conditions like for example 50 mM sodiumphosphate buffer at pH=7.0 and 150 mM sodiumchloride or solutions of similar ionic strength and pH. In addition, suitable conditions refer to the possibility that either one of the peptides or the compound can be attached to a solid phase. The assessment of step (b) may be affected using any appropriate readout system. For example, it is possible to analyse protein-protein interactions in yeast by the two-hybrid system; readout in this case normally is growth of the yeast cells containing respective interacting proteins. Analogously, two-hybrid systems exist that have as readout growth if two given (normally interacting) proteins do no more interact. Thus incubation of these yeast cells with varying compounds should enable to identify a compound that interferes with the given interaction by growth of the yeast cells in the presence of this compound (Vidal and Endoh, 1999). Another possibility is to screen for compounds interacting with for example the peptidic fragment 108-165 (preferably 110-165) of MID1 etc. by ultrahigh throughput screening using as a readout altered laserbeam reflections of the peptide if it interacts with a compound. Such compounds can then be tested if they interfere with the interaction of MID1 and α4.

The molecules identified in accordance with the method of the invention may be formulated into a pharmaceutical composition and employed as outlined herein the above. Alternatively, these molecules may serve as a lead compound for the development of a drug that is useful in treating a disease as outlined above. Suitable methods for developing such downstreamed developments are also comprised in the present invention and referred to herein below.

Thus, additionally, the invention relates to a method of refining a compound identified by the method as described herein above, said method comprising the steps of said methods and:

(1) identification of the binding sites of the compound and the DNA or mRNA molecule by site-directed mutagenesis or chimeric protein studies;
  (2) molecular modeling of both the binding site of the compound and the binding site of the DNA or mRNA molecule; and
  (3) modification of the compound to improve its binding specificity for the DNA or mRNA.

All techniques employed in the various steps of the method of the invention are conventional or can be derived by the person skilled in the art from conventional techniques without further ado. Thus, biological assays based on the herein identified nature of the proteins/(poly)peptides may be employed to assess the specificity or potency of the drugs wherein the increase of one or more activities of the proteins/(poly)peptides may be used to monitor said specificity or potency. Steps (1) and (2) can be carried out according to conventional protocols. A protocol for site directed mutagenesis is described in Ling M M, Robinson B H. (1997) Anal. Biochem. 254: 157-178. The use of homology modeling in conjunction with site-directed mutagenesis for analysis of structure-function relationships is reviewed in Szklarz and Halpert (1997) Life Sci. 61:2507-2520. Chimeric proteins are generated by ligation of the corresponding DNA fragments via a unique restriction site using the conventional cloning techniques described in Sambrook (1989), loc. cit. A fusion of two DNA fragments that results in a chimeric DNA fragment encoding a chimeric protein can also be generated using the gateway-system (Life technologies), a system that is based on DNA fusion by recombination. A prominent example of molecular modeling is the structure-based design of compounds binding to HIV reverse transcriptase that is reviewed in Mao, Sudbeck, Venkatachalam and Uckun (2000). Biochem. Pharmacol. 60: 1251-1265.

For example, identification of the binding site of said drug by site-directed mutagenesis and chimerical protein studies can be achieved by modifications in the (poly)peptide primary sequence that affect the drug affinity; this usually allows to precisely map the binding pocket for the drug.

As regards step (2), the following protocols may be envisaged: Once the effector site for drugs has been mapped, the precise residues interacting with different parts of the drug can be identified by combination of the information obtained from mutagenesis studies (step (1)) and computer simulations of the structure of the binding site provided that the precise three-dimensional structure of the drug is known (if not, it can be predicted by computational simulation). If said drug is itself a peptide, it can be also mutated to determine which residues interact with other residues in the (poly)peptide of interest.

Finally, in step (3) the drug can be modified to improve its binding affinity or ist potency and specificity. If, for instance, there are electrostatic interactions between a particular residue of the (poly)peptide of interest and some region of the drug molecule, the overall charge in that region can be modified to increase that particular interaction.

Identification of binding sites may be assisted by computer programs. Thus, appropriate computer programs can be used for the identification of interactive sites of a putative inhibitor and the (poly)peptide by computer assisted searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. Modifications of the drug can be produced, for example, by peptidomimetics and other inhibitors can also be identified by the synthesis of peptidomimetic combinatorial libraries through successive chemical modification and testing the resulting compounds. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of activators of the expression of the (poly)peptide of the invention can be used for the design of peptidomimetic activators, e.g., in combination with the (poly)peptide of the invention (Rose, Biochemistry 35 (1996), 12933-12944; Rutenber, Bioorg. Med. Chem. 4 (1996), 1545-1558).

In accordance with the above, in a preferred embodiment of the method of the invention said compound is further refined by peptidomimetics.

The invention furthermore relates to a method of modifying a compound identified or refined by the method as described herein above optionally comprising the method steps as indicated above as a lead compound to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophylic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetates, or (xiv) N-acetylation to amides, phenylcarbamates, or (xv) synthesis of Mannich bases, imines, or (xvi) transformation of ketones or aldehydes to Schiff's bases, oximes, acetates, ketales, enolesters, oxazolidines, thiozolidinesor combinations thereof; said method optionally further comprising the steps of the above described methods. The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

The invention also relates to the preparation of a composition, preferably a pharmaceutical composition comprising the steps of the above recited methods for identifying an interfering molecule or of refining or modifying the identified molecule and of formulating the resultant molecule with a pharmaceutically acceptable carrier or diluent.

The preparation of the (pharmaceutical) composition can be effected according to standard protocols in accordance with, inter alia, the teachings provided above.

Finally, the present invention relates to the use of any of the above recited proteins or peptidic fragments, peptidomimetics thereof, or molecules interfering with the interaction of MID1 or MID2 with α4 or of α4 with PP2Ac or the molecule interfering with the expression or activity of MID1 and/or α4 or the modified or refined derivatives thereof for the preparation of a pharmaceutical composition for the treatment of the above recited diseases.

The Figures show:

FIG. 1 Association of MID1 with polyubiquinated proteins. a, COS7 cell extracts from cells transfected with V5-tagged MID1 (lanes 5 and 6), V5-tagged protein kinase C (PKC) (lanes 1 and 2) or empty vector (lanes 3 and 4) in the presence (lanes 2, 4 and 6) or absence (lanes 1, 3 and 5) of the proteasome inhibitor LLnL were precipitated with anti-V5, separated by SDS-PAGE and immunoblotted with the antibodies indicated. Asterisks indicate IgG heavy chains. b, COS7 extracts from cells overexpressing myc-tagged MID1 (lanes 3 and 4) or empty vector (lanes 1, 2) in the presence (lanes 2 and 4) or absence (lanes 1 and 3) of lactacystin were precipitated with anti-myc and analyzed on a western blot with anti-ubiquitin (upper panel) and, subsequently, anti-myc (lower panel). As described previously[20], anti-myc and anti-V5 detect two specific bands of different sizes, both representing C-terminally tagged MID1. Asterisks indicate IgG heavy chains.

FIG. 2 a, Positive clones found in a yeast two-hybrid screen in a fetal brain library using MID1 as bait. The strength of interaction, quantified by β-Gal reporter gene activity, is expressed as mean and standard deviation of three independent experiments on the right. Full-length α4 is shown for comparison. 'PP2Ac-bs' indicates the reported PP2Ac binding site on α□. Residues 172-290 are present on all positive clones. b, Mapping of the binding site of α4 on MID1 using deletion mutants as baits. Abbreviations: RF, RING finger; BB1, B-box 1; BB2, B-box 2; FNIII, fibronectin type III domain; B30.2, conserved C-terminal domain. c, Yeast his$^-$ leu$^-$ trp– plate showing selective growth for two-hybrid combinations of α4 with MID1 and MID2 and no growth for combinations with three other RING-finger proteins. The p53/SV40 T-antigen serves as a positive control for strong interaction between the two combined fusion proteins.

Figure 3:
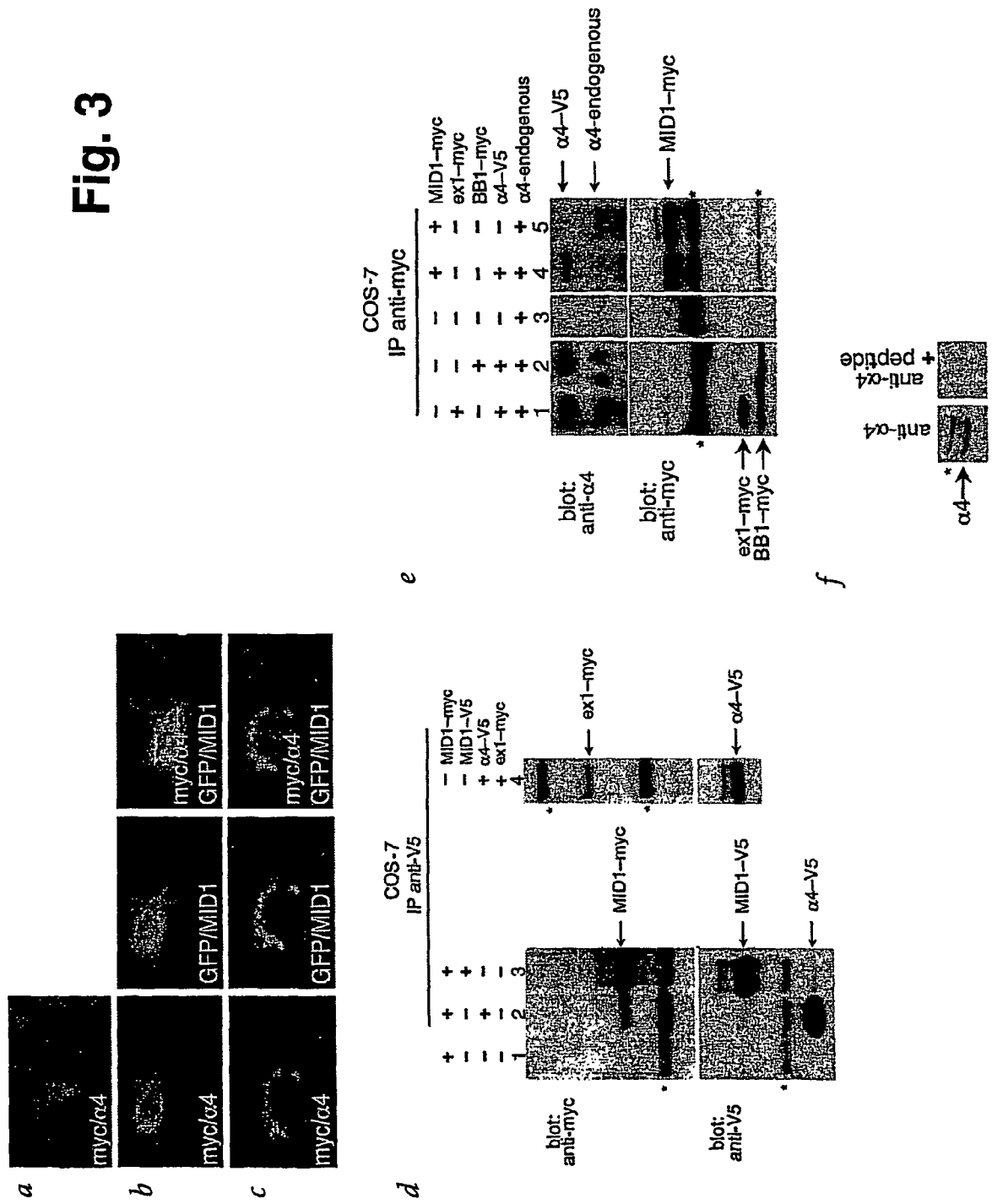

FIG. 3 The MID1-α4 interaction in COS7 cells. a, Cytoplasmic distribution of overexpressed myc-tagged α4 (myc/α4), detected by immunofluorescence using anti-myc. b, c, Co-expression of myc-tagged α4 with wildtype GFP-MID1 (b) or mutant GFP-MID1 (c). Immunofluorescence detection of anti-myc (left columns, red pattern), GFP (middle columns, green pattern) or both (right columns, yellow pattern). d, Immunoprecipitation (IP) of V5-tagged α4 (α4N5) in COS7 extracts transfected with: myc-MID1 (lane 1), myc-MID1 and V54 (lane 2), myc-MID1 and V5-MID1 (lane 3) or the myc-tagged RB domain of MID1 (ex1) and V5-α4.□□V 5lane 4). Precipitates were separated on 7.5% polyacrylamide gels and blotted with anti-myc (upper panel) and then anti-V5 (lower panel). e, Immunoprecipitation of myc-tagged MID1 in COS7 extracts transfected with: the myc-tagged RB domain of MID1 (ex1) and V5-α4 (α4N5, lane 1), myc-tagged B-box 1 of MID1 and V5-α4 (α4N5, lane 2), an empty pBud vector (lane 3), myc-MID1 and V5-α4 (α4N5, lane 4) or myc-tagged MID1 alone (lane 5); precipitates were separated by PAGE, blotted and probed with anti-α4 (anti-□4, upper panel) and then anti-myc (lower panel). Asterisks indicate IgG heavy and light chains. f, Antibody specificity control: cell lysates containing endogenous α4 were analyzed by western blotting using a polyclonal antibody detecting the first 40 aa of α4 (f, lane 1). The signal is suppressed by the addition of antigenic peptide (f, lane 2). Asterisk indicate the specific detection of a variant protein form of endogenous α4.

Figure 4:
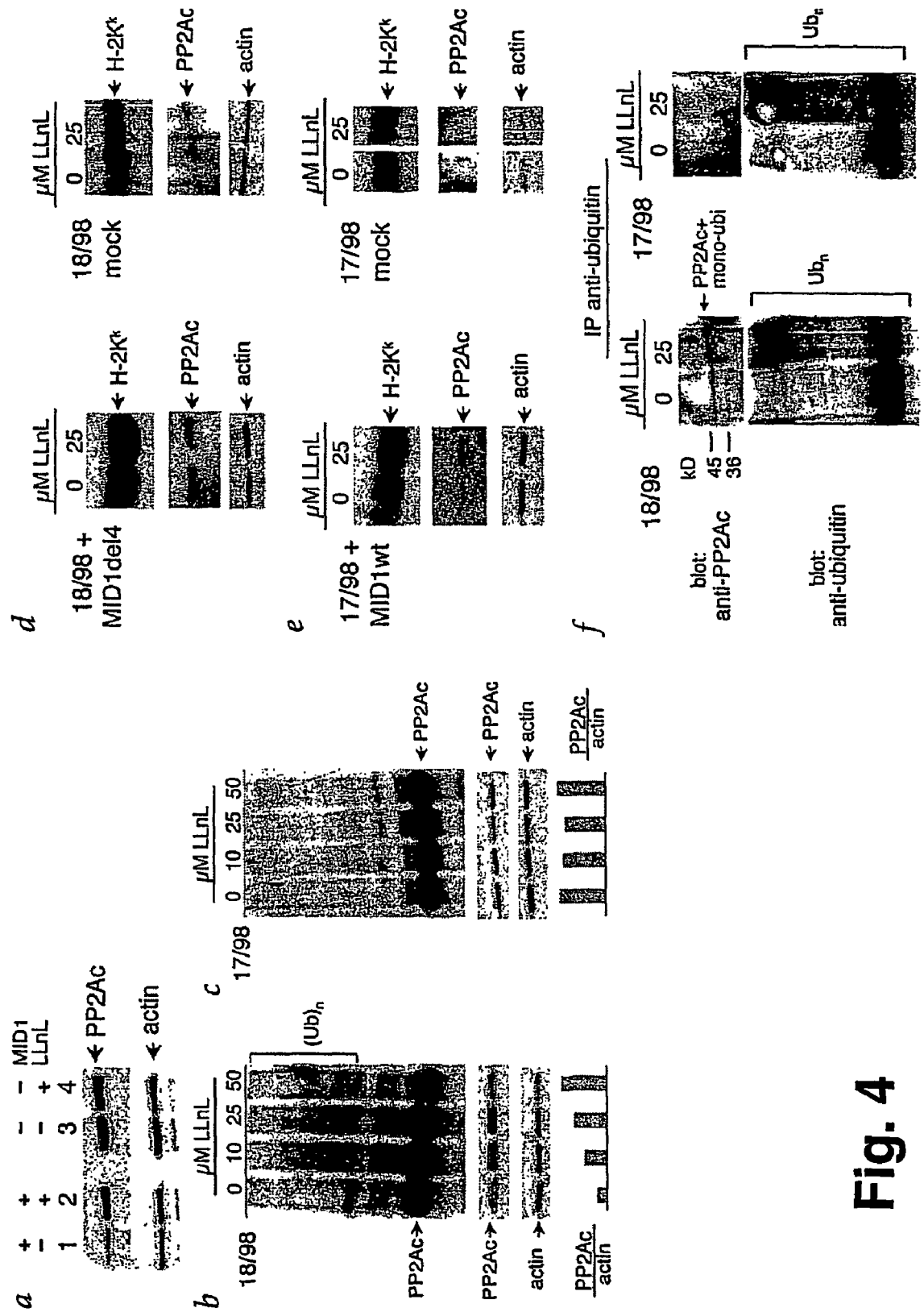

FIG. 4 Regulation of PP2A by ubiquitin-mediated proteolysis in embryonic fibroblasts. a, Detection of PP2A in 293 cells expressing V5-tagged MID1 (lanes 1, 2), as well as in control cells (lanes 3, 4) in the presence (lanes 2 and 4) or absence (lanes 1 and 3) of the proteasome inhibitor LLnL using an antibody to the C subunit of PP2A. Each lane had 52 µg of protein loaded. Detection of actin on the same blot (lower panel) was used as a control to verify comparable for protein loading. b, The embryonic fibroblast cell line 18/98 was exposed to increasing amounts of LLnL (as indicated on the top) before lysis. Western blotting was carried out with an antibody detecting the catalytic subunit of PP2A (middle panel). Extended exposure of the same blot (upper panel) reveals polyubiquitinylated PP2Ac species. Actin detection (lower panel) was used to verify comparable protein loading (50 µg/lane). Bars at the bottom represent densitometric ratios of PP2Ac versus actin. c, The same experiment as in (b) carried out with cells from an embryonic fibroblast line derived from an age-matched fetus with OS. d, The embryonic fibroblast cell line 18/98 used in (b) was transfected with mutant MID1 (del4) or an empty pMACSK$^k$.II vector (mock); positively transfected cells were enriched by MACS sorting via cotransfected H-2K$^k$. Transfected cells untreated (left) or treated (right) with LLnL were analyzed by western blotting with anti-PP2Ac (middle panel). Western-blot detection of H-2K$^k$ (upper panel) shows successful transfection and cell sorting. Actin detection (lower panel) was used to verify comparable protein loading (10 µg/lane). e, The same experiment as in (d) using the same OS-derived cell line as used in (c), transfected with wildtype MID1 or an empty PMACSK$^k$.II vector (mock). f, Immunoprecipitation of ubiquitin from lysates of the control embryonic fibroblasts (same as in a, b and d) and the OS-derived embryonic fibroblasts (same as in c and e), treated (right) or not (left) with LLnL, using monoclonal anti-ubiquitin. We analyzed the precipitates by western blotting using anti-PP2Ac (upper panel) and, subsequently, anti-ubiquitin (lower panel) to confirm successful immunoprecipitation.

Figure 5:
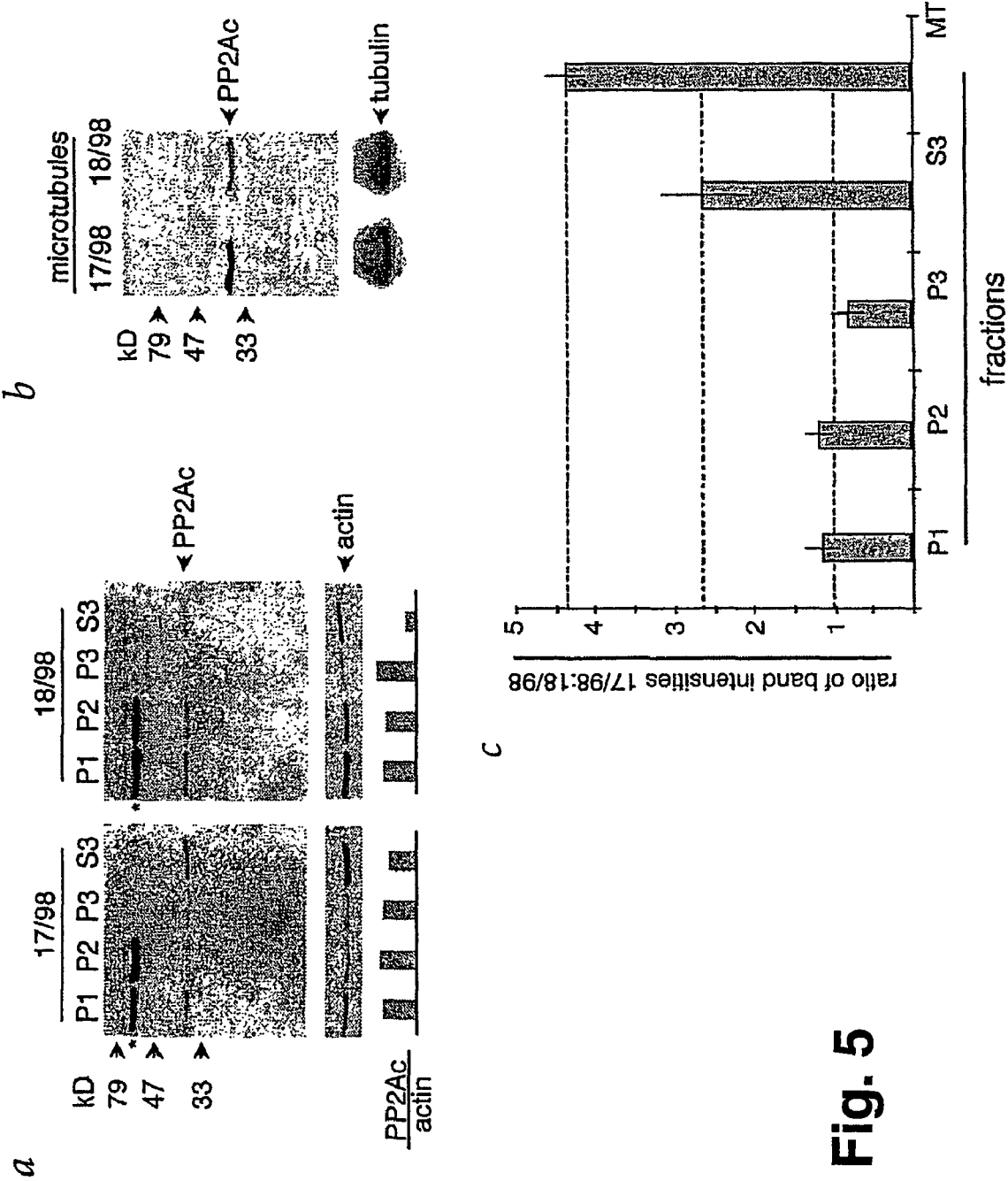

FIG. 5 Dependence of PP2Ac quantity on MID1 expression. a, Western blot analysis using anti-PP2Ac of subcellular fractions prepared by sequential centrifugation (see Methods) from OS-derived embryonic fibroblasts (17/98; left) or an age-matched control cell line (18/98; right). Pellet P1 is enriched for nuclear compartments, whereas pellet P2 represents mainly membrane-associated fractions, P3 includes insoluble cellular components and S3 is the cytosolic fraction. Anti-actin blotting (lower panel) is used to normalize protein amounts between lanes; bar graphs indicate the PP2Ac/actin densitometric signal ratio. Bands marked by asterisk represent either unspecific cross-reaction of the anti-PP2Ac or, in pellets P1 and P2, dimer formation of the catalytic subunit. b, Western-blot analysis of purified microtubules of the same cells as in (a) using the same anti-PP2Ac (upper panel). Tubulin detection (lower panel) is included to verify similar protein loading (2 µg/lane). c, Ratios of band intensities versus actin in each fraction were calculated as mean and SD of three independent experiments.

Figure 6:
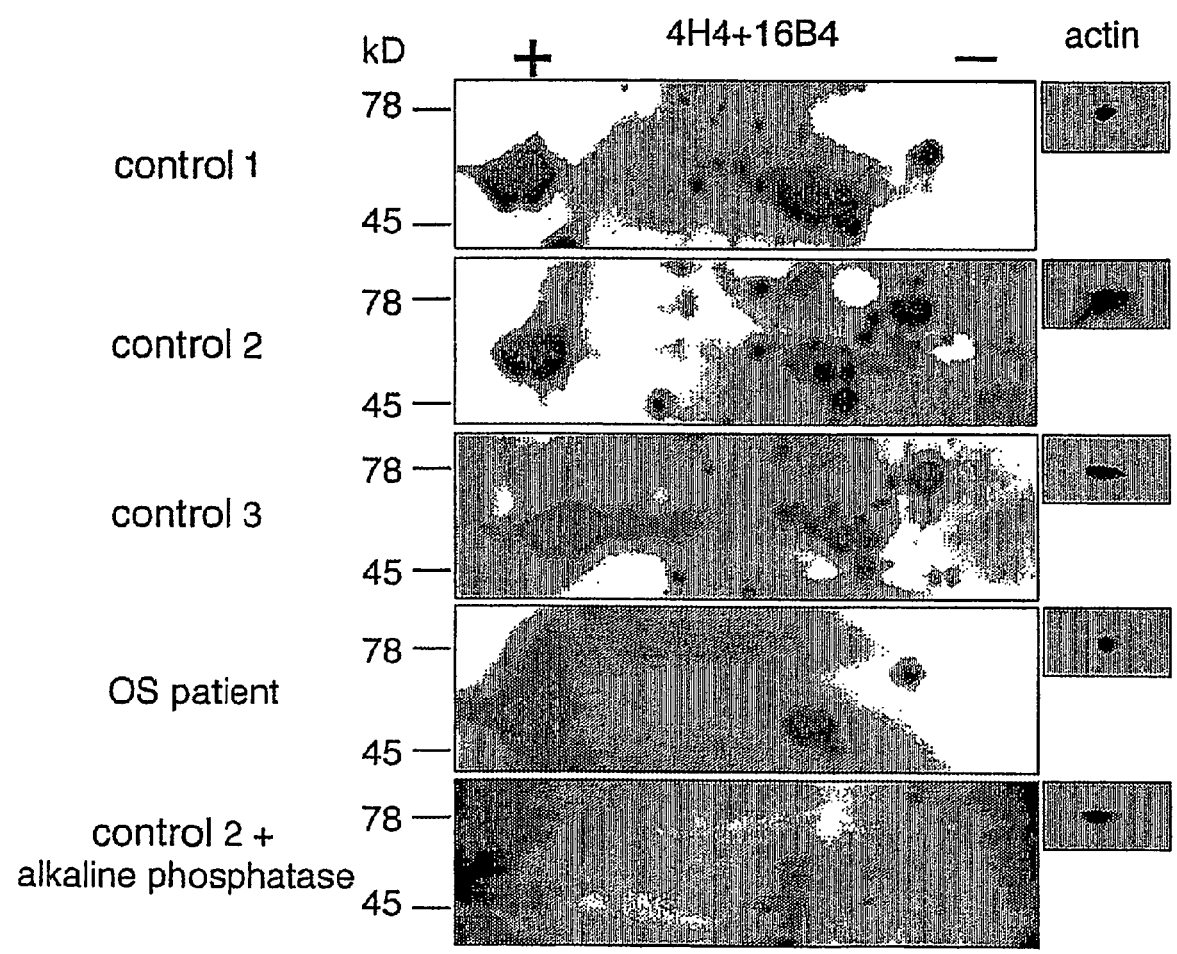

FIG. 6 Hypophosphorylation of cytosolic and microtubule-associated proteins in OS-derived embryonic fibroblasts. Two-dimensional western blot of purified microtubules (20 µg protein per blot) from cell lines derived from three age-matched controls (top three panels) and from a fetus with OS using pooled phopho-residue-specific antibodies 4H4 and 16B4. Preincubation of the blot with alkaline phosphatase (bottom panel) confirms the specificity of the antibodies for phospho residues. Detection of actin (close-ups on the right) are included to verify similar protein loading.

Figure 7:
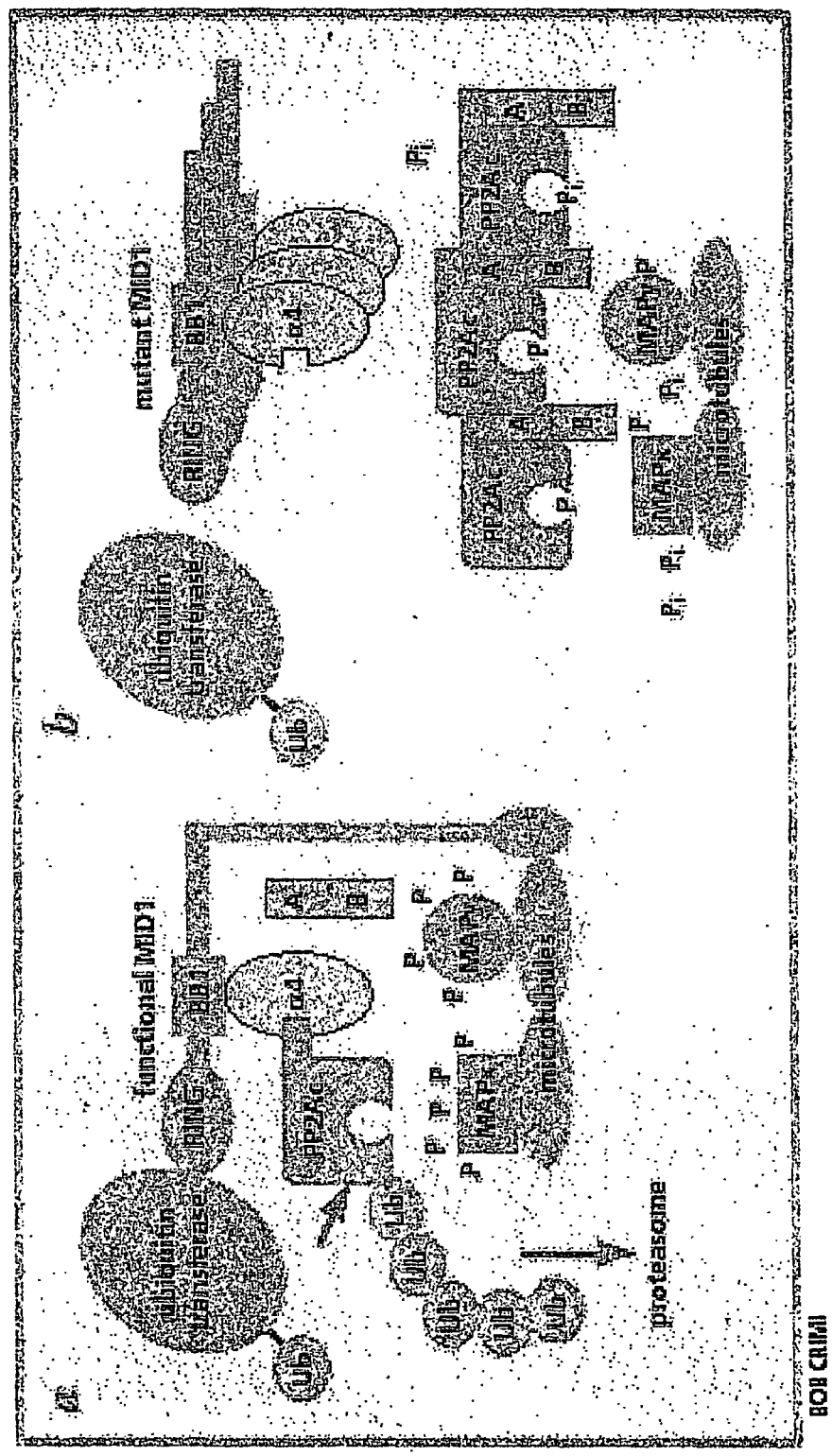

FIG. 7 Hypothetical model of the MID1-mediated ubiquitin-dependent regulation pathway of PP2A and its disruption in OS. Microtubules and as-yet-undefined associated phosphorylated (P) proteins (MAPx,y) are indicated at the bottom. $P_i$, inorganic phosphate; Ub, ubiquitin; RING, RING-finger domain; BB1, B-box 1; A and B, PP2A subunits found with microtubule-associated PP2A (not drawn to scale for topological reasons); ubiquitin transferase, protein complex harboring a ubiquitin-conjugating enzyme and potentially other ancillary proteins. Asterisks denote mutations in the C-terminus of MID1.

Figure 8:
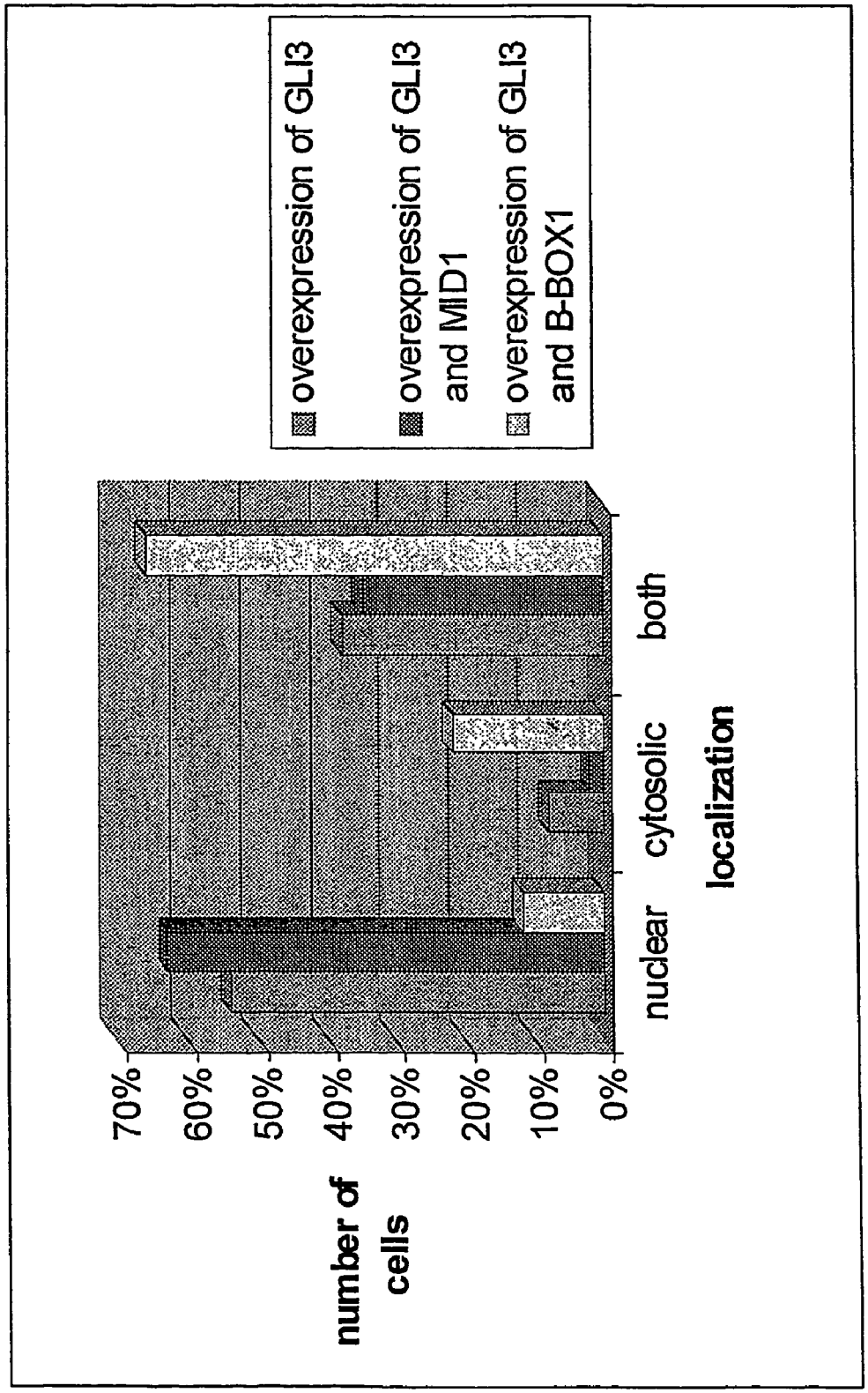

FIG. 8 Localization of GFP-GLI3 in cultured U373MG cells. U373MG cells were transfected with GFP-GLI3, GFP-GLI3 and myc-tagged MID1 and with GFP-GLI3 and myc-tagged B-BOX1. 24 hours after transfection the localization of GFP-GLI3 was studied. 100 cells per experiment were counted. We observed a significant change of GFP-GLI3 from nucleus to cytosol when coexpressed with B-BOX1.

FIG. 9 Tau-1 immunoreactivity is significantly increased in postnatal sympathetic neurons in vitro after transfection with a plasmid encoding the B-BOX1 (*p<0.0001, unpaired t-test, average neuronal fluorescence intensity of nontransfected neurons=100%). Neurons transfected with a plasmid encoding an inactive mutated form of the B-BOX1 on neurons expressing EGFP alone do not exhibit different fluorescent levels when compared to non-transfected neurons. The intensity of pan-Tau immunoreactivity in unchanged in all groups investigated.

Figure 10:
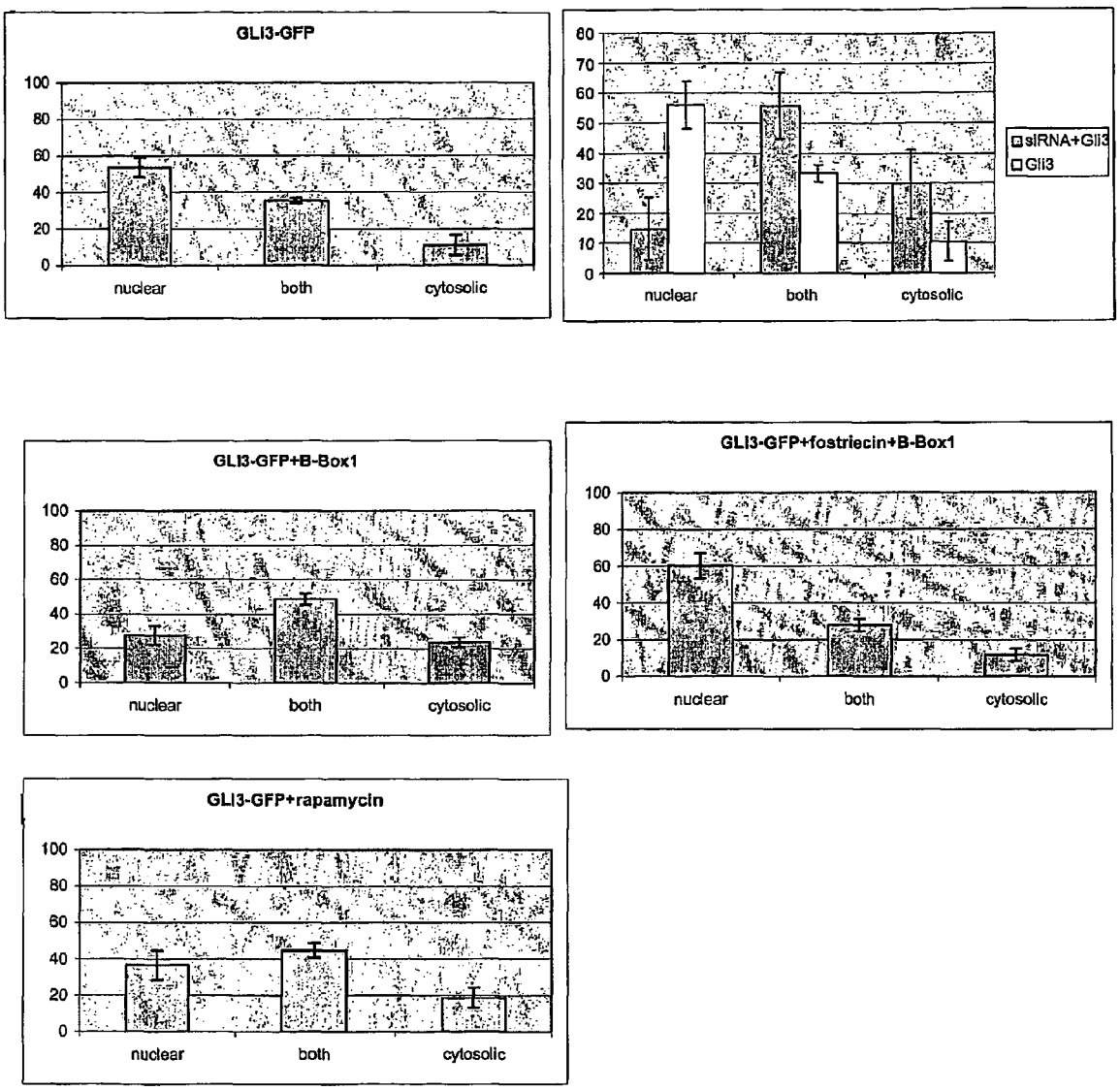

FIG. 10: Influence of diminished PP2Ac degradation on the localization of the transcription factor Gli3. Top left: Expression of GFP-tagged Gli3 in HeLa-cells, the bars indicate the number of cells showing cellular localization of GFP-fluorescence in the nucleus, the cytosol or in both, respectively; top right: Comparison of Gli3 localization in cells as treated before versus cells that express, due to siRNA treatment, less α4; middle row left: Analogous to top left, but upregulation of PP2Ac induced by overexpression of dominant negatively acting Bbox1, instead of α4-siRNA; middle right: same treatment of HeLa cells as middle left, but in the presence of the highly specific PP2Ac-inhibitor fostriecine; bottom: Gli3 expression in the presence of the immunosuppressant rapamycin, which is known to induce PP2Ac activity, probably via indirect inhibition of the PP2Ac-α4 association.

Figure 11:
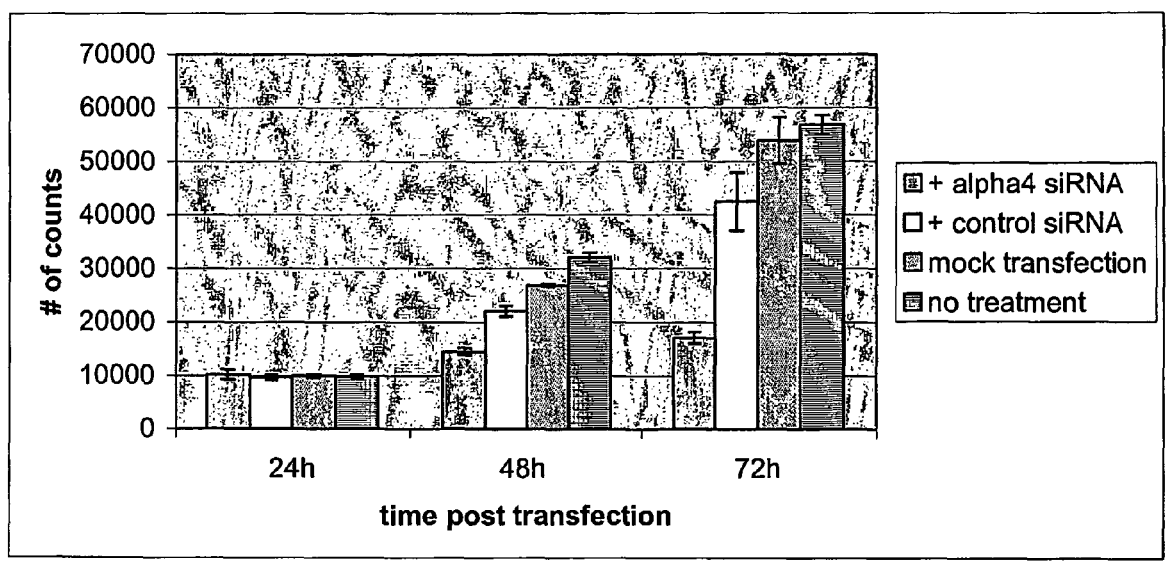

FIG. 11: Effect of downregulation of α4 by RNAi on the proliferation of HeLa cells. Hela cells were transfected with anti-α4 RNAi molecules and cell counts were performed after 24, 48 and 72 hours incubation in growth conditions. As controls untreated cells, cells treated with control siRNA, and mock-transfected cells were used.

Figure 12:
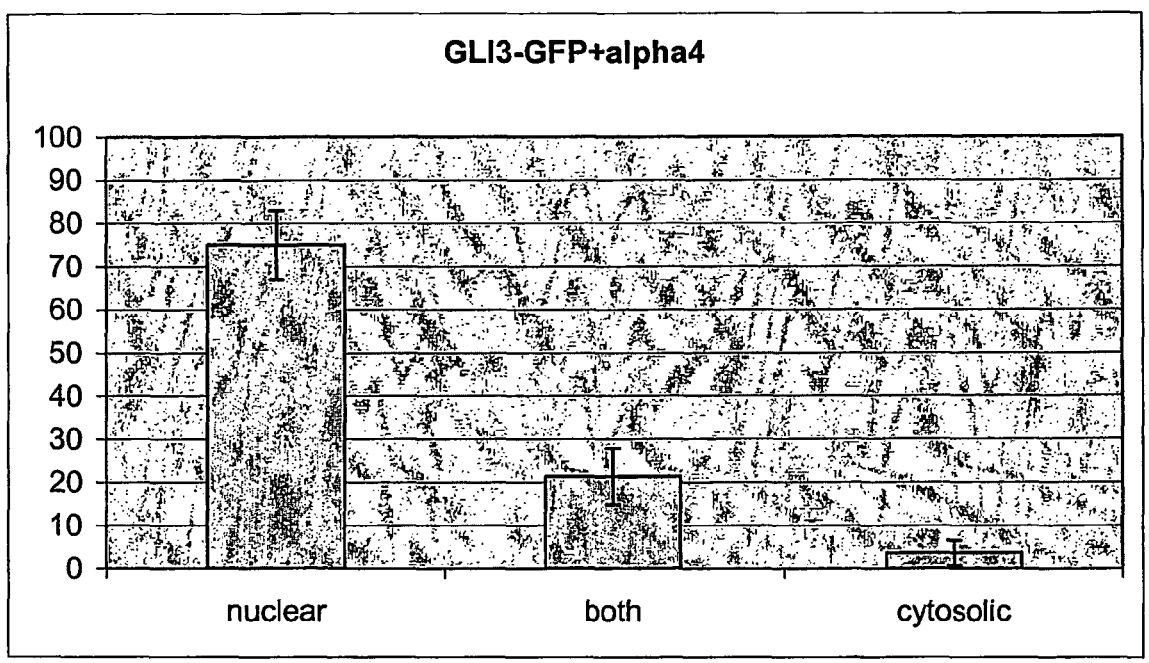

FIG. 12: Effect of overexpression of α4 on the localization of overexpressed GFP-tagged Gli3 in HeLa cells. Bars indicate the number of cells showing cellular localization of GFP-fluorescence in the nucleus, the cytosol or both, respectively. All experiments were done with GFP tagged to the C- and N-terminus of Gli3 as well as with the V5 antigene tagged to the Gli3 C- and N-terminus.

Figure 13:
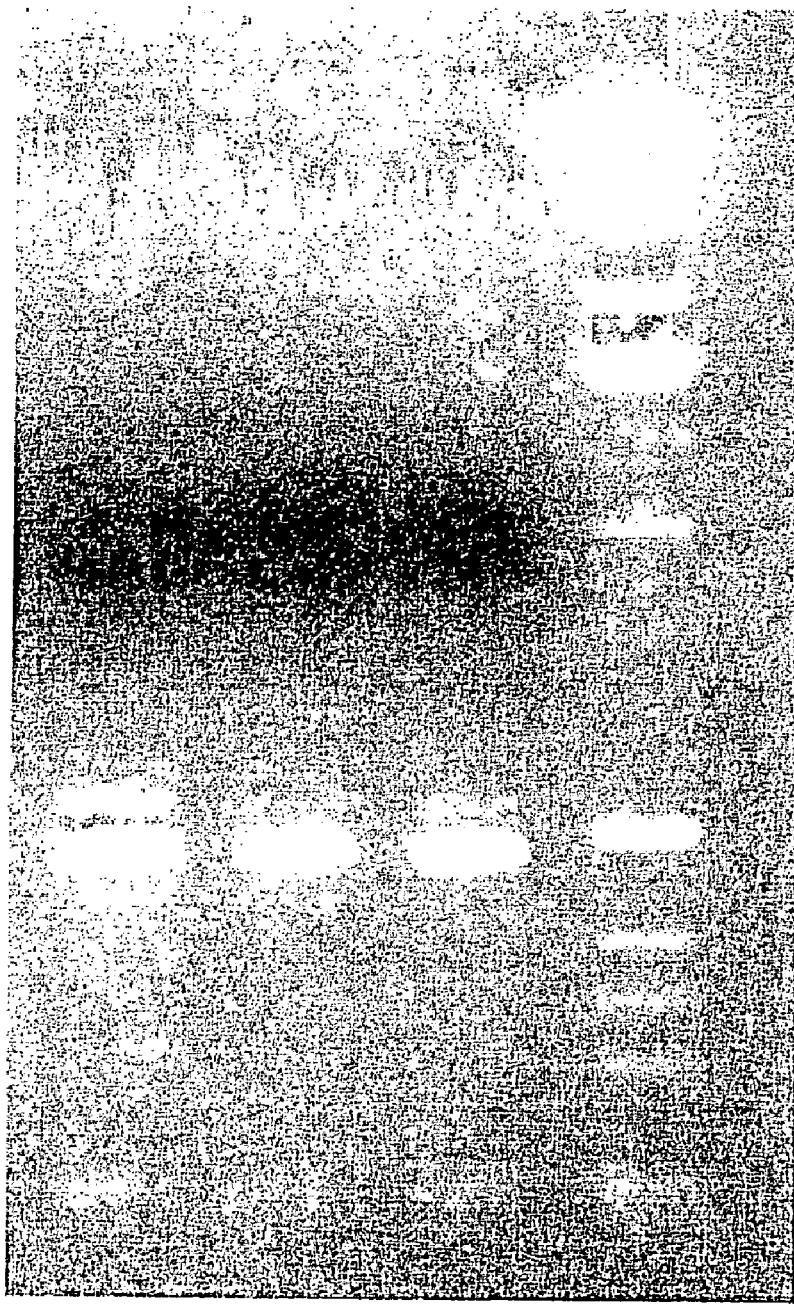

FIG. 13: Effect of altered Gli3 localization on the transcription of the patched gene. Patched-specific semiquantitative RT-PCR analysis of HeLa cells overexpressing α4 (lane 1) or Bbox1 (lane 2) or mock-transfected (lane 3).

Figure 14:
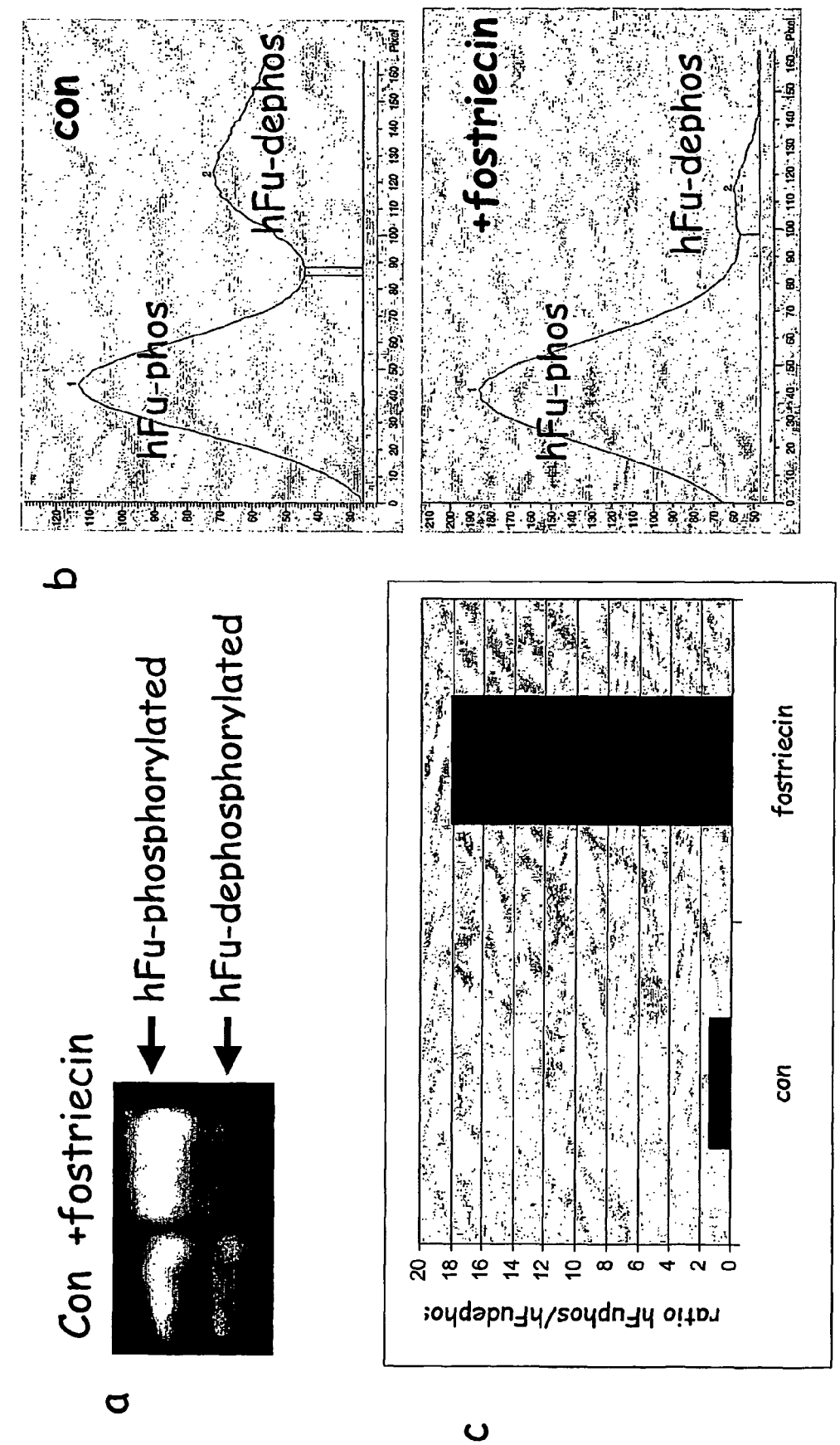

FIG. 14: -humanFused-Phosphorylation (hFused-Phosphorylation):

a: Cytosol of V5-tagged hFused-overexpressing cells was incubated for 4 h in the absence (line1) and presence (line2) of fostriecin at 30° C. Subsequently proteins were separated on an SDS-Page, blotted and incubated with an anti-V5 antibody. A clear enrichment of the phosphorylated hFused-band (upper band) is visible after fostriecin-incubation in comparison to the dephosphorylated band.

b: Image-quant-quantification of the Western-blot seen in a. In the control (incubation without fostriecin) the ration between phosphorylated and dephosphorylated hFused differs clearly from the fostriecin treated sample.

c: Ratios between phosphorylated and dephosphorylated hFused-form shows a 1.8× difference in the control (incubation without fostriecin), while a difference of 18× was measured after fostriecin-treatment.

Figure 15:
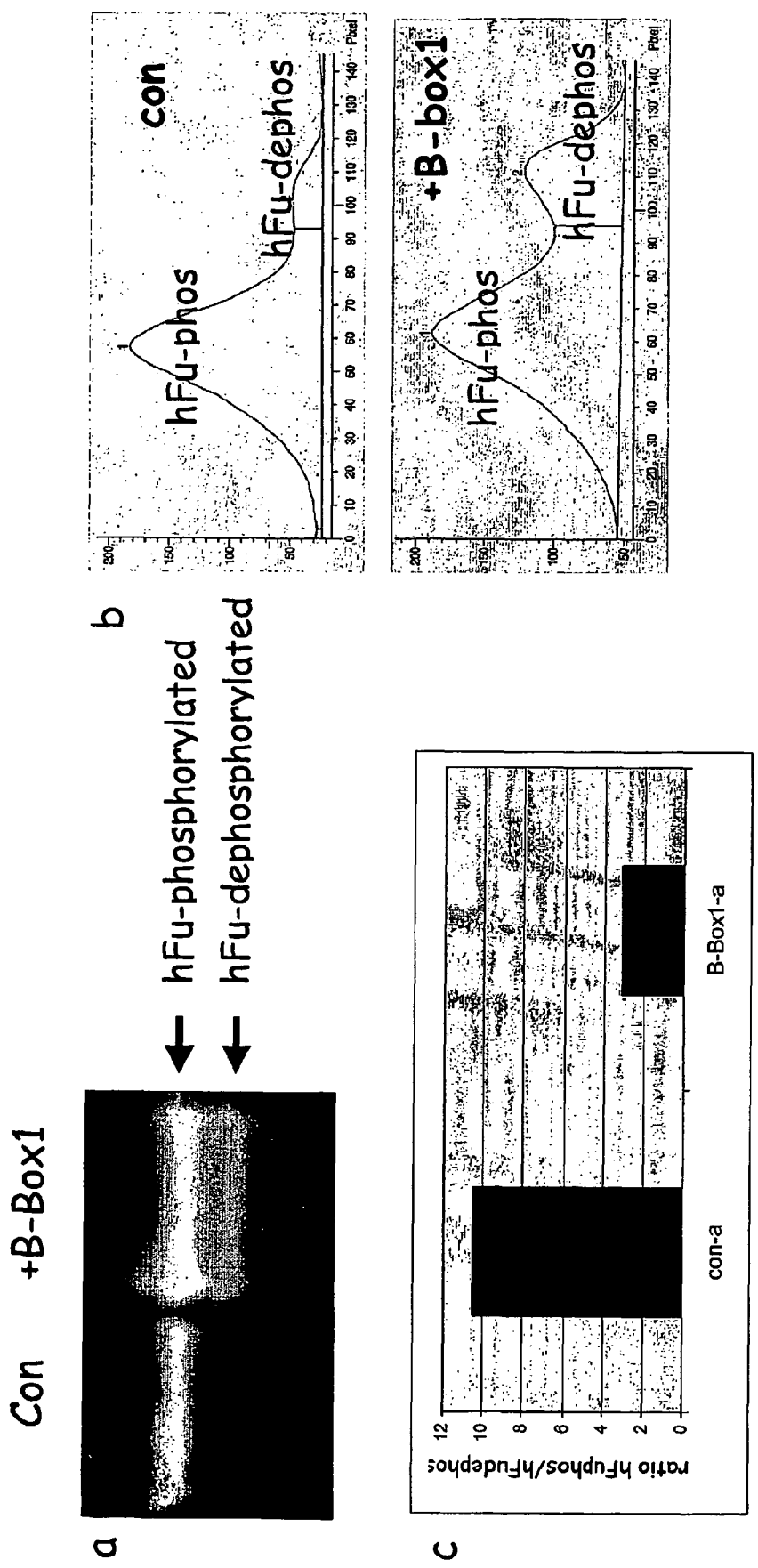

FIG. 15: -hFused-Phosphorylation:

a: Cell lysate of cells expressing only hFused (con) and hFused together with the B-Box1 (+B-Box1) was separated on an SDS-Page, blotted and incubated with an anti-V5-antibody. In order to stop all kinase and phosphatases directly after cell lysis, cells were lysed in an SDS- and urea-containing buffer. On the Western-blot a clear enrichment of the dephosphorylated hFused form can be detected in the cells co-expressing hFused and the B-Box1 compared to the control (expressing only hFused).

b: Image-quant analysis of the Western-blot shown in a. The ratio between phosphorylated and dephosphorylated form of hFused in the control differs clearly from the ratio detected in the cells co-expressing hFused and the B-Box1.

c: The ratio between phosphorylated and dephosphorylated hFused-form in the control (con-a, cells only overexpressing hFused) is 10.3, while the ratio between phosphorylated and dephosphorylated hFused-form in the cells co-expressing the hFused and the B-Box1 is 3.

FIG. 16: -hfused Phosphorylation:

Reproduction of the experiment of FIG. 15.

c: The ratio between phosphorylated and dephosphorylated hFused-form in the control (con-a, cells only overexpressing hFused) is 8.3, while the ratio between phosphorylated and dephosphorylated hFused-form in the cells co-expressing the hFused and the B-Box1 is 3.

METHODS

Yeast two-hybrid screening. For yeast two-hybrid screening, we cloned full-length MID1 cDNA into the pBTM116 vector. We then cotransfected this with a human fetal brain cDNA Matchmaker library in the pGAD10 vector (Clontech) into the L40 yeast strain. We plated the transformants on synthetic medium lacking histidine, leucine and tryptophan (his⁻ leu⁻ trp⁻) and containing 3-amino-1,2,4, triazole, and incubated the plates at 30° C. for 5 days. We assayed his-positive colonies for β-galactosidase activity with a filter assay[47]. We isolated plasmid DNA from β-galactosidase-positive clones and cotransfected this again into L40 yeast with MID1-pBTM116 and controls. We selected plasmids that produced growth on selective plates only in combination with MID1-pBTM116, which were assumed to code for MID1 interactors, and sequenced them.

Activity of β-galactosidase in yeast liquid cultures. We assayed cells for β-galactosidase activity by the o-nitrophenyl-β-D-galactopyranoside (ONPG) method[47].

Tissue culture. We obtained embryonic fibroblasts from the Max-Planck Institute for Cell Biology (Ladenburg, Germany) and purchased COS7 cells from the American Type Culture Collection (ATCC). Establishment of an embryonic fibroblast cell line from an OS-affected fetus has been described previously[4]. We transfected COS7 cells following the Clontech protocol using LipofectACE. Expression was optimal 24-48 h after transfection. We lysed cells in IP1 buffer (150 mM NaCl, 10 mM Tris, 1% Nonidet P-40 (NP-40), pH 7.0) or in RIPA buffer (1×PBS, 1% NP-40, 0.5% sodium deoxycholate, 0.1% SDS) plus inhibitors (Roche) and subsequently cleared the lysates by sequential centrifugation (at 17,500 g and then 100,000 g). We established stably expressing cell lines using the Clontech Tet-off system. We determined integration copy number by Southern blot analysis. We transfected embryonic fibroblasts in a Bio-Rad Gene Pulser at 200 V and 125 µFd.

For proteasome inhibition, we incubated embryonic fibroblasts with varying concentrations (10-50 µM) of LLnL (Sigma) for 2 h or with 10 µM of lactacystin (Sigma) for 5 h. Subcellular fractions of $1.6 \times 10^7$ primary embryonic fibroblasts (from cells lines derived from an individual with OS and from an age-matched control) were prepared as described[47] based on three differential centrifugation steps (1,000 g, 17,500 g, and 100,000 g). Protein concentrations were determined with a Bradford assay.

Constructs. For stable genomic integration of the MID1-V5 cDNA, we cloned the MID1 cDNA (open reading frame) into the pcDNA4.1-V5-HIS vector (Invitrogen) and subsequently reamplified it with the V5-HIS tag. We then cloned the fusion construct cloned into the pTRE vector (Clontech). We used pBudCE4 vector (Invitrogen) to simultaneously express two proteins from a single vector. We cloned the MID1 cDNA into the $P_{CMV}$ promoter multiple cloning site using HindIII and SalI, and ligated MID1, α4 and PKC cDNAs to the $P_{EF-1\alpha}$ promoter multiple cloning site using NotI and BglI. We expressed GFP-MID1 as described[4]. We expressed the α4 protein C-terminally tagged to the myc peptide from the pCMV-Tag3 vector (Stratagene). For the MACS, we cloned MID1 into a pMACS $K^k$.II vector using EcoRI and SalI.

Cell sorting. Starting with $2 \times 10^7$ embryonic fibroblasts transfected with the pMACS $K^k$.II, we carried out cell sorting using a MidiMACS separation unit and MACSelect Kk Microbeads according to the manufacturer's instructions.

Immunoprecipitation, western blotting and immunofluorescence. For COS7 cells, we lysed in IP1 buffer $8 \times 10^6$ cells transfected with pBudCE4 vector carrying the respective cDNAs. After preclearing the lysate with 50 µl protein A-agarose (slurry), we incubated supernatants with 2 µg anti-V5 overnight at 4° C. and then for 2 h with 75 µl (slurry) protein A-agarose. After three washes in IP1 buffer, we eluted the proteins with 1× Laemmli buffer at 95° C. MID1-V5 expression was optimal 48 h after doxycyclin removal from 293 tet-off cell lines. We then lysed cells in IP1 buffer and carried out immunoprecipitation with 2 µg anti-V5. We boiled proteins in 1×SDS-PAGE buffer, separated them on 10% and 12% SDS gels, blotted on PVDF membranes (Roche) and blocked and incubated with the respective primary antibody according to the manufacturer's instructions.

For embryonic fibroblasts, we lysed $8 \times 10^6$ cells in IP1 buffer. After preclearing the lysate with 50 µl protein G-agarose, we incubated supernatants with 2 µg of monoclonal anti-ubiquitin overnight at 4° C. and then with 75 µl (slurry) protein G-agarose for 2 h also at 4° C. We carried out elution and protein analysis as described above. We carried out densitometric quantification using the PCB computer program.

We grew $1.5 \times 10^5$ COS7 cells on coverslips, transfected them with the respective vector and fixed them with 4% paraformaldehyde in PEM buffer. We carried out antibody incubations following standard procedures.

Antibodies. We purchased polyclonal anti-PP2Ac from Calbiochem, anti-phosphoserine and anti-phosphothreonine from Biomol, monoclonal anti-V5 from Invitrogen, monoclonal anti-c-myc from Clontech, anti-ubiquitin from Santa Cruz Biotechnology and anti-actin from Sigma. We visualized anti-MID1 as described[3]. We tested antibody specificity by preincubating the blots with intestine alkaline phosphatase (200 U/ml; Gibco-BRL).

We prepared polyclonal antiserum to α4 by immunizing two rabbits with the peptide AAEDELQLPRLPELFET-GRQLLDEVEVATEPAGSRIVQEKC derived from the protein's N-terminus. After four boosts at 3-wk intervals, we collected high-titer serum at 12 wk after immunization. We purified the antibody by affinity chromatography on immobilized peptide coupled to Sulfolink coupling gel (Pierce). The antibody recognizes a specific band of approximately 40 kD which was specifically suppressed by addition of antigenic peptide. We used the affinity-purified antibody at a 1:100 dilution for western blots.

In vitro assembly of microtubules. We carried out microtubule assembly as described previously[4]. Briefly, we lysed $1.6 \times 10^7$ embryonic fibroblasts in microtubule assembly buffer (0.1 mM PIPES, pH 6.8, 1 mM $MgSO_4$, 2 mM EGTA, 2 mM DTT, 0.1 mM GTP) and cleared the lysate by ultracentrifugation (1 h at 60,000 g, 4° C.). We then incubated the supernatant with GTP and taxol at 37° C. for 30 min and centrifuged it for 30 min at 40,000 g, 37° C. We washed the pellet once with assembly buffer containing taxol and redissolved the microtubules in assembly buffer without taxol at 4° C.

Two-dimensional western blotting. We carried out two-dimensional electrophoresis by the ampholyte method as follows[48]: we mixed 20 mg urea (9 M final), 1.4 μl of 1 M DTT (70 mM final) and 2 μl of ampholytes, pH 2-4, with 20 μl of immunoprecipitated proteins resuspended in IP1 buffer. We degassed samples for 5 min before loading. We used gel solution prepared exactly as described[49] and polymerized gels in 0.9 mm-wide 2D tubes (Bio-Rad). We loaded the degassed samples directly on the polymerized gels and overlaid them with 25 μl sample protection solution[49]. We carried out isoelectric focusing with the following gradient: 45 min at 100 V, 1 h at 200 V, 1 h at 400 V, 1 h at 600 V, 10 min at 800 V and 5 min at 1,000 V. We then equilibrated the gels for 10 min in equilibration solution[39], layered on 0.98 mm-thick 10% SDS minigels (Bio-Rad) and overlaid 1% agarose in agarose buffer[49]. We equilibrated and blotted the second-dimension gels according to standard procedures in a semi-dry blotter (Bio-Rad) for 30 min at 15 V, and then carried out antibody incubations as detailed above.

Cell Culture

Peripheral sympathetic neurons were obtained from postnatal day 1-3 rats. Superior cervical ganglia (SCG) were dissected and treated with 0.25% trypsin for 20 minutes at 37° C. Following mechanical dissociation the cell suspension was filtered through a 40 μm nylon mesh and seeded at 6 SCGs per well into uncoated Falcon dishes for preplating purposes. After 4 hours neurons were transferred into glass floor dishes (Willco Wells B.V., gwst 3522, 3.8 cm² area/dish) coated with poly-D-lysine/laminin. Neurons were maintained in RPMI medium containing antibiotics, N2 additive (Invitrogen) and 100 ng/ml nerve growth factor (NGF; Sigma) at 37° C. in a humidified atmosphere with 5% $CO_2$.

Neuronal Transfection

Neurons were transfected 2 hours after seeding applying the biolistic approach. This method uses a hand held gun to bombard dissociated neurons at high velocity with micron-size gold particles loaded with DNA. The coating of gold particles with DNA was achieved using a modification of the manufacturer's instructions (Bio-Rad Laboratories). For preparation of 35 cartridges 25 mg gold particles (1.6 μm diameter) were suspended in 50 μl of 0.05 M spermidine. After vortexing and sonication for 5 seconds, 50 μg plasmid DNA dissolved in 50 μl TE buffer was added (for co-transfection experiments, 80 μg were used, i.e., 40 μg Plasmid I+40 μg Plasmid 2). The amount of gold particles and DNA corresponds to a microcarrier loading quantity (MLQ) of about 0.7 (mg/cartridge) and to a DNA loading ratio (DLR) of 2 (μg/mg) for single transfection experiments. DNA, spermidine and gold were then mixed for 5 sec in a variable speed vortexer. At low vortexing speed, 50 μl 1 M $CaCl_2$ was added dropwise to the mixture for association of DNA with the gold particles followed by precipitation for 10 min at room temperature. The supernatant was removed and the pellet rinsed with 800 μl of 100% ethanol. Washing was repeated two times with centrifugation steps at 3000 g between each wash. Finally, the pellet was resuspended in 500 μl PVP solution (0.05 mg polyvinylpyrrolidone in 100% ethanol) and transferred to a 15 ml Falcon tube containing 2 ml PVP solution. The gold particles were loaded into special Tefzel tubing (Bio-Rad) which was dried for at least 15 min prior to loading using nitrogen gas. The microcarrier/DNA suspension was vortexed for 10 sec and drawn into the tubing applying a 10 cc syringe. The gold particles were allowed to settle for 3 min. After the ethanol was removed from the tubing, the tubing was rotated for 5 min under constant nitrogen flow in order to coat the inside surface of the tubing with particles. The tubing was cut into small pieces (cartridges) using a cutting device provided by Bio-Rad and stored in a desiccated environment at 4° C.

For neuronal transfection, the medium was aspirated, the barrel liner of the gun was placed directly above the dish and the gold particles were accelerated using inert helium gas (120 psi pressure). In order to limit the damage induced by the shock wave and to obtain a uniform particle distribution, a 40 μm nylon mesh was placed between the barrel liner of the gene gun and the culture dish.

Immunofluorescence

Two days after transfection cell cultures were fixed with 4% paraformaldehyde for 10 min at 4° C., followed by permeabilization with 0.5% Triton X-100 in PBS for 5 min. Primary antibodies against human tau (mouse monoclonal, 1:50, upstate) or against the hypophosphorylated form of Tau (mouse monoclonal, 1:100) were dissolved in PBS containing 0.3% bovine serum albumin (BSA) and added to the cultures for 2 hours at 37° C. After three washes in PBS the neurons were incubated with Cy3-conjugated goat anti-mouse IgGs (Dianova, Hamburg, Germany) for 1 hour at room temperature with another three subsequent washes in PBS.

Microscopy and Morphometrical Analysis

A fully motorized Zeiss Axiovert 100M microscope equipped for inverted fluorescence was used for visualization of fluorescent neurons. Appropriate filter sets with mutually exclusive excitation/emission characteristics were obtained from Chroma (#41017 for EGFP, #41002C for Cy3). The whole dish was systematically screened for fluorescent cells and all transfected neurons were documented at identical exposure times for each experiment. Images were taken at 40× magnification using a digital camera (Spot RT) connected to a PC and analyzed with Metamorph™ software (version 4.5r5, Visitron Systems, Munich, Germany). The average immunofluorescence intensity of non-transfected and transfected neurons in each image was determined using a circular region placed randomly over the cytoplasm. Three measurements were performed over each intact neuronal cell body and the mean±standard error of the mean (S.E.M.) determined (maximal intensity=256). Fluorescence intensities of transfected neurons were normalized against the average fluorescence intensity of all non-transfected neurons (=100%) incubated with one of the different Tau antibodies in each experiment.

Cloning

The MID1 Bbox1 (amino acids 108-165) were cloned into the EcoRI and SalI restriction sites of pIRES2-EGFP (Clontech); the respective DNA-fragment was generated with PCR from the human MID1-cDNA using the following oligodesoxynucleotide primers:

```
5':    TCGAATTCGCAATGGCCAACACCATGACCTCCGCC

3':    ACCGTCGACTCAAATTGGCTCAATCAGACGATGG
```

The MID1 Bbox-mutated was cloned analogously using a MID1-cDNA with an exchange of alanine 130 to a threonine (codon change: GCT to ACT) as PCR-template. This mutation was found in an Opitz patient with the full spectrum of the disease and was shown to abolish the normal association of the Bbox1 of MID1 with the α4 protein (unpublished observations).

The following examples are provided to illustrate the present invention, and are not to be construed to be limiting thereof. In particular, it will be understood that the peptidic or proteinaceous compounds or the compounds derived therefrom which are to be formulated as a pharmaceutical in the treatment of the aforementioned diseases may be modified on the basis of the teachings of the present invention without loosing their pharmaceutical activity. These modifications and variations to the examples are to be regarded as being within the spirit and the scope of the present invention.

Methods Gli3-Experiments:

COS7-HELA- and U373MG-cells were transfected using PolyFect Transfection Reagent (Qiagen, cat. no. 301107) according to the manufacturer's instructions. Gli3 cDNA was cloned into pEGFP-C1 and pEGFP-N3 vectors (Clontech) respectively. 100 transfected cells per experiment (Gli3-GFP, GFP-Gli3, Gli3-GFP+myc-MID1, GFP-Gli3+myc-MID1, Gli3-GFP+myc-BBox1, GFP-Gli3+myc-BBox1) were counted and analysed for Gli3 localization. Experiments were repeated twice. A significant change from the nucleus to the cytosol of both, GFP-Gli3 and Gli3-GFP was observed when cotransfected with BBox1. PCMV-Tag3 vector from Stratagene was used for myc-MID1 and myc-BBox1 overexpression.

Immunofluorescence II:

$1 \times 10^5$ HELA cells per well of a 6-well plate were transfected with Qiagen Polyfect transfection reagent according to the manufacturer's instructions. The ratio of the amount of DNA to the amount of polyfect transfection reagent was 3 µg DNA/10 µl Polyfect. Constructs used for expression in HELA were the following: GFP-GLI3 (aa 18-1549), GLI3-GFP (aa 1-1522), MYC-GLI3 (aa 18-1596), FLAG-GLI3 (aa18-1596), MYC-B-BOX1 (aa 110-167 of the MID1 protein), ALPHA4-V5 (aa 1-339). 24 h after transfection immunofluorescence was performed. GFP-constructs were treated as described in Schweiger et al., 1999. Immunofluorescence with MYC-tagged and FLAG-tagged constructs was done according to Trockenbacher et al., 2001. FLAG-tagged constructs were detected with anti-FLAG-antibody diluted 1:500, the secondary antibody FITC-antimouse was diluted 1:1000. For MYC-tagged constructs anti-MYC-antibody 1:300 and CY3-antirabbit 1:1000 were used.

Western Blot and In-Vitro Incubation with Fostriecin $8 \times 10^5$ cells were transfected with hFused-V5 (aa 1-1335) using Qiagen Polyfect transfection reagent according to the manufacturer's instructions. Cytosol of hFused-V5 overexpressing cells was incubated for 4 h in the presence or absence of fostriecin (500 nM) at 30° C. Proteins (200 µg protein per lane) were separated on a 6% SDS-gel, blotted on PVDF-membranes and incubated with anti-V5-antibody (1:3000). Secondary HRP-antimouse-antibody was diluted 1:2000.

Western Blot hFused Phosphorylation $8 \times 10^5$ cells were transfected with hFused-V5 (aa 1-1335) in presence and absence of MYC-B-BOX1 (aa 110-167 of the MID1 protein) using Qiagen polyfect transfection reagent according to the manufacturer's instructions. Cell pellets were resuspended in magic mix (48% urea, 15 mM Tris-HCl, 8.7% glycerin, 1% SDS, 0.004% Bromphenol Blue, 143 mM β-Mercaptoethanol). After sonification, cell lysate of cells expressing hFused and hFused together with B-Box1 was separated on a 6% SDS-gel (200 µg protein loaded in each lane), blotted on PVDF-membranes and incubated with anti-V5-antibody (1:3000). Secondary HRP-antimouse-antibody was diluted 1:2000.

Alpha4 Knockdown $5 \times 10^4$ HeLa cells per well of a 6-well plate were transfected with 2.6 µg of synthetic siRNA (Dharmacon) per well using Oligofectamine (Invitrogen) according to the manufacturer's instructions. Sequences of siRNAs targeting alpha4 mRNA were GUACCUUUUG-GUGCCAGCGdTdT (sense) and CGCUGGCAC-CAAAAGGUACdTdT (antisense). The last two nucleotides at the 3' end of each single siRNA were desoxythymidines (dT). For control experiments we used the previously published siRNA targeting Lamin A/C (Elbashir et al.) and a non-targeting control siRNA (Xeragon) with the sequences UUCUCCGAACGUGUCACGUdTdT (sense) and ACGUGACACGUUCGGAGAAdTdT (antisense) which were transfected as described above. Transfection efficiency was monitored with FITC-labeled control-siRNA (Xeragon). Approximately 95% of the cells showed siRNA uptake, visible under a conventional fluorescence microscope.

24 h after transfection with siRNA, cells were transfected with GFP-GLI3 using Qiagen Polyfect transfection reagent according to the manufacturer's instructions. Immunofluorescence was performed as described in Schweiger et al., 1999.

To proof the alpha4 knockdown 20 µg of total protein were separated by SDS-PAGE (10%), blotted on PVDF membranes (Roche). Membranes were incubated with a rabbit polyclonal anti-alpha4 antibody (1:300 dilution). Secondary HRP-antirabbit-antibody was diluted 1:2000.

EXAMPLES

Example 1

Polyubiquitinated Proteins Accumulate in the MID1 Immune Complex

Because several RING-finger proteins interact with target proteins and thereby elicit their ubiquitin-dependent degradation[8-11], we examined interaction of MID1 with polyubiquitinated proteins. We transfected COS7 cells either with MID1 cDNA or, as a control, with cDNA encoding protein kinase C (PKC), each tagged with a C-terminal V5 epitope or an empty vector, respectively. We treated the cells with 25 µM of LLnL, a proteasome inhibitor, 24 h after transfection to enrich for ubiquitinated proteins. We precipitated cellular extracts with anti-V5 and carried out SDS-PAGE and western blotting with anti-ubiquitin. The MID1-containing precipitate from cells pretreated with the proteasome inhibitor contains copious amounts of proteins ubiquitinated to varying degrees, visible upon immunoblotting as high-molecular weight protein smear (FIG. 1a, lane 6). This protein smear is not seen in precipitates from mock-transfected cells or from cells expressing V5-tagged PKC (FIG. 1a, lanes 14).

We corroborated this result by treating MID1-myc-overexpressing and mock-transfected cells with a second inhibitor, the 20S proteasome-specific inhibitor lactacystin[14]. Again, we detected an enrichment of high-molecular weight proteins in the MID1-myc-containing precipitates after lactacystin incubation but not in the mock-transfected cells (FIG. 1b).

Example 2

MID1 Interacts with α4, a Regulatory Subunit of PP2A

To identify targets for MID1-mediated protein ubiquitination, we used the full-length MID1 protein-coding region as bait in a yeast two-hybrid screen of 106 colonies of a human fetal brain library. We obtained four independent positive clones (a-d) that contained two inserts of different lengths. All clones contain sequences corresponding to the human IGBP1 gene, which encodes α4—a protein previously shown to bind PP2A[12,15,16]. Clones a and b encode the 168 amino acids (aa) at the C-terminal end, whereas clones c and d contain an N-terminal sequence. After codon 290, this sequence is interrupted by an intron leading to premature termination of translation after 17 additional aa unrelated to α4. Thus, the α4 protein domain that interacts with MID1 maps to the 119 aa common to both types of clones, spanning residues 172-290 (FIG. 2a). FIG. 2c shows the specificity of the MID1-α4 interaction. Of the other proteins tested in the two-hybrid assays, only MID2 (ref. 17), which is highly similar in amino acid sequence (83%) to MID1, also binds α4, whereas three other RING-finger proteins, RBCC728 (ref. 18), HHARI (ref. 19) and PARKIN (ref. 10), do not.

Example 3

Mapping of the α4 Binding Site on MID1

MID1 is a multidomain protein harboring a RING finger, two B-boxes, a coiled-coil region, a fibronectin type III domain and a B30.2 domain[3]—all of which are candidate regions for specific protein-protein interactions. To clarify which domain specifically binds α4, we tested several deletion mutants of MID1 for interaction with α4 in the yeast two-hybrid system. The results show that B-box 1 (residues 110-165) is sufficient for a strong interaction with α4 (FIG. 2b). Indeed, longer constructs including other domains bind less strongly to α4 (FIG. 2a, b).

Example 4

MID1 Colocalizes with α4 in Intact Cells

We next examined the localization of MID1 and α4 in intact cells by overexpressing green fluorescent protein (GFP)-tagged MID1 (ref. 4) and N-terminally myc-tagged α4 in COS7 cells. When expressed alone, α4 exhibits a diffuse cytoplasmic distribution (FIG. 3a). Co-expression of both proteins makes α4 colocalize with wildtype GFP-MID1 protein, leading to a 100% overlap along cytoskeletal structures (FIG. 3b). Expression of a mutant GFP-MID1 carrying a mutation in the C-terminus, mimicking the situation in individuals with OS, results in the formation of cytoplasmic clumps containing both proteins (FIG. 3c).

Example 5

MID1 Immunoprecipitates with α4

We used immunoprecipitation as an independent method to confirm the observed protein interaction. We overexpressed MID1 and α4 cDNAs in COS7 cells using a single vector expressing both proteins from two different promoters. For signal detection in subsequent western-blot and immunoprecipitation experiments, MID1 carried a C-terminal myc tag (MID1-myc) whereas α4 was fused to a C-terminal V5 tag (α4-V5). Western blotting of transfected lysates yielded bands at the expected sizes (75 kD for MID1-myc, 45 kD for α4-V5; data not shown). We then precipitated lysates of α4-V5- and MID1-myc-expressing cells with anti-myc and anti-V5. Western-blot analysis of the precipitate with the respective complementary antibodies showed that MID1 coprecipitates with V5-tagged α4 (FIG. 3d, lane 2; FIG. 3e, lane 3). In addition, immunoprecipitation of cells expressing both myc-tagged and V5-tagged MID1 with anti-V5 and subsequent western-blot analysis using anti-myc produced a specific MID1 band of 75 kD (FIG. 3d, lane 3), confirming a previous observation that MID1 is able to form homodimers[20]. Anti-V5 precipitates from cells expressing only MID1-myc did not show a specific MID1 size (FIG. 3d, lane 1). In contrast, an antibody detecting endogenous α4 protein confirmed that MID1-myc and endogenous α4 protein coprecipitate (FIG. 3e, lane 5). Thus, co-expression of MID1-myc and α4-V5 proteins leads to replacement of endogenous α4 from the MID1 binding sites by overexpressed α4-V5 (FIG. 3e, lane 4).

To identify more precisely the MID1 protein domain responsible for α4 binding and to confirm our results from the yeast two-hybrid experiments, we co-expressed V5-tagged α4 with the myc-tagged RB domain (RING finger and two B-boxes) and with the myc-tagged B-box 1 of the MID1 protein, respectively. Precipitation with anti-myc and subsequent western blotting with anti-α4 showed a strong interaction of α4 (V5-tagged and endogenous) with both the RB domain (FIG. 3e, lane 1) and the first B-box (FIG. 3e, lane 2). In the reverse experiment—that is, precipitation of V5-tagged α4—we detected the myc-tagged RB domain on a western blot (FIG. 3d, lane 4). We could not resolve the B-box 1-containing polypeptide with the electrophoretic conditions used, probably because of its very low molecular weight (5 kD).

Example 6

MID1-Dependent Ubiquitination of PP2A

The observed ubiquitin ligase activity of the MID1 protein and its specific interaction with α4 led us to search for ubiquitin-specific degradation of α4. Cytosolic extracts of embryonic fibroblasts did not show any enrichment of α4 after pretreatment with LLnL, nor was there evidence for ubiquitin-specific modification of α4 (data not shown). Likewise, similar experiments using a specific anti-MID1 for western-blot analysis did not show evidence for ubiquitin-specific modification of the MID1 protein (data not shown).

Given that α4 has been shown to function as a regulatory subunit of PP2A[15], it is tempting to speculate that this enzyme is a target for MID-α4 ubiquitin ligase activity. If so, increased MID1 expression should coincide with a decrease of cytosolic PP2A. To test this hypothesis, we analyzed lysates containing equal amounts of protein from 293 cells expressing MID1-V5 (FIG. 4a, lane 1) and control cells (FIG. 4a, lane 3) by western blotting with a polyclonal antibody that detects the C subunit of PP2A. The results showed that cytosolic phosphatase 2A is indeed downregulated in MID1-V5 expressing cells. Pretreatment with the proteasome inhibitor LLnL (FIG. 4a, lane 2) completely blocks this PP2A downregulation, indicating that ubiquitin-dependent degradation is responsible for the effect.

To obtain direct evidence for ubiquitin-dependent regulation of cytosolic PP2A, we analyzed amounts of cytosolic PP2A in embryonic fibroblasts, previously shown to contain large amounts of endogenous MID1 (ref. 2), after treatment with the proteasome inhibitor LLnL (FIG. 4b). Increasing concentrations of LLnL lead to an enrichment of PP2A (FIG. 4b, middle panel) and polyubiquitinated forms of the enzyme (FIG. 4b, upper panel), as would be expected for a protein regulated by ubiquitin modification. By contrast, addition of LLnL to OS-derived fibroblasts expressing dysfunctional MID1 (as discussed above) does not cause either enrichment of PP2A or accumulation of the enzyme's polyubiquitinated forms (FIG. 4c). This indicates that in individuals with OS, MID1 mutations result in decreased proteolysis of the C subunit of PP2A.

Example 7

Rescue of PP2Ac Degradation in OS-Derived Cells by Overexpression of MID1

These findings were confirmed by transfection of the control cell line with mutant MID1, which eradicates ubiquitin-specific degradation of PP2Ac (FIG. 4d), indicating that large amounts of mutant MID1 protein have a dominant negative effect. Transfection of OS-derived cells with wildtype MID1 normalizes the amount of PP2Ac, however, by restoring ubiquitin-mediated protein turnover (FIG. 4e).

To further confirm ubiquitination of PP2Ac, we immunoprecipitated cytosolic extracts of either control or OS-derived cells with anti-ubiquitin. Detection with anti-PP2Ac yields a specific band at 44 kD, the expected size of mono-ubiquitinated PP2Ac in the control cell line. This band is enriched after pretreatment with LLnL (FIG. 4f). In contrast, no clear band of the same size can be seen in the corresponding precipitate of the OS-derived individual's cells (FIG. 4O.

Example 8

Upregulation of Microtubule-Associated PP2A in OS-Derived Cells

Given that mutant MID1 accumulates in OS-derived embryonic fibroblasts, we decided to use these cells to test whether MID1 affects the amounts of endogenous PP2A. We carried out a series of cell fractionation experiments using the OS-derived embryonic fibroblast cell line and an age-matched control cell line. We found that the PP2A concentration is increased in the cytosolic fraction of OS-derived cells (FIG. 5a, S3), by a factor of 2.6 as quantified by densitometric analysis (FIG. 5c), but it is not increased in other cell fractions (FIG. 5c, P1-P3). To further characterize PP2A subfractions, we purified microtubules from both cell lines, separated equal amounts (2 μg) by SDS-PAGE and carried out western blotting to detect PP2Ac (FIG. 5b). The difference in PP2A expression between OS-derived and control cells (ratio 4.4, FIG. 5c) was even more pronounced in these subfractions than in the cytosol. Thus defective turnover of microtubule-associated PP2A in OS-derived cells seems to be largely responsible for the observed differences in amounts of cytosolic enzyme.

Example 9

Altered Protein Phosphorylation in OS-Derived Cells

Finally, we investigated biological consequences of the increased PP2A expression detected in the OS-derived fibroblasts. Elevated PP2A should result in altered phosphorylation of target proteins. To study protein phosphorylation patterns, we separated purified microtubules from cells of the OS-derived fibroblast cell line and three different age-matched control cell lines by two-dimensional PAGE and carried out western blotting with a combination of anti-phosphoserine and anti-phosphothreonine. The OS-derived fibroblasts show a marked overall hypophosphorylation of microtubule-associated proteins (FIG. 6). We verified the specificity of this observation and of the antibodies by pretreatment with alkaline phosphatase, which results in the disappearance of all relevant spots.

Example 10

Dominant Negative Effect on the Degradation of PP2Ac

While we with foregoing examples demonstrated that ubiquitin specific degradation of PP2Ac can be influenced by ectopic expression of mutant MID1 protein in embryonic fibroblasts (Trockenbacher et al., 2001), we now demonstrate that introduction of isolated B-box1 in eukaryotic cell systems results in a pronounced dominant negative effect on the degradation of PP2Ac. First, yeast-two hybrid experiments comparing the α4-affinities of MID1 peptides showed that the affinity of isolated B-Box1 increases by a factor of 10 compared to the full length MID1 protein (Trockenbacher et al., 2001), thus predicting a pronounced dominant negative effect on the full-length MID1-α4 interaction in cells. This prompted us to analyse the effect of PP2Ac, accumulated by overexpression of the isolated Bbox1, on a specific target protein, namely the transcription factor Gli3. Gli3 is mutated in an inherited human disease, namely the Greig cephalopolysyntactyly syndrome, which presents a phenotype intriguously overlapping with the Opitz-syndrome phenotype suggesting that similar pathways are affected. Gli3 is a transcription factor homologous to the *Drosophila* protein cubitus interruptus that is involved in the hedgehog signalling pathway (Shin et al., 1999), which controls cell proliferation and cell fate specification. Gli3 is normally sequestered in the cytoplasm by indirect anchoring to the microtubular apparatus. Interestingly, in the absence of hedgehog-signalling this Gli3 is phosphorylated and subsequently processed and translocated to the nucleus, were it represses the transcription of specific target genes. Given the microtubule association of Gli3 and the fact that increased levels of PP2Ac have been shown to mimic active hedgehog-signalling (Krishnan et al., 1997), we wanted to analyse the effects of elevation of PP2ac through Bbox1 overexpression on the localization of full-length Gli3. In immunofluorescence studies detecting intracellular Gli3 in U373MG cells we could indeed find a significant Bbox1-dependent change of Gli3 localization clearly symbolizing an increase of PP2A activity after overexpression of isolated B-Box1 (FIG. 8). No change was detected in cells overexpressing wildtype MID1 protein.

These data show that not only PP2Ac levels but also PP2Ac dependent modification of target proteins can be influenced by blocking the described mechanism. Our results with Gli3, which is a central target gene of the hedgehog pathway, also point, due to the known pathways influenced by Gli3, at an important role of microtubules associated PP2Ac in bone development and osteoporosis.

Example 11

PP2Ac Activity and Implications with Alzheimer

PP2Ac activity has also important implications with Alzheimer disease, which has been shown to be one of the most frequent neurodegenerative disorders (Trojanowski and Lee, 1995). Intra (paired helical filaments)- and extracellular (beta amyloid) plaques have been found in brains of Alzheimer disease patients. While varied interactions between the two kinds of plaques have been found the pathognomonic event of Alzheimer disease is still under discussion (Maccioni et al., 2001). However, hyperphosphorylation of the tau protein, which is a neuron specific microtubules associated protein, has been shown to result in a release of tau from the microtubules and in the formation of intracellular plaques. Transgenic mice that overexpress different variants of tau and also show intracellular plaques consisting of hyperphosphorylated tau protein interestingly present with a phenotype that highly overlaps with the phenotype of Alzheimer disease patients (Richardson and Burns, 2002). From these mice one can conclude that the occurrence of intracellular plaques is a decisive phenomenon for the development of Alzheimer disease. Moreover it has been shown that these intracellular tau-plaques can induce extracellular plaque formation. Recent reports have shown that the mentioned hyperphosphorylation of tau is based on serine-threonine phosphorylation and can be influenced by the serine-threonine phosphatase 2A and it has been shown that in vitro intracellular tau-plaques can even be dissociated by treatment with PP2A (Iqbal et al., 2000). And as tau has recently been reported to be essential to beta-amyloid-induced neurotoxicity (Rapoport et al., 2002) an elevation of PP2A in the cell over physiological levels has broad implications for prophylactic as well as therapeutic treatments of Alzheimer disease. Since PP2A is a cellular master regulator, its levels and activity are tightly regulated which makes overexpression practically impossible. We, for the first time could show that levels of a subfraction, namely microtubules associated PP2Ac can be substantially raised by inhibiting the mechanism described above. It is worth mentioning that it is exactly this subfraction of PP2Ac that is necessary for dephosphorylation of microtubules associated tau. Different possibilities to interfere with this PP2Ac degradation are conceivable.

Given the dominant negative effect of overexpressed Bbox1 in U373MG cells we speculated that a similar overexpression in primary neurons could also lead to an accumulation of microtubule associated PP2Ac and could subsequently result in dephosphorylation of the tau protein. To analyse such an effect we used peripheral sympathetic neurons from postnatal day 1-3 rats. These neurons were transfected (using a "gene-gun" approach, Klimaschewski et al., 2002) with a high-expression vector that produces a bicystronic RNA coding for Bbox1 and EGFP. Transfected cells can then be easily identified by their EGFP fluorescence. Tau and dephosphorylated tau can be visualized by immunofluorescence using either pan-Tau or Tau1 antibodies, respectively (Tau1 recognizes specifically dephosphorylated tau). Comparing the Tau1 immunofluorescence intensifies of transfected versus non-transfected or mock-transfected cells revealed a pronounced increase in fluorescence in the Bbox1 expressing cells (FIG. 9). Additionally, an analogous experiment with a Bbox1 that carries a mutation that was recognized as being causative for OS and compromises the α4-Bbox1 interaction does not show this effect. Thus, we could show that overexpression of a peptide comprising the α4 binding site of the MID1 protein clearly leads to tau-dephosphorylation in primary neuron tissue cultures. It should be feasible to induce similar effects by application of other peptides either derived from the amino acid sequences of MID1 or of α4 as well as of other proteins interacting with the cellular MID1 complex and regulating MID1's ubiquitin ligase function. Preliminary data from deletion-studies with α4 indicate that a small part of α4 (44 amino acids) is sufficient to bind to Bbox1 and similar as in the case of Bbox1 the interaction as observed in the yeast two hybrid system is more than 10 times stronger than with full-length α4 and thus also a promising candidate for a potent dominant negative effector. These findings together with the determination of the 3D-structures of α4 and Bbox1 and their complex will enable us to use computer-modelling for the construction of molecules interfering with the α4-Bbox1 interaction. Other interfering substances could be detected by ultra high throughput screening for molecules that interfere with PP2A degradation by binding to components or regulators of the MID1 complex.

Example 12

Influence of PP2Ac on the Localization of the Transcription Factor Gli3

In order to show that the MID1-α4-PP2Ac complex and subsequent degradation of the PP2Ac is involved in oncogenic pathways, in particular in the sonic hedgehog signalling pathway, the localization of overexpressed GFP-tagged Gli3 in HeLa cells was analyzed (FIG. 10). Overexpressed Gli3 is predominantly localized in the nucleus (FIG. 10, top left).

Overexpression of the B-Box1 (FIG. 10, middle row left), a peptide derived from the MID1 domain that is responsible for α4 binding, as well as rapamycin-treatment (FIG. 10, bottom) and downregulation of α4 via RNAi of GFP-tagged Gli3-overexpressing HeLa cells (FIG. 10, top right) led to a significant retention of the active form of Gli3 in the cytosol. Treatment of the GFP-Gli3 plus B-Box overexpressing cells with the PP2A specific inhibitor fostriecin (FIG. 10, middle row right) could reverse the observed effect. Overexpression of α4 on the other hand led to a significant release of GFP-Gli3 to the nucleus (FIG. 12). All experiments were done with GFP tagged to the C- and the N-terminus of Gli3 as well as with the V5-antigene tagged to the Gli3 C- and N-terminus.

Thus, it could be demonstrated that the Gli3 localization depends on PP2A activity.

Example 13

Analysis of HeLa Cells for Gli3 Activity

One of the most important targets of the Gli3 transcription factor is the patched gene. In order to analyse HeLa cells for Gli3 activity after treatment with the different molecules, semiquantitative RT-PCR of cells overexpressing the B-Box1 and the α4 protein was carried out (FIG. 13). HeLa cells have previously been tested for Gli3-, Gli1 (another target of the Gli3 transcription factor) and patched-expression. As expected, B-Box1 expression (FIG. 13, lane2) leads to significant reduction of the patched message while α4 overexpression (FIG. 13, lane1) leads to an increased amount of PCR-product as compared to the mock-transfected cells (lane3):

Thus, it could be demonstrated that altered cellular distribution of Gli3, triggered by the accumulation of PP2Ac by inhibition of the alpha4/MID1 complex results in a diminished expression of a known Gli3 target gene, namely patched.

Example 14

Interference with the MID1/PP2A Complex Leads to Cell Arrest

In order to test specific interference with the MID1/PP2A complex for putative anticarcinogenic effects, HeLa cells were transfected with specific anti-α4 RNAi molecules (FIG. 11). Depending on the time of exposure, a dramatic decrease in the proliferation of these normally rapidly growing tumor cells was detected in the cells containing anti-α4 RNAi molecules than compared to mock-transfected cells and to cells treated with unspecific RNAi molecules.

BrdU-labelling and subsequent FACS-analysis revealed that the reduction of cell numbers resulted from G1-phase arrest rather than from increased apoptosis. In contrast, downregulation of the MID1 protein, for example via RNAi, resulted in a dramatic induction of apoptosis.

Thus, by interfering with the MID1/PP2A complex, at least two different anticarcinogenic mechanisms (cell arrest and apoptosis) could be induced.

Example 15 hFu is an In Vitro Target of PP2A

In order to show that hFused is a target of microtubules-associated PP2A (phosphatase 2A), hFused-phosphorylation in vitro in the presence and absence of fostriecin was analyzed (FIG. 14). Fostriecin is a highly specific inhibitor of PP2A activity.

Cytosol of V5-tagged hFused-overexpressing cells was incubated for 4 h in the absence (line1) and presence (line2) of fostriecin at 30° C. Subsequently proteins were separated on an SDS-Page, blotted and incubated with an anti-V5 antibody. A clear enrichment of the phosphorylated hFused-band (upper band) is visible after fostriecin-incubation in comparison to the dephosphorylated band (FIG. 14 a).

Image-quant-quantification of the Western-blot seen in a. In the control (incubation without fostriecin) the ration between phosphorylated and dephosphorylated hFused differs clearly from the fostriecin treated sample (FIG. 14b).

Ratios between phosphorylated and dephosphorylated hFused-form shows a 1.8× difference in the control (incubation without fostriecin), while a difference of 18× was measured after fostriecin-treatment (FIG. 14c)

These in-vitro-experiments clearly showed that hFused dephosphorylation can be inhibited in vitro by fostriecin and the hFused therefore is a target of PP2A.

Example 16

Overexpression of the B-Box1 Leads to Dephosphorylation of hFused

In order to show that hFused Phosphorylation can be modulated by interference with the MID1/PP2A complex, V5-tagged hFused was coexpressed with the B-Box1, that comprises the α4-binding site of the MID1 protein. A dominant-negative effect of the B-Box1-peptide leading to an inhibition of MID1/4 induced ubiquitination of microtubules-associated PP2A and resulting in a enrichment of microtubules-associated PP2A was shown previously.

Cell lysate of cells expressing only hFused (con) and hFused together with the B-Box1 (+B-Box1) was separated on an SDS-Page, blotted and incubated with an anti-V5-antibody. In order to stop all kinase and phosphatases directly after cell lysis, cells were lysed in an SDS- and urea-containing buffer. On the Western-blot a clear enrichment of the dephosphorylated hFused form can be detected in the cells co-expressing hFused and the B-Box1 compared to the control (expressing only hFused) (FIG. 15a)

Image-quant analysis of the Western-blot shown in a. The ratio between phosphorylated and dephosphorylated form of hFused in the control differed clearly from the ratio detected in the cells co-expressing hFused and the B-Box1 (FIG. 15b).

The ratio between phosphorylated and dephosphorylated hFused-form in the control (con-a, cells only overexpressing hFused) was 10.3, while the ratio between phosphorylated and dephosphorylated hFused-form in the cells co-expressing the hFused and the B-Box1 was 3 (FIG. 15c).

These results could be reproduced (FIG. 16).

The ratio between phosphorylated and dephosphorylated hFused-form in the control (con-a, cells only overexpressing hFused) was 8.3, while the ratio between phosphorylated and dephosphorylated hFused-form in the cells co-expressing the hFused and the B-Box1 was 3 (FIG. 16c).

REFERENCES

1. Robin, H. N., Opitz, J. M. & Muenke, M. Opitz G/BBB syndrome: clinical comparisons of families linked to Xp22 and 22q, a review of the literature. *Am. J. Med. Genet.* 62, 305-317 (1996).
2. Robin, H. N. et al. Opitz syndrome is genetically heterogenous, with one locus on Xp22, and a second locus on 22q11.2. *Nature Genet.* 11, 459-461 (1995).
3. Quaderi, N. A. et al. Opitz G/BBB syndrome, a defect of midline development, is due to mutations in a new RING finger gene on Xp22. *Nature Genet.* 17, 285-291 (1997).
4. Schweiger, S. et al. The Opitz syndrome gene product, MID1, associates with microtubules. *Proc. Natl Acad. Sci. USA* 96, 2794-2799 (1999).
5. Wu, L. C. et al. Identification of a RING protein that can interact in vivo with the BRCA1 gene product. *Nature Genet.* 14, 430-440 (1996).
6. Borden, K. L. B., Lally, J. M., Martin, S. R., O'Reilly, N. J., Solomon, E. & Freemont, P. S. In vivo and in vitro characterization of the B1 and B2 zinc-binding domains from the acute promyelocytic leukemia protooncoprotein PML. *Proc. Natl Acad. Sci. USA* 93, 1601-1606 (1996).
7. Dyck, J. A., Maul, G. G, Miller Jr., W. H., Chen, J. D., Kakizuka, A. & Evans R. M. A novel macromolecular structure is a target of the promyelocyte-retinoic acid receptor oncoprotein. *Cell* 76, 333-243 (1994).
8. Fang, S., Jensen, J. P., Ludwig, R. L., Vousden, K. H. & Weissman, A. M. Mdm2 is a RING finger-dependent ubiquitin protein ligase for itself and p 53. *J. Biol. Chem.* 275, 8945-8951 (2000).
9. Fang, D., Wang, H. Y., Fang, N., Altman, Y., Elly, C. & Liu, Y. C. Cbl-b, a RING-type E3 ubiquitin ligase, targets phosphatidylinositol 3-kinase for ubiquitination in T cells. *J. Biol. Chem.* 276, 4872-4878 (2001).

10. Shimura, H. et al., Ubiquitination of a new form of α-synuclein by parkin from human brain: implications for Parkinson's disease. *Science* 293, 263-269 (2001).
11. Tyers, M & Jorgensen, P. Proteolysis and the cell cycle: with this RING I do the destroy. *Curr. Opin. Genet. Dev.* 10, 54-64 (2000). Review
12. Murata, K., Wu, J. & Brautigan, D. L. B cell receptor-associated protein α4 displays rapamycin sensitive binding directly to the catalytic subunit of protein phosphatase 2A. *Proc. Natl Acad. Sci.* 94, 10624-10629 (1997).
13. Price, N. E., Wadzinski, B. & Mumby, M. C. An anchoring factor targets protein phosphatase 2A to brain microtubules. *Mol. Brain Res.* 73, 68-77 (1999).
14. Dick, L. R., Cruikshank, A. A., Grenier, L., Melandri, F. D., Nunes, S. L. & Stein, R. L. Mechanistic studies on the inactivation of the proteasome by lactacystin. *J. Biol. Chem.* 271, 7273-7276 (1996).
15. Chen, J., Peterson, R. T. & Schreiber, S. L. α4 associates with protein phosphatase 2A, 4, and 6. *Biochem. Biophys. Res. Commun.* 247, 827-832 (1998).
16. Inui, S. et al. Molecular cloning of a cDNA clone encoding a phosphoprotein component related to the Ig receptor-mediated signal transduction. *J. Immunol.* 154, 2714-2723 (1995).
17. Buchner, G. et al. MID2, a homologue of the Opitz syndrome gene MID1: similarities in subcellular localization and differences in expression during development. *Hum. Mol. Genet.* 8, 1397-1407 (1999).
18. Reymond, A. et al. The tripartite motif family identifies cell compartments. *EMBO J.* 20, 2140-2151 (2001).
19. Moynihan, T. P. et al. The ubiquitin-conjugating enzymes UbCH7 and UbCH8 interact with RING finger/IBR motif-containing domains of HHARI and H7-AP1. *J. Biol. Chem.* 274, 30963-30968 (1999).
20. Cainarca, S., Messali, S., Ballabio, A. & Meroni, G. Functional characterization of the Opitz syndrome gene product (midin): evidence for homodimerization and association with microtubules throughout the cell cycle. *Hum. Mol. Genet.* 8, 1387-1396 (1999).
21. Sontag, E., Nunbhakdi-Craig, V., Bloom, G. S. & Mumby, M. C. A novel pool of protein phosphatase 2A is associated with microtubules and is regulated during the cell cycle. *J. Cell Biol.* 128, 1131-1144 (1995).
22. Baharians, Z. & Schönthal, A. H. Autoregulation of protein phsphatase type 2A expression. *J. Biol. Chem.* 273, 19019-19024 (1998).
23. Zolnierowsicz, S. Type 2A protein phosphatase, the complex regulator of numerous signaling pathways. *Biochem. Pharmacol.* 60, 1225-1235 (2000).
24. Wera, S. & Hemmings, B. A. Serine/threonine protein phosphatases. *Biochem. J.* 311, 17-29 (1995).
25. Goldberg, Y. Protein phosphatase 2A: who shall regulate the regulator? *Biochem. Pharmacol.* 57, 321-328 (1999).
26. Trojanowski, J. Q. & Lee, V. M. Y. Phosphorylation of paired helical filament tau in Alzheimer's disease neurofibrillary lesions: focusing on phosphatases. *FASEB J.* 9, 1570-1576 (1995).
27. Baharians, Z. & Schönthal, A. H. Reduction of Ha-ras-induced cellular transformation by elevated expression of protein phosphatase type 2A. *Mol. Carcinogenesis* 24, 246-254 (1999).
28. Kawabe, T., Muslin, A. J., & Korsmeyer, S. J. HOX11 interacts with protein phosphatases PP2A and PP1 and disrupts a $G_2$/M cell-cycle checkpoint. *Nature* 385, 454-458
29. Hsu, W., Zeng, L. & Constantini, F. Identification of a domain of axin that binds to the serine/threonine protein phosphatase 2A and a self-binding domain. *J. Biol. Chem.* 274, 3439-3445 (1999).
30. Uemura, T., Shiomi, K, Togashi, S & Takeichi, M. Mutation of twins encoding a regulator of protein phosphatase 2A leads to pattern duplication in *Drosophila* imaginal disks. *Genes. Dev.* 7, 429-440 (1993).
31. Deng, X., Takahiko, I., Carr., B., Mumby, W. & May, W. S. Reversible phosphorylation of bcl2 following interleukin 3 or bryostatin 1 is mediated by direct interaction with protein phosphatase 2A. *J. Biol. Chem.* 273, 34157-34163 (1998).
32. Santoro, M. F. et al. Regulation of protein phosphatase 2A activity by caspase-3 during apoptosis. *J. Biol. Chem.* 273, 13119-13128 (1998).
33. Maier, G. D. et al. Regulation of cytoskeletal organization in tumor cells by protein phosphatase-1 and -2A. *Int J. Cancer* 61, 54-61 (1995).
34. Ito, A. et al. Truncated isoform of the PP2A B56 subunit promotes cell motility through paxillin phosphorylation. *EMBO J.* 19, 562-571 (2000).
35. Kobayashi, N., Reiser, J., Schwarz, K., Sakai, T., Kriz, W. & Mundel, P. Process formation of podocytes: morphogenetic activity of microtubules and regulation by protein serine/threonine phosphatase PP2A. *Histochem. Cell Biol.* 115, 255-266 (2001).
36. Gong, C. et al. Regulation of phosphorylation of neuronal microtubule-associated proteins MAP1b and MAP2 by protein phosphatase-2A and -2B in rat brain. *Brain Res.* 853, 299-309 (2000).
37. Avila, J., Dominguez, J. & Diaz, N. J. Regulation of microtubule dynamics by microtubule-associated protein expression and phosphorylation during neuronal development. *Int. J. Dev. Biol.* 38, 13-25 (1994).
38. Sapir, T., Cahana, A., Seger, R., Nekhai, S. & Reiner, O. LIS1 is a microtubule-associated phosphoprotein. *Eur. J. Biochem.* 265, 181-188 (1999).
39. Liu, J., Prickett, T. D., Elliott, E., Meroni, G. & Brautigan, D. L. Phosphorylation and microtubule association of the Opitz syndrome protein mid-1 is regulated by protein phosphatase 2A via binding to the regulatory subunit α4. *Proc. Natl. Acad. Sci. USA* 98, 6650-6655 (2001).
40. Jackson, P. K. et al. The lore of the RINGs: substrate recognition and catalysis by ubiquitin ligases. *Trends Cell Biol.* 10, 429-439 (2000).
41. Freemont, P. S. RING for destruction? *Curr. Biol.* 10, R84-R87 (2000). Review
42. Joazeiro, C. A. & Weissman, A. M. RING finger proteins: mediators of ubiquitin ligase activity. *Cell* 102, 549-552 (2000). Review
43. Nanahoshi, M. et al. Regulation of protein phosphatase 2A catalytic activity by α4 protein and its yeast homologue Tap42. *Biochem. Biophys. Res. Commun.* 251, 520-526 (1998).
44. Briault, S. et al. A gene for FG syndrome maps in the Xq12-q21.31 region. *Am. J. Med. Genet* 73, 87-90 (1997).
45. Graham, J. M. et al. Report of three new families with linkage to Xq12-q22.1. *Am. J. Med. Genet.* 80, 145-156 (1998).
46. Opitz, J. M. & Kaveggia, E. G. The FG syndrome: an X-linked recessive syndrome of multiple congenital anomalies and mental retardation. *Z. Kinderheilk.* 117, 1-18 (1974).
47. Fields, S. & Sternglanz, R. The two-hybrid system: an assay for protein-protein interactions. *Trends Genet* 10, 286-292 (1994). Review 48. Klose, J. & Kobalz, U. Two-dimensional electrophoresis of proteins: an updated protocol and implications for a functional analysis of the genome. *Electrophoresis* 16, 1034-1059 (1995).

Bosher, J. M., Labouessse, M. RNA interference: genetic wand and genetic watchdog. *Nat Cell Biol.* 2, E31-E36 (2001)

Iqbal, K., Alonso, A. D., Gondal, J. A., Gong, C. X., Haque, N., Khatoon, S., Sengupta, A., Wang, J. Z., Grundke-Iqbal, I. Mechanism of neurofibrillary degeneration and pharmacologic therapeutic approach. *J. Neural Transm. Suppl* 59, 213-222 (2000)

Klimaschewski, L., Nindl, Pimpl, M., Waltinger, P., Pfaller, K. Biolistic transfection and morphological analysis of cultured sympathetic neurons. *J. Neurosc. Meth.* 113, 63-71 (2002)

Krishnan, V., Pereira, F. A., Qui, Y., Chen, C.-H., Beachy, P. A., Tsai, S. Y., Tsai, M.-J. Mediation of sonoc hedgehog-induced expression of COUP-TFII by a protein Phosphatase. *Science* 278, 1947-1950 (1997)

Maccioni, R. B., Munos, J. P., Barbeito, L. The molecular basis of Alzheimer's disease and other neurodegenerative disorders. *Arch. Med. Res.* 32, 367-381 (2001)

Rapoport, M., Dawson, H. N., Binder, L. I., Vitek, M-P., Ferreira, A. Tau is essential to beta-amyloid-induced neurotoxicity. *Proc. Natl. Acad. Sci. USA* 99, 6364-6369 (2002)

Richardson, J. A., Burns, D. K. Mouse models of Alzheimer's disease: a quest for plaques and tangles. *ILARJ* 43, 89-99 (2002)

Schwarze, S. R., Ho, A., Vocero-Akbani, A., Dowdy, S. F. In vivo protein transduction: Delivery of a biologically active protein into the mouse. *Science* 285, 1569-1572 (1999)

Schwarze, S. R., Hruska, K. A., Dowdy, S. F. Protein transduction: unrestricted delivery into all cells? *Trends Cell. Biol.* 10, 290-295 (2000)

Shanely, T. P., Vasi, N., Denenberg, A., Wong, H. R. The serine/threonine phosphatase PP2A, endogenous regulator of inflammatory cell signaling. *J. Immunol.* 166, 966-972

Bastians H, Krebber H, Hoheisel J, Ohl S, Lichter P, Ponstingl H and Joos S. "Assignment of the human serine/threonine protein phosphatase 4 gene (PPP4CC) to chromosome 16p 11-p 12 by fluorescence in situ hybridization" JOURNAL Genomics 42 (1), 181-182 (1997)

Bastians, H., Krebber, H., Vetrie, D., Hoheisel, J., Lichter, P., Ponstingl, H. and Joos, S. "Localization of the novel serine/threonine protein phosphatase 6 gene (PPP6C) to human chromosome Xq22.3" JOURNAL Genomics 41 (2), 296-297 (1997)

Stone, S. R., Mayer, R., Wernet, W., Maurer, F., Hofsteenge, J. and Hemmings, B. A. "The nucleotide sequence of the cDNA encoding the human lung protein phosphatase 2A alpha catalytic subunit" JOURNAL Nucleic Acids Res. 16 (23), 1365 (1988)

Hemmings, B. A., Wernet, W., Mayer, R., Maurer, F., Hofsteenge, J. and Stone, S. R. "The nucleotide sequence of the cDNA encoding the human lung protein phosphatase 2A beta catalytic subunit" JOURNAL Nucleic Acids Res. 16 (23), 11366 (1988)

Quaderi, N., Schweiger, S., Gaudenz, K., Franco, B., Rugarli, E. I., Berger, W., Feldman, G. J., Volta, M., Andolfi, G., Gilgenkrantz, S., Marion, R. W., Hennekam, R. C. M., Opit, J. M., Muenke, M., Ropers, H. H. and Ballabio, A. "Opitz G/BBB syndrome, a defect of midline development, is due to mutations in a new RING finger gene on Xp22" JOURNAL Nat. Genet. 17 (3), 285-291 (1997)

Buchner, G., Montini, E., Andolfi, G., Quaderi, N., Cainarca, S., Messali, S., Bassi, M. T., Ballabio, A., Meroni, G. and Franco, B. "MID2, a homologue of the Opitz syndrome gene MID1: similarities in subcellular localization and differences in expression during development" JOURNAL Hum. Mol. Genet. 8 (8), 1397-1407 (1999)

Onda, M., Inui, S., Maeda, K., Suzuki, M., Takahashi, E. and Sakaguchi, N. "Expression and chromosomal localization of the human alpha 4/IGBP1 gene, the structure of which is closely related to the yeast TAP42 protein of the rapamycin-sensitive signal transduction pathway" JOURNAL Genomics 46 (3), 373-378 (1997)

Liu Jun et. al., "Phosphorylation and microtubule association of the Opitz syndrome protein mid-1 is regulated by protein phosphatase 2A via binding to the regulatory subunit α4", PNAS, 6650-6655, vol 98 (2001)

Estelle Sontag, "Protein phosphatase 2A: the Trojan Horse of cellular signaling", Cellular Signaling 13, 7-16 (2001)

Short, Kieran M. et al., "MID1 and MID2 homo- and heterodimerise to tether the reapamycin-sensitive PP2A regulatory subunit . . . ", BMC Cell Biology 3 (2002)

Trockenbacher et al., "MID1, mutated in Opitz syndrome, encodes an ubiquitin ligase that targets phosphates 2A for degradation", Nature Genetics, vol. 29, 287-294 (2001)

Wicking C and McGlinn E., "The role of hedgehog signalling in tumorigenesis", Cancer Lett.; 173(1): 1-7 (2001)

Ruiz i Altaba A. et al., "Gli and hedgehog in cancer: tumours, embryos and stem cells", Nat Rev Cancer 2(5):361-372 (2002)

Mullor et al., "Pathways and consequences: Hedgehog signaling in human disease", Trends Cell Biol. 12(12): 562-569

Elbashir et al., "Duplexes of 21-nucleotide RNAs mediate RNA intererence in cultured mammalian cells", Nature 411(6836): 494-498 (2001)

The invention claimed is:

1. A method of identifying a molecule that interferes with the interaction of MID1 or MID2 and α 4 comprising
   (a) contacting under suitable conditions MID1 (SEQ ID NO:1) or MID2 (SEQ ID NO:2) with α4 or a peptidic fragment of α4 comprising amino acids 236-279 (SEQ ID NO:4) in the presence of a candidate molecule; and
   b) assessing whether said candidate molecule interferes with said interaction of MID1 or MID2 and α 4.

2. The method of claim 1, wherein a molecule that interferes with said interaction of MID1 or MID2 and α 4 causes a decrease in cell proliferation or an increase in cell apoptosis.

3. The method of claim 1, wherein said candidate molecule comprises a small inorganic or small organic molecule.

4. The method of claim 1, wherein said candidate molecule comprises an interfering RNA (RNAi).

* * * * *

SEQUENCE LISTING

```
<160> NUMBER OF SEQ ID NOS: 26

<210> SEQ ID NO 1
<211> LENGTH: 58
<212> TYPE: PRT
<213> ORGANISM: Homo sapiens

<400> SEQUENCE: 1

Ala Asn Thr Met Thr Ser Ala Glu Lys Val Leu Cys Gln Phe Cys Asp
1               5                   10                  15
```

```
Gln Asp Pro Ala Gln Asp Ala Val Lys Thr Cys Val Thr Cys Glu Val
            20                  25                  30

Ser Tyr Cys Asp Glu Cys Leu Lys Ala Thr His Pro Asn Lys Lys Pro
                35                  40                  45

Phe Thr Gly His Arg Leu Ile Glu Pro Ile
    50                  55

<210> SEQ ID NO 2
<211> LENGTH: 58
<212> TYPE: PRT
<213> ORGANISM: Homo sapiens

<400> SEQUENCE: 2

Pro Thr Thr Ala Met Ser Ser Glu Arg Ile Ala Cys Gln Phe Cys Glu
1               5                   10                  15

Gln Asp Pro Pro Arg Asp Ala Val Lys Thr Cys Ile Thr Cys Glu Val
            20                  25                  30

Ser Tyr Cys Asp Arg Cys Leu Arg Ala Thr His Pro Asn Lys Lys Pro
                35                  40                  45

Phe Thr Ser His Arg Leu Val Glu Pro Val
    50                  55

<210> SEQ ID NO 3
<211> LENGTH: 92
<212> TYPE: PRT
<213> ORGANISM: Homo sapiens

<400> SEQUENCE: 3

Asn Tyr Leu Thr Gln Cys His Cys Tyr His Val Ala Glu Phe Glu Leu
1               5                   10                  15

Pro Lys Thr Met Asn Asn Ser Ala Glu Asn His Thr Ala Asn Ser Ser
            20                  25                  30

Met Ala Tyr Pro Ser Leu Val Ala Met Ala Ser Gln Arg Gln Ala Lys
                35                  40                  45

Ile Gln Arg Tyr Lys Gln Lys Glu Leu Glu His Arg Leu Ser Ala
            50                  55                  60

Met Lys Ser Ala Val Glu Ser Gly Gln Ala Asp Asp Glu Arg Val Arg
65                  70                  75                  80

Glu Tyr Tyr Leu Leu His Leu Gln Arg Trp Ile Asp
                85                  90

<210> SEQ ID NO 4
<211> LENGTH: 44
<212> TYPE: PRT
<213> ORGANISM: Homo sapiens

<400> SEQUENCE: 4

Glu Arg Pro Pro Val Lys Pro Phe Ile Leu Thr Arg Asn Met Ala Gln
1               5                   10                  15

Ala Lys Val Phe Gly Ala Gly Tyr Pro Ser Leu Pro Thr Met Thr Val
            20                  25                  30

Ser Asp Trp Tyr Glu Gln His Arg Lys Tyr Gly Ala
                35                  40

<210> SEQ ID NO 5
<211> LENGTH: 1522
<212> TYPE: PRT
<213> ORGANISM: Homo sapiens

<400> SEQUENCE: 5
```

-continued

```
Met Glu Ala Gln Ser His Ser Ser Thr Thr Thr Glu Lys Lys Lys Val
1               5                   10                  15

Glu Asn Ser Ile Val Lys Cys Ser Thr Arg Thr Asp Val Ser Glu Lys
            20                  25                  30

Ala Val Ala Ser Ser Thr Thr Ser Asn Glu Asp Glu Ser Pro Gly Gln
        35                  40                  45

Thr Tyr His Arg Glu Arg Arg Asn Ala Ile Thr Met Gln Pro Gln Asn
    50                  55                  60

Val Gln Gly Leu Ser Lys Val Ser Glu Glu Pro Ser Thr Ser Ser Asp
65              70                  75                  80

Glu Arg Ala Ser Leu Ile Lys Lys Glu Ile His Gly Ser Leu Pro His
                85                  90                  95

Val Ala Glu Pro Ser Val Pro Tyr Arg Gly Thr Val Phe Ala Met Asp
            100                 105                 110

Pro Arg Asn Gly Tyr Met Glu Pro His Tyr His Pro His Leu Phe
        115                 120                 125

Pro Ala Phe His Pro Pro Val Pro Ile Asp Ala Arg His His Glu Gly
    130                 135                 140

Arg Tyr His Tyr Asp Pro Ser Pro Ile Pro Pro Leu His Met Thr Ser
145                 150                 155                 160

Ala Leu Ser Ser Pro Thr Tyr Pro Asp Leu Pro Phe Ile Arg Ile
            165                 170                 175

Ser Pro His Arg Asn Pro Ala Ala Ser Glu Ser Pro Phe Ser Pro
        180                 185                 190

Pro His Pro Tyr Ile Asn Pro Tyr Met Asp Tyr Ile Arg Ser Leu His
    195                 200                 205

Ser Ser Pro Ser Leu Ser Met Ile Ser Ala Thr Arg Gly Leu Ser Pro
210                 215                 220

Thr Asp Ala Pro His Ala Gly Val Ser Pro Ala Glu Tyr Tyr His Gln
225                 230                 235                 240

Met Ala Leu Leu Thr Gly Gln Arg Ser Pro Tyr Ala Asp Ile Ile Pro
            245                 250                 255

Ser Ala Ala Thr Ala Gly Thr Gly Ala Ile His Met Glu Tyr Leu His
        260                 265                 270

Ala Met Asp Ser Thr Arg Phe Ser Ser Pro Arg Leu Ser Ala Arg Pro
    275                 280                 285

Ser Arg Lys Arg Thr Leu Ser Ile Ser Pro Leu Ser Asp His Ser Phe
290                 295                 300

Asp Leu Gln Thr Met Ile Arg Thr Ser Pro Asn Ser Leu Val Thr Ile
305                 310                 315                 320

Leu Asn Asn Ser Arg Ser Ser Ser Ala Ser Gly Ser Tyr Gly His
            325                 330                 335

Leu Ser Ala Ser Ala Ile Ser Pro Ala Leu Ser Phe Thr Tyr Ser Ser
        340                 345                 350

Ala Pro Val Ser Leu His Met His Gln Gln Ile Leu Ser Arg Gln Gln
    355                 360                 365

Ser Leu Gly Ser Ala Phe Gly His Ser Pro Leu Ile His Pro Ala
370                 375                 380

Pro Thr Phe Pro Thr Gln Arg Pro Ile Pro Gly Ile Pro Thr Val Leu
385                 390                 395                 400

Asn Pro Val Gln Val Ser Ser Gly Pro Ser Glu Ser Ser Gln Asn Lys
            405                 410                 415

Pro Thr Ser Glu Ser Ala Val Ser Ser Thr Gly Asp Pro Met His Asn
        420                 425                 430
```

-continued

```
Lys Arg Ser Lys Ile Lys Pro Asp Glu Asp Leu Pro Ser Pro Gly Ala
            435                 440                 445

Arg Gly Gln Gln Glu Gln Pro Glu Gly Thr Thr Leu Val Lys Glu Glu
        450                 455                 460

Gly Asp Lys Asp Glu Ser Lys Gln Glu Pro Glu Val Ile Tyr Glu Thr
465                 470                 475                 480

Asn Cys His Trp Glu Gly Cys Ala Arg Glu Phe Asp Thr Gln Glu Gln
                485                 490                 495

Leu Val His His Ile Asn Asn Asp His Ile His Gly Glu Lys Lys Glu
            500                 505                 510

Phe Val Cys Arg Trp Leu Asp Cys Ser Arg Glu Gln Lys Pro Phe Lys
        515                 520                 525

Ala Gln Tyr Met Leu Val Val His Met Arg Arg His Thr Gly Glu Lys
    530                 535                 540

Pro His Lys Cys Thr Phe Glu Gly Cys Thr Lys Ala Tyr Ser Arg Leu
545                 550                 555                 560

Glu Asn Leu Lys Thr His Leu Arg Ser His Thr Gly Glu Lys Pro Tyr
                565                 570                 575

Val Cys Glu His Glu Gly Cys Asn Lys Ala Phe Ser Asn Ala Ser Asp
            580                 585                 590

Arg Ala Lys His Gln Asn Arg Thr His Ser Asn Glu Lys Pro Tyr Val
        595                 600                 605

Cys Lys Ile Pro Gly Cys Thr Lys Arg Tyr Thr Asp Pro Ser Ser Leu
    610                 615                 620

Arg Lys His Val Lys Thr Val His Gly Pro Glu Ala His Val Thr Lys
625                 630                 635                 640

Lys Gln Arg Gly Asp Ile His Pro Arg Pro Pro Pro Pro Arg Asp Ser
                645                 650                 655

Gly Ser His Ser Gln Ser Arg Ser Pro Gly Arg Pro Thr Gln Gly Ala
            660                 665                 670

Leu Gly Glu Gln Gln Asp Leu Ser Asn Thr Thr Ser Lys Arg Glu Glu
        675                 680                 685

Cys Leu Gln Val Lys Thr Val Lys Ala Glu Lys Pro Met Thr Ser Gln
    690                 695                 700

Pro Ser Pro Gly Gly Gln Ser Ser Cys Ser Ser Gln Gln Ser Pro Ile
705                 710                 715                 720

Ser Asn Tyr Ser Asn Ser Gly Leu Glu Leu Pro Leu Thr Asp Gly Gly
                725                 730                 735

Ser Ile Gly Asp Leu Ser Ala Ile Asp Glu Thr Pro Ile Met Asp Ser
            740                 745                 750

Thr Ile Ser Thr Ala Thr Thr Ala Leu Ala Leu Gln Ala Arg Arg Asn
        755                 760                 765

Pro Ala Gly Thr Lys Trp Met Glu His Val Lys Leu Glu Arg Leu Lys
    770                 775                 780

Gln Val Asn Gly Met Phe Pro Arg Leu Asn Pro Ile Leu Pro Pro Lys
785                 790                 795                 800

Ala Pro Ala Val Ser Pro Leu Ile Gly Asn Gly Thr Gln Ser Asn Asn
                805                 810                 815

Thr Cys Ser Leu Gly Gly Pro Met Thr Leu Leu Pro Gly Arg Ser Asp
            820                 825                 830

Leu Ser Gly Val Asp Val Thr Met Leu Asn Met Leu Asn Arg Arg Asp
        835                 840                 845

Ser Ser Ala Ser Thr Ile Ser Ser Ala Tyr Leu Ser Ser Arg Arg Ser
```

-continued

```
            850             855             860
Ser Gly Ile Ser Pro Cys Phe Ser Ser Arg Arg Ser Ser Glu Ala Ser
865             870             875             880

Gln Ala Glu Gly Arg Pro Gln Asn Val Ser Val Ala Asp Ser Tyr Asp
                885             890             895

Pro Ile Ser Thr Asp Ala Ser Arg Arg Ser Ser Glu Ala Ser Gln Ser
                900             905             910

Asp Gly Leu Pro Ser Leu Leu Ser Leu Thr Pro Ala Gln Gln Tyr Arg
            915             920             925

Leu Lys Ala Lys Tyr Ala Ala Ala Thr Gly Gly Pro Pro Thr Pro
930             935             940

Leu Pro Asn Met Glu Arg Met Ser Leu Lys Thr Arg Leu Ala Leu Leu
945             950             955             960

Gly Asp Ala Leu Glu Pro Gly Val Ala Leu Pro Val His Ala Pro
                965             970             975

Arg Arg Cys Ser Asp Gly Gly Ala His Gly Tyr Gly Arg His Leu
                980             985             990

Gln Pro His Asp Ala Leu Gly His  Gly Val Arg Arg Ala  Ser Asp Pro
            995             1000            1005

Val Arg  Thr Gly Ser Glu Gly  Leu Ala Leu Pro Arg   Val Pro Arg
    1010            1015            1020

Phe Ser  Ser Leu Ser Ser Cys  Asn Pro Pro Ala Met  Ala Thr Ser
    1025            1030            1035

Ala Glu  Lys Arg Ser Leu Val  Leu Gln Asn Tyr Thr  Arg Pro Glu
    1040            1045            1050

Gly Gly  Gln Ser Arg Asn Phe  His Ser Ser Pro Cys  Pro Pro Ser
    1055            1060            1065

Ile Thr  Glu Asn Val Thr Leu  Glu Ser Leu Thr Met  Asp Ala Asp
    1070            1075            1080

Ala Asn  Leu Asn Asp Glu Asp  Phe Leu Pro Asp Asp  Val Val Gln
    1085            1090            1095

Tyr Leu  Asn Ser Gln Asn Gln  Ala Gly Tyr Glu Gln  His Phe Pro
    1100            1105            1110

Ser Ala  Leu Pro Asp Asp Ser  Lys Val Pro His Gly  Pro Gly Asp
    1115            1120            1125

Phe Asp  Ala Pro Gly Leu Pro  Asp Ser His Ala Gly  Gln Gln Phe
    1130            1135            1140

His Ala  Leu Glu Gln Pro Cys  Pro Glu Gly Ser Lys  Thr Asp Leu
    1145            1150            1155

Pro Ile  Gln Trp Asn Glu Val  Ser Ser Gly Ser Ala  Asp Leu Ser
    1160            1165            1170

Ser Ser  Lys Leu Lys Cys Gly  Pro Arg Pro Ala Val  Pro Gln Thr
    1175            1180            1185

Arg Ala  Phe Gly Phe Cys Asn  Gly Met Val Val His  Pro Gln Asn
    1190            1195            1200

Pro Leu  Arg Ser Gly Pro Ala  Gly Gly Tyr Gln Thr  Leu Gly Glu
    1205            1210            1215

Asn Ser  Asn Pro Tyr Gly Gly  Pro Glu His Leu Met  Leu His Asn
    1220            1225            1230

Ser Pro  Gly Ser Gly Thr Ser  Gly Asn Ala Phe His  Glu Gln Pro
    1235            1240            1245

Cys Lys  Ala Pro Gln Tyr Gly  Asn Cys Leu Asn Arg  Gln Pro Val
    1250            1255            1260
```

| | | | | | | | | | | |
|---|---|---|---|---|---|---|---|---|---|---|
| Ala | Pro | Gly | Ala | Leu | Asp | Gly | Ala | Cys | Gly | Ala | Gly | Ile | Gln | Ala |
| | 1265 | | | | 1270 | | | | 1275 | |

Ala Pro Gly Ala Leu Asp Gly Ala Cys Gly Ala Gly Ile Gln Ala
        1265                        1270                  1275

Ser Lys Leu Lys Ser Thr Pro Met Gln Gly Ser Gly Gly Gln Leu
        1280                        1285                  1290

Asn Phe Gly Leu Pro Val Ala Pro Asn Glu Ser Ala Gly Ser Met
        1295                        1300                  1305

Val Asn Gly Met Gln Asn Gln Asp Pro Val Gly Gln Gly Tyr Leu
        1310                        1315                  1320

Ala His Gln Leu Leu Gly Asp Ser Met Gln His Pro Gly Ala Gly
        1325                        1330                  1335

Arg Pro Gly Gln Gln Met Leu Gly Gln Ile Ser Ala Thr Ser His
        1340                        1345                  1350

Ile Asn Ile Tyr Gln Gly Pro Glu Ser Cys Leu Pro Gly Ala His
        1355                        1360                  1365

Gly Met Gly Ser Gln Pro Ser Ser Leu Ala Val Val Arg Gly Tyr
        1370                        1375                  1380

Gln Pro Cys Ala Ser Phe Gly Gly Ser Arg Arg Gln Ala Met Pro
        1385                        1390                  1395

Arg Asp Ser Leu Ala Leu Gln Ser Gly Gln Leu Ser Asp Thr Ser
        1400                        1405                  1410

Gln Thr Cys Arg Val Asn Gly Ile Lys Met Glu Met Lys Gly Gln
        1415                        1420                  1425

Pro His Pro Leu Cys Ser Asn Leu Gln Asn Tyr Ser Gly Gln Phe
        1430                        1435                  1440

Tyr Asp Gln Thr Val Gly Phe Ser Gln Gln Asp Thr Lys Ala Gly
        1445                        1450                  1455

Ser Phe Ser Ile Ser Asp Ala Ser Cys Leu Leu Gln Gly Thr Ser
        1460                        1465                  1470

Ala Lys Asn Ser Glu Leu Leu Ser Pro Gly Ala Asn Gln Val Thr
        1475                        1480                  1485

Ser Thr Val Asp Ser Leu Asp Ser His Asp Leu Glu Gly Val Gln
        1490                        1495                  1500

Ile Asp Phe Asp Ala Ile Ile Asp Asp Gly Asp His Ser Ser Leu
        1505                        1510                  1515

Met Ser Gly Ala
        1520

<210> SEQ ID NO 6
<211> LENGTH: 1532
<212> TYPE: PRT
<213> ORGANISM: Homo sapiens

<400> SEQUENCE: 6

Asn Ser Ile Val Lys Cys Ser Thr Arg Thr Asp Val Ser Glu Lys Ala
1                  5                    10                15

Val Ala Ser Ser Thr Thr Ser Asn Glu Asp Glu Ser Pro Gly Gln Thr
                  20                    25                    30

Tyr His Arg Glu Arg Arg Asn Ala Ile Thr Met Gln Pro Gln Asn Val
                35                    40                    45

Gln Gly Leu Ser Lys Val Ser Glu Glu Pro Thr Ser Ser Asp Glu
      50                    55                    60

Arg Ala Ser Leu Ile Lys Lys Glu Ile His Gly Ser Leu Pro His Val
65                  70                    75                80

Ala Glu Pro Ser Val Pro Tyr Arg Gly Thr Val Phe Ala Met Asp Pro
                85                    90                    95

-continued

```
Arg Asn Gly Tyr Met Glu Pro His Tyr His Pro His Leu Phe Pro
            100                 105             110
Ala Phe His Pro Pro Val Pro Ile Asp Ala Arg His His Glu Gly Arg
        115                 120                 125
Tyr His Tyr Asp Pro Ser Pro Ile Pro Pro Leu His Met Thr Ser Ala
    130                 135                 140
Leu Ser Ser Ser Pro Thr Tyr Pro Asp Leu Pro Phe Ile Arg Ile Ser
145                 150                 155                 160
Pro His Arg Asn Pro Ala Ala Ala Ser Glu Ser Pro Phe Ser Pro Pro
                165                 170                 175
His Pro Tyr Ile Asn Pro Tyr Met Asp Tyr Ile Arg Ser Leu His Ser
            180                 185                 190
Ser Pro Ser Leu Ser Met Ile Ser Ala Thr Arg Gly Leu Ser Pro Thr
        195                 200                 205
Asp Ala Pro His Ala Gly Val Ser Pro Ala Glu Tyr Tyr His Gln Met
    210                 215                 220
Ala Leu Leu Thr Gly Gln Arg Ser Pro Tyr Ala Asp Ile Ile Pro Ser
225                 230                 235                 240
Ala Ala Thr Ala Gly Thr Gly Ala Ile His Met Glu Tyr Leu His Ala
                245                 250                 255
Met Asp Ser Thr Arg Phe Ser Ser Pro Arg Leu Ser Ala Arg Pro Ser
            260                 265                 270
Arg Lys Arg Thr Leu Ser Ile Ser Pro Leu Ser Asp His Ser Phe Asp
        275                 280                 285
Leu Gln Thr Met Ile Arg Thr Ser Pro Asn Ser Leu Val Thr Ile Leu
    290                 295                 300
Asn Asn Ser Arg Ser Ser Ser Ala Ser Gly Ser Tyr Gly His Leu
305                 310                 315                 320
Ser Ala Ser Ala Ile Ser Pro Ala Leu Ser Phe Thr Tyr Ser Ser Ala
                325                 330                 335
Pro Val Ser Leu His Met His Gln Gln Ile Leu Ser Arg Gln Gln Ser
            340                 345                 350
Leu Gly Ser Ala Phe Gly His Ser Pro Pro Leu Ile His Pro Ala Pro
        355                 360                 365
Thr Phe Pro Thr Gln Arg Pro Ile Pro Gly Ile Pro Thr Val Leu Asn
    370                 375                 380
Pro Val Gln Val Ser Ser Gly Pro Ser Glu Ser Ser Gln Asn Lys Pro
385                 390                 395                 400
Thr Ser Glu Ser Ala Val Ser Ser Thr Gly Asp Pro Met His Asn Lys
                405                 410                 415
Arg Ser Lys Ile Lys Pro Asp Glu Asp Leu Pro Ser Pro Gly Ala Arg
            420                 425                 430
Gly Gln Gln Glu Gln Pro Glu Gly Thr Thr Leu Val Lys Glu Glu Gly
        435                 440                 445
Asp Lys Asp Glu Ser Lys Gln Glu Pro Glu Val Ile Tyr Glu Thr Asn
    450                 455                 460
Cys His Trp Glu Gly Cys Ala Arg Glu Phe Asp Thr Gln Glu Gln Leu
465                 470                 475                 480
Val His His Ile Asn Asn Asp His Ile His Gly Glu Lys Lys Glu Phe
                485                 490                 495
Val Cys Arg Trp Leu Asp Cys Ser Arg Glu Gln Lys Pro Phe Lys Ala
            500                 505                 510
Gln Tyr Met Leu Val Val His Met Arg Arg His Thr Gly Glu Lys Pro
        515                 520                 525
```

-continued

His Lys Cys Thr Phe Glu Gly Cys Thr Lys Ala Tyr Ser Arg Leu Glu
    530                 535                 540

Asn Leu Lys Thr His Leu Arg Ser His Thr Gly Glu Lys Pro Tyr Val
545                 550                 555                 560

Cys Glu His Glu Gly Cys Asn Lys Ala Phe Ser Asn Ala Ser Asp Arg
                565                 570                 575

Ala Lys His Gln Asn Arg Thr His Ser Asn Glu Lys Pro Tyr Val Cys
            580                 585                 590

Lys Ile Pro Gly Cys Thr Lys Arg Tyr Thr Asp Pro Ser Ser Leu Arg
        595                 600                 605

Lys His Val Lys Thr Val His Gly Pro Glu Ala His Val Thr Lys Lys
    610                 615                 620

Gln Arg Gly Asp Ile His Pro Arg Pro Pro Pro Arg Asp Ser Gly
625                 630                 635                 640

Ser His Ser Gln Ser Arg Ser Pro Gly Arg Pro Thr Gln Gly Ala Leu
                645                 650                 655

Gly Glu Gln Gln Asp Leu Ser Asn Thr Thr Ser Lys Arg Glu Glu Cys
            660                 665                 670

Leu Gln Val Lys Thr Val Lys Ala Glu Lys Pro Met Thr Ser Gln Pro
        675                 680                 685

Ser Pro Gly Gly Gln Ser Ser Cys Ser Ser Gln Gln Ser Pro Ile Ser
    690                 695                 700

Asn Tyr Ser Asn Ser Gly Leu Glu Leu Pro Leu Thr Asp Gly Gly Ser
705                 710                 715                 720

Ile Gly Asp Leu Ser Ala Ile Asp Glu Thr Pro Ile Met Asp Ser Thr
                725                 730                 735

Ile Ser Thr Ala Thr Thr Ala Leu Ala Leu Gln Ala Arg Arg Asn Pro
            740                 745                 750

Ala Gly Thr Lys Trp Met Glu His Val Lys Leu Glu Arg Leu Lys Gln
        755                 760                 765

Val Asn Gly Met Phe Pro Arg Leu Asn Pro Ile Leu Pro Pro Lys Ala
    770                 775                 780

Pro Ala Val Ser Pro Leu Ile Gly Asn Gly Thr Gln Ser Asn Asn Thr
785                 790                 795                 800

Cys Ser Leu Gly Gly Pro Met Thr Leu Leu Pro Gly Arg Ser Asp Leu
                805                 810                 815

Ser Gly Val Asp Val Thr Met Leu Asn Met Leu Asn Arg Arg Asp Ser
            820                 825                 830

Ser Ala Ser Thr Ile Ser Ser Ala Tyr Leu Ser Ser Arg Arg Ser Ser
        835                 840                 845

Gly Ile Ser Pro Cys Phe Ser Ser Arg Arg Ser Ser Glu Ala Ser Gln
    850                 855                 860

Ala Glu Gly Arg Pro Gln Asn Val Ser Val Ala Asp Ser Tyr Asp Pro
865                 870                 875                 880

Ile Ser Thr Asp Ala Ser Arg Arg Ser Ser Glu Ala Ser Gln Ser Asp
                885                 890                 895

Gly Leu Pro Ser Leu Leu Ser Leu Thr Pro Ala Gln Gln Tyr Arg Leu
            900                 905                 910

Lys Ala Lys Tyr Ala Ala Ala Thr Gly Gly Pro Pro Pro Thr Pro Leu
        915                 920                 925

Pro Asn Met Glu Arg Met Ser Leu Lys Thr Arg Leu Ala Leu Leu Gly
    930                 935                 940

Asp Ala Leu Glu Pro Gly Val Ala Leu Pro Pro Val His Ala Pro Arg

-continued

```
               945                 950                 955                 960
        Arg Cys Ser Asp Gly Gly Ala His Gly Tyr Gly Arg Arg His Leu Gln
                           965                 970                 975
        Pro His Asp Ala Leu Gly His Gly Val Arg Arg Ala Ser Asp Pro Val
                           980                 985                 990
        Arg Thr Gly Ser Glu Gly Leu Ala  Leu Pro Arg Val Pro  Arg Phe Ser
                           995                 1000                1005
        Ser Leu Ser Ser Cys Asn Pro  Pro Ala Met Ala Thr  Ser Ala Glu
                1010                 1015                 1020
        Lys Arg Ser Leu Val Leu Gln  Asn Tyr Thr Arg Pro  Glu Gly Gly
                1025                 1030                 1035
        Gln Ser  Arg Asn Phe His Ser  Ser Pro Cys Pro Pro  Ser Ile Thr
                1040                 1045                 1050
        Glu Asn  Val Thr Leu Glu Ser  Leu Thr Met Asp Ala  Asp Ala Asn
                1055                 1060                 1065
        Leu Asn  Asp Glu Asp Phe Leu  Pro Asp Asp Val Val  Gln Tyr Leu
                1070                 1075                 1080
        Asn Ser  Gln Asn Gln Ala Gly  Tyr Glu Gln His Phe  Pro Ser Ala
                1085                 1090                 1095
        Leu Pro  Asp Asp Ser Lys Val  Pro His Gly Pro Gly  Asp Phe Asp
                1100                 1105                 1110
        Ala Pro  Gly Leu Pro Asp Ser  His Ala Gly Gln Gln  Phe His Ala
                1115                 1120                 1125
        Leu Glu  Gln Pro Cys Pro Glu  Gly Ser Lys Thr Asp  Leu Pro Ile
                1130                 1135                 1140
        Gln Trp  Asn Glu Val Ser Ser  Gly Ser Ala Asp Leu  Ser Ser Ser
                1145                 1150                 1155
        Lys Leu  Lys Cys Gly Pro Arg  Pro Ala Val Pro Gln  Thr Arg Ala
                1160                 1165                 1170
        Phe Gly  Phe Cys Asn Gly Met  Val Val His Pro Gln  Asn Pro Leu
                1175                 1180                 1185
        Arg Ser  Gly Pro Ala Gly Gly  Tyr Gln Thr Leu Gly  Glu Asn Ser
                1190                 1195                 1200
        Asn Pro  Tyr Gly Gly Pro Glu  His Leu Met Leu His  Asn Ser Pro
                1205                 1210                 1215
        Gly Ser  Gly Thr Ser Gly Asn  Ala Phe His Glu Gln  Pro Cys Lys
                1220                 1225                 1230
        Ala Pro  Gln Tyr Gly Asn Cys  Leu Asn Arg Gln Pro  Val Ala Pro
                1235                 1240                 1245
        Gly Ala  Leu Asp Gly Ala Cys  Gly Ala Gly Ile Gln  Ala Ser Lys
                1250                 1255                 1260
        Leu Lys  Ser Thr Pro Met Gln  Gly Ser Gly Gly Gln  Leu Asn Phe
                1265                 1270                 1275
        Gly Leu  Pro Val Ala Pro Asn  Glu Ser Ala Gly Ser  Met Val Asn
                1280                 1285                 1290
        Gly Met  Gln Asn Gln Asp Pro  Val Gly Gln Gly Tyr  Leu Ala His
                1295                 1300                 1305
        Gln Leu  Leu Gly Asp Ser Met  Gln His Pro Gly Ala  Gly Arg Pro
                1310                 1315                 1320
        Gly Gln  Gln Met Leu Gly Gln  Ile Ser Ala Thr Ser  His Ile Asn
                1325                 1330                 1335
        Ile Tyr  Gln Gly Pro Glu Ser  Cys Leu Pro Gly Ala  His Gly Met
                1340                 1345                 1350
```

```
Gly Ser Gln Pro Ser Ser Leu Ala Val Val Arg Gly Tyr Gln Pro
    1355                1360                1365

Cys Ala Ser Phe Gly Gly Ser Arg Arg Gln Ala Met Pro Arg Asp
1370                1375                1380

Ser Leu Ala Leu Gln Ser Gly Gln Leu Ser Asp Thr Ser Gln Thr
    1385                1390                1395

Cys Arg Val Asn Gly Ile Lys Met Glu Met Lys Gly Gln Pro His
1400                1405                1410

Pro Leu Cys Ser Asn Leu Gln Asn Tyr Ser Gly Gln Phe Tyr Asp
    1415                1420                1425

Gln Thr Val Gly Phe Ser Gln Gln Asp Thr Lys Ala Gly Ser Phe
    1430                1435                1440

Ser Ile Ser Asp Ala Ser Cys Leu Leu Gln Gly Thr Ser Ala Lys
    1445                1450                1455

Asn Ser Glu Leu Leu Ser Pro Gly Ala Asn Gln Val Thr Ser Thr
1460                1465                1470

Val Asp Ser Leu Asp Ser His Asp Leu Glu Gly Val Gln Ile Asp
    1475                1480                1485

Phe Asp Ala Ile Ile Asp Asp Gly Asp His Ser Ser Leu Met Ser
    1490                1495                1500

Gly Ala Leu Ser Pro Ser Ile Ile Gln Asn Leu Ser His Ser Ser
    1505                1510                1515

Ser Arg Leu Thr Thr Pro Arg Ala Ser Leu Pro Phe Pro Val
    1520                1525                1530

<210> SEQ ID NO 7
<211> LENGTH: 1579
<212> TYPE: PRT
<213> ORGANISM: Homo sapiens

<400> SEQUENCE: 7

Asn Ser Ile Val Lys Cys Ser Thr Arg Thr Asp Val Ser Glu Lys Ala
1               5                   10                  15

Val Ala Ser Ser Thr Thr Ser Asn Glu Asp Glu Ser Pro Gly Gln Thr
            20                  25                  30

Tyr His Arg Glu Arg Arg Asn Ala Ile Thr Met Gln Pro Gln Asn Val
        35                  40                  45

Gln Gly Leu Ser Lys Val Ser Glu Glu Pro Ser Thr Ser Ser Asp Glu
    50                  55                  60

Arg Ala Ser Leu Ile Lys Lys Glu Ile His Gly Ser Leu Pro His Val
65                  70                  75                  80

Ala Glu Pro Ser Val Pro Tyr Arg Gly Thr Val Phe Ala Met Asp Pro
                85                  90                  95

Arg Asn Gly Tyr Met Glu Pro His Tyr His Pro Pro His Leu Phe Pro
            100                 105                 110

Ala Phe His Pro Pro Val Pro Ile Asp Ala Arg His His Glu Gly Arg
        115                 120                 125

Tyr His Tyr Asp Pro Ser Pro Ile Pro Pro Leu His Met Thr Ser Ala
    130                 135                 140

Leu Ser Ser Ser Pro Thr Tyr Pro Asp Leu Pro Phe Ile Arg Ile Ser
145                 150                 155                 160

Pro His Arg Asn Pro Ala Ala Ser Glu Ser Pro Phe Ser Pro Pro
                165                 170                 175

His Pro Tyr Ile Asn Pro Tyr Met Asp Tyr Ile Arg Ser Leu His Ser
            180                 185                 190
```

```
Ser Pro Ser Leu Ser Met Ile Ser Ala Thr Arg Gly Leu Ser Pro Thr
        195                 200                 205

Asp Ala Pro His Ala Gly Val Ser Pro Ala Glu Tyr His Gln Met
    210                 215                 220

Ala Leu Leu Thr Gly Gln Arg Ser Pro Tyr Ala Asp Ile Ile Pro Ser
225                 230                 235                 240

Ala Ala Thr Ala Gly Thr Gly Ala Ile His Met Glu Tyr Leu His Ala
                245                 250                 255

Met Asp Ser Thr Arg Phe Ser Pro Arg Leu Ser Ala Arg Pro Ser
                260                 265                 270

Arg Lys Arg Thr Leu Ser Ile Ser Pro Leu Ser Asp His Ser Phe Asp
            275                 280                 285

Leu Gln Thr Met Ile Arg Thr Ser Pro Asn Ser Leu Val Thr Ile Leu
        290                 295                 300

Asn Asn Ser Arg Ser Ser Ser Ala Ser Gly Ser Tyr Gly His Leu
305                 310                 315                 320

Ser Ala Ser Ala Ile Ser Pro Ala Leu Ser Phe Thr Tyr Ser Ser Ala
                325                 330                 335

Pro Val Ser Leu His Met His Gln Gln Ile Leu Ser Arg Gln Gln Ser
                340                 345                 350

Leu Gly Ser Ala Phe Gly His Ser Pro Pro Leu Ile His Pro Ala Pro
                355                 360                 365

Thr Phe Pro Thr Gln Arg Pro Ile Pro Gly Ile Pro Thr Val Leu Asn
        370                 375                 380

Pro Val Gln Val Ser Ser Gly Pro Ser Glu Ser Ser Gln Asn Lys Pro
385                 390                 395                 400

Thr Ser Glu Ser Ala Val Ser Ser Thr Gly Asp Pro Met His Asn Lys
                405                 410                 415

Arg Ser Lys Ile Lys Pro Asp Glu Asp Leu Pro Ser Pro Gly Ala Arg
                420                 425                 430

Gly Gln Gln Glu Gln Pro Glu Gly Thr Thr Leu Val Lys Glu Glu Gly
            435                 440                 445

Asp Lys Asp Glu Ser Lys Gln Glu Pro Glu Val Ile Tyr Glu Thr Asn
        450                 455                 460

Cys His Trp Glu Gly Cys Ala Arg Glu Phe Asp Thr Gln Glu Gln Leu
465                 470                 475                 480

Val His His Ile Asn Asn Asp His Ile His Gly Glu Lys Lys Glu Phe
                485                 490                 495

Val Cys Arg Trp Leu Asp Cys Ser Arg Glu Gln Lys Pro Phe Lys Ala
                500                 505                 510

Gln Tyr Met Leu Val Val His Met Arg Arg His Thr Gly Glu Lys Pro
            515                 520                 525

His Lys Cys Thr Phe Glu Gly Cys Thr Lys Ala Tyr Ser Arg Leu Glu
        530                 535                 540

Asn Leu Lys Thr His Leu Arg Ser His Thr Gly Glu Lys Pro Tyr Val
545                 550                 555                 560

Cys Glu His Glu Gly Cys Asn Lys Ala Phe Ser Asn Ala Ser Asp Arg
                565                 570                 575

Ala Lys His Gln Asn Arg Thr His Ser Asn Glu Lys Pro Tyr Val Cys
                580                 585                 590

Lys Ile Pro Gly Cys Thr Lys Arg Tyr Thr Asp Pro Ser Ser Leu Arg
            595                 600                 605

Lys His Val Lys Thr Val His Gly Pro Glu Ala His Val Thr Lys Lys
        610                 615                 620
```

```
Gln Arg Gly Asp Ile His Pro Arg Pro Pro Pro Arg Asp Ser Gly
625                 630                 635                 640

Ser His Ser Gln Ser Arg Ser Pro Gly Arg Pro Thr Gln Gly Ala Leu
            645                 650                 655

Gly Glu Gln Gln Asp Leu Ser Asn Thr Thr Ser Lys Arg Glu Glu Cys
            660                 665                 670

Leu Gln Val Lys Thr Val Lys Ala Glu Lys Pro Met Thr Ser Gln Pro
            675                 680                 685

Ser Pro Gly Gly Gln Ser Ser Cys Ser Ser Gln Gln Ser Pro Ile Ser
690                 695                 700

Asn Tyr Ser Asn Ser Gly Leu Glu Leu Pro Leu Thr Asp Gly Gly Ser
705                 710                 715                 720

Ile Gly Asp Leu Ser Ala Ile Asp Glu Thr Pro Ile Met Asp Ser Thr
                725                 730                 735

Ile Ser Thr Ala Thr Thr Ala Leu Ala Leu Gln Ala Arg Arg Asn Pro
                740                 745                 750

Ala Gly Thr Lys Trp Met Glu His Val Lys Leu Glu Arg Leu Lys Gln
            755                 760                 765

Val Asn Gly Met Phe Pro Arg Leu Asn Pro Ile Leu Pro Pro Lys Ala
770                 775                 780

Pro Ala Val Ser Pro Leu Ile Gly Asn Gly Thr Gln Ser Asn Asn Thr
785                 790                 795                 800

Cys Ser Leu Gly Gly Pro Met Thr Leu Leu Pro Gly Arg Ser Asp Leu
                805                 810                 815

Ser Gly Val Asp Val Thr Met Leu Asn Met Leu Asn Arg Arg Asp Ser
                820                 825                 830

Ser Ala Ser Thr Ile Ser Ser Ala Tyr Leu Ser Ser Arg Arg Ser Ser
            835                 840                 845

Gly Ile Ser Pro Cys Phe Ser Ser Arg Arg Ser Ser Glu Ala Ser Gln
850                 855                 860

Ala Glu Gly Arg Pro Gln Asn Val Ser Val Ala Asp Ser Tyr Asp Pro
865                 870                 875                 880

Ile Ser Thr Asp Ala Ser Arg Arg Ser Ser Glu Ala Ser Gln Ser Asp
                885                 890                 895

Gly Leu Pro Ser Leu Leu Ser Leu Thr Pro Ala Gln Gln Tyr Arg Leu
            900                 905                 910

Lys Ala Lys Tyr Ala Ala Ala Thr Gly Gly Pro Pro Pro Thr Pro Leu
            915                 920                 925

Pro Asn Met Glu Arg Met Ser Leu Lys Thr Arg Leu Ala Leu Leu Gly
930                 935                 940

Asp Ala Leu Glu Pro Gly Val Ala Leu Pro Pro Val His Ala Pro Arg
945                 950                 955                 960

Arg Cys Ser Asp Gly Gly Ala His Gly Tyr Gly Arg Arg His Leu Gln
                965                 970                 975

Pro His Asp Ala Leu Gly His Gly Val Arg Arg Ala Ser Asp Pro Val
            980                 985                 990

Arg Thr Gly Ser Glu Gly Leu Ala Leu Pro Arg Val Pro Arg Phe Ser
            995                 1000                1005

Ser Leu Ser Ser Cys Asn Pro Pro Ala Met Ala Thr Ser Ala Glu
    1010                1015                1020

Lys Arg Ser Leu Val Leu Gln Asn Tyr Thr Arg Pro Glu Gly Gly
    1025                1030                1035

Gln Ser Arg Asn Phe His Ser Ser Pro Cys Pro Pro Ser Ile Thr
```

|   |   |   |   |   |   |   |   |   |   |
|---|---|---|---|---|---|---|---|---|---|
|   |   | 1040 |   |   | 1045 |   |   | 1050 |   |
| Glu | Asn | Val | Thr | Leu | Glu | Ser | Leu | Thr | Met | Asp | Ala | Asp | Ala | Asn |
|   | 1055 |   |   |   | 1060 |   |   |   | 1065 |
| Leu | Asn | Asp | Glu | Asp | Phe | Leu | Pro | Asp | Asp | Val | Val | Gln | Tyr | Leu |
|   | 1070 |   |   |   | 1075 |   |   |   | 1080 |
| Asn | Ser | Gln | Asn | Gln | Ala | Gly | Tyr | Glu | Gln | His | Phe | Pro | Ser | Ala |
|   | 1085 |   |   |   | 1090 |   |   |   | 1095 |
| Leu | Pro | Asp | Asp | Ser | Lys | Val | Pro | His | Gly | Pro | Gly | Asp | Phe | Asp |
|   | 1100 |   |   |   | 1105 |   |   |   | 1110 |
| Ala | Pro | Gly | Leu | Pro | Asp | Ser | His | Ala | Gly | Gln | Gln | Phe | His | Ala |
|   | 1115 |   |   |   | 1120 |   |   |   | 1125 |
| Leu | Glu | Gln | Pro | Cys | Pro | Glu | Gly | Ser | Lys | Thr | Asp | Leu | Pro | Ile |
|   | 1130 |   |   |   | 1135 |   |   |   | 1140 |
| Gln | Trp | Asn | Glu | Val | Ser | Ser | Gly | Ser | Ala | Asp | Leu | Ser | Ser | Ser |
|   | 1145 |   |   |   | 1150 |   |   |   | 1155 |
| Lys | Leu | Lys | Cys | Gly | Pro | Arg | Pro | Ala | Val | Pro | Gln | Thr | Arg | Ala |
|   | 1160 |   |   |   | 1165 |   |   |   | 1170 |
| Phe | Gly | Phe | Cys | Asn | Gly | Met | Val | Val | His | Pro | Gln | Asn | Pro | Leu |
|   | 1175 |   |   |   | 1180 |   |   |   | 1185 |
| Arg | Ser | Gly | Pro | Ala | Gly | Gly | Tyr | Gln | Thr | Leu | Gly | Glu | Asn | Ser |
|   | 1190 |   |   |   | 1195 |   |   |   | 1200 |
| Asn | Pro | Tyr | Gly | Gly | Pro | Glu | His | Leu | Met | Leu | His | Asn | Ser | Pro |
|   | 1205 |   |   |   | 1210 |   |   |   | 1215 |
| Gly | Ser | Gly | Thr | Ser | Gly | Asn | Ala | Phe | His | Glu | Gln | Pro | Cys | Lys |
|   | 1220 |   |   |   | 1225 |   |   |   | 1230 |
| Ala | Pro | Gln | Tyr | Gly | Asn | Cys | Leu | Asn | Arg | Gln | Pro | Val | Ala | Pro |
|   | 1235 |   |   |   | 1240 |   |   |   | 1245 |
| Gly | Ala | Leu | Asp | Gly | Ala | Cys | Gly | Ala | Gly | Ile | Gln | Ala | Ser | Lys |
|   | 1250 |   |   |   | 1255 |   |   |   | 1260 |
| Leu | Lys | Ser | Thr | Pro | Met | Gln | Gly | Ser | Gly | Gln | Leu | Asn | Phe |
|   | 1265 |   |   |   | 1270 |   |   |   | 1275 |
| Gly | Leu | Pro | Val | Ala | Pro | Asn | Glu | Ser | Ala | Gly | Ser | Met | Val | Asn |
|   | 1280 |   |   |   | 1285 |   |   |   | 1290 |
| Gly | Met | Gln | Asn | Gln | Asp | Pro | Val | Gly | Gln | Gly | Tyr | Leu | Ala | His |
|   | 1295 |   |   |   | 1300 |   |   |   | 1305 |
| Gln | Leu | Leu | Gly | Asp | Ser | Met | Gln | His | Pro | Gly | Ala | Gly | Arg | Pro |
|   | 1310 |   |   |   | 1315 |   |   |   | 1320 |
| Gly | Gln | Gln | Met | Leu | Gly | Gln | Ile | Ser | Ala | Thr | Ser | His | Ile | Asn |
|   | 1325 |   |   |   | 1330 |   |   |   | 1335 |
| Ile | Tyr | Gln | Gly | Pro | Glu | Ser | Cys | Leu | Pro | Gly | Ala | His | Gly | Met |
|   | 1340 |   |   |   | 1345 |   |   |   | 1350 |
| Gly | Ser | Gln | Pro | Ser | Ser | Leu | Ala | Val | Val | Arg | Gly | Tyr | Gln | Pro |
|   | 1355 |   |   |   | 1360 |   |   |   | 1365 |
| Cys | Ala | Ser | Phe | Gly | Gly | Ser | Arg | Arg | Gln | Ala | Met | Pro | Arg | Asp |
|   | 1370 |   |   |   | 1375 |   |   |   | 1380 |
| Ser | Leu | Ala | Leu | Gln | Ser | Gly | Gln | Leu | Ser | Asp | Thr | Ser | Gln | Thr |
|   | 1385 |   |   |   | 1390 |   |   |   | 1395 |
| Cys | Arg | Val | Asn | Gly | Ile | Lys | Met | Glu | Met | Lys | Gly | Gln | Pro | His |
|   | 1400 |   |   |   | 1405 |   |   |   | 1410 |
| Pro | Leu | Cys | Ser | Asn | Leu | Gln | Asn | Tyr | Ser | Gly | Gln | Phe | Tyr | Asp |
|   | 1415 |   |   |   | 1420 |   |   |   | 1425 |
| Gln | Thr | Val | Gly | Phe | Ser | Gln | Gln | Asp | Thr | Lys | Ala | Gly | Ser | Phe |
|   | 1430 |   |   |   | 1435 |   |   |   | 1440 |

```
Ser Ile Ser Asp Ala Ser Cys Leu Leu Gln Gly Thr Ser Ala Lys
        1445                1450                1455

Asn Ser Glu Leu Leu Ser Pro Gly Ala Asn Gln Val Thr Ser Thr
1460                1465                1470

Val Asp Ser Leu Asp Ser His Asp Leu Glu Gly Val Gln Ile Asp
1475                1480                1485

Phe Asp Ala Ile Ile Asp Gly Asp His Ser Ser Leu Met Ser
1490                1495                1500

Gly Ala Leu Ser Pro Ser Ile Ile Gln Asn Leu Ser His Ser Ser
1505                1510                1515

Ser Arg Leu Thr Thr Pro Arg Ala Ser Leu Pro Phe Pro Val Ala
1520                1525                1530

Val His Glu His His Gln His Gly Tyr Arg Gly His Glu Phe Phe
1535                1540                1545

Ala Asp Leu Pro Ser Gly Arg Lys Gln Ile Pro Cys Ser Tyr Ala
1550                1555                1560

Ile Gly Phe Arg Lys Lys Arg Leu Gln Pro Thr Glu Ile Asn Arg
1565                1570                1575

Ser

<210> SEQ ID NO 8
<211> LENGTH: 58
<212> TYPE: PRT
<213> ORGANISM: Homo sapiens

<400> SEQUENCE: 8

Thr Met Thr Ser Ala Glu Lys Val Leu Cys Gln Phe Cys Asp Gln Asp
1               5                   10                  15

Pro Ala Gln Asp Ala Val Lys Thr Cys Val Thr Cys Glu Val Ser Tyr
            20                  25                  30

Cys Asp Glu Cys Leu Lys Ala Thr His Pro Asn Lys Lys Pro Phe Thr
        35                  40                  45

Gly His Arg Leu Ile Glu Pro Ile Pro Asp
    50                  55

<210> SEQ ID NO 9
<211> LENGTH: 339
<212> TYPE: PRT
<213> ORGANISM: Homo sapiens

<400> SEQUENCE: 9

Met Ala Ala Glu Asp Glu Leu Gln Leu Pro Arg Leu Pro Glu Leu Phe
1               5                   10                  15

Glu Thr Gly Arg Gln Leu Leu Asp Glu Val Glu Val Ala Thr Glu Pro
            20                  25                  30

Ala Gly Ser Arg Ile Val Gln Glu Lys Val Phe Lys Gly Leu Asp Leu
        35                  40                  45

Leu Glu Lys Ala Ala Glu Met Leu Ser Gln Leu Asp Leu Phe Ser Arg
    50                  55                  60

Asn Glu Asp Leu Glu Glu Ile Ala Ser Thr Asp Leu Lys Tyr Leu Leu
65                  70                  75                  80

Val Pro Ala Phe Gln Gly Ala Leu Thr Met Lys Gln Val Asn Pro Ser
                85                  90                  95

Lys Arg Leu Asp His Leu Gln Arg Ala Arg Glu His Phe Ile Asn Tyr
            100                 105                 110

Leu Thr Gln Cys His Cys Tyr His Val Ala Glu Phe Glu Leu Pro Lys
        115                 120                 125
```

```
Thr Met Asn Asn Ser Ala Glu Asn His Thr Ala Asn Ser Ser Met Ala
    130                 135                 140

Tyr Pro Ser Leu Val Ala Met Ala Ser Gln Arg Gln Ala Lys Ile Gln
145                 150                 155                 160

Arg Tyr Lys Gln Lys Glu Leu Glu His Arg Leu Ser Ala Met Lys
                165                 170                 175

Ser Ala Val Glu Ser Gly Gln Ala Asp Asp Glu Arg Val Arg Glu Tyr
            180                 185                 190

Tyr Leu Leu His Leu Gln Arg Trp Ile Asp Ile Ser Leu Glu Glu Ile
        195                 200                 205

Glu Ser Ile Asp Gln Glu Ile Lys Ile Leu Arg Glu Arg Asp Ser Ser
    210                 215                 220

Arg Glu Ala Ser Thr Ser Asn Ser Ser Arg Gln Glu Arg Pro Pro Val
225                 230                 235                 240

Lys Pro Phe Ile Leu Thr Arg Asn Met Ala Gln Ala Lys Val Phe Gly
                245                 250                 255

Ala Gly Tyr Pro Ser Leu Pro Thr Met Thr Val Ser Asp Trp Tyr Glu
            260                 265                 270

Gln His Arg Lys Tyr Gly Ala Leu Pro Asp Gln Gly Ile Ala Lys Ala
        275                 280                 285

Ala Pro Glu Glu Phe Arg Lys Ala Ala Gln Gln Glu Glu Gln Glu
    290                 295                 300

Glu Lys Glu Glu Glu Asp Asp Glu Gln Thr Leu His Arg Ala Arg Glu
305                 310                 315                 320

Trp Asp Asp Trp Lys Asp Thr His Pro Arg Gly Tyr Gly Asn Arg Gln
                325                 330                 335

Asn Met Gly

<210> SEQ ID NO 10
<211> LENGTH: 168
<212> TYPE: PRT
<213> ORGANISM: Homo Sapiens

<400> SEQUENCE: 10

Leu Ser Ala Met Lys Ser Ala Val Glu Ser Gly Gln Ala Asp Asp Glu
1               5                   10                  15

Arg Val Arg Glu Tyr Tyr Leu Leu His Leu Gln Arg Trp Ile Asp Ile
                20                  25                  30

Ser Leu Glu Glu Ile Glu Ser Ile Asp Gln Glu Ile Lys Ile Leu Arg
            35                  40                  45

Glu Arg Asp Ser Ser Arg Glu Ala Ser Thr Ser Asn Ser Ser Arg Gln
        50                  55                  60

Glu Arg Pro Pro Val Lys Pro Phe Ile Leu Thr Arg Asn Met Ala Gln
65                  70                  75                  80

Ala Lys Val Phe Gly Ala Gly Tyr Pro Ser Leu Pro Thr Met Thr Val
                85                  90                  95

Ser Asp Trp Tyr Glu Gln His Arg Lys Tyr Gly Ala Leu Pro Asp Gln
            100                 105                 110

Gly Ile Ala Lys Ala Ala Pro Glu Glu Phe Arg Lys Ala Ala Gln Gln
        115                 120                 125

Gln Glu Glu Gln Glu Glu Lys Glu Glu Glu Asp Asp Glu Gln Thr Leu
    130                 135                 140

His Arg Ala Arg Glu Trp Asp Asp Trp Lys Asp Thr His Pro Arg Gly
145                 150                 155                 160
```

Tyr Gly Asn Arg Gln Asn Met Gly
                165

<210> SEQ ID NO 11
<211> LENGTH: 290
<212> TYPE: PRT
<213> ORGANISM: Homo Sapiens

<400> SEQUENCE: 11

Met Ala Ala Glu Asp Glu Leu Gln Leu Pro Arg Leu Pro Glu Leu Phe
1               5                   10                  15

Glu Thr Gly Arg Gln Leu Leu Asp Val Glu Val Ala Thr Glu Pro
            20                  25                  30

Ala Gly Ser Arg Ile Val Gln Glu Lys Val Phe Lys Gly Leu Asp Leu
        35                  40                  45

Leu Glu Lys Ala Ala Glu Met Leu Ser Gln Leu Asp Leu Phe Ser Arg
    50                  55                  60

Asn Glu Asp Leu Glu Glu Ile Ala Ser Thr Asp Leu Lys Tyr Leu Leu
65                  70                  75                  80

Val Pro Ala Phe Gln Gly Ala Leu Thr Met Lys Gln Val Asn Pro Ser
                85                  90                  95

Lys Arg Leu Asp His Leu Gln Arg Ala Arg Glu His Phe Ile Asn Tyr
            100                 105                 110

Leu Thr Gln Cys His Cys Tyr His Val Ala Glu Phe Glu Leu Pro Lys
        115                 120                 125

Thr Met Asn Asn Ser Ala Glu Asn His Thr Ala Asn Ser Ser Met Ala
    130                 135                 140

Tyr Pro Ser Leu Val Ala Met Ala Ser Gln Arg Gln Ala Lys Ile Gln
145                 150                 155                 160

Arg Tyr Lys Gln Lys Lys Glu Leu Glu His Arg Leu Ser Ala Met Lys
                165                 170                 175

Ser Ala Val Glu Ser Gly Gln Ala Asp Asp Gly Arg Val Arg Glu Tyr
            180                 185                 190

Tyr Leu Leu His Leu Gln Arg Trp Ile Asp Ile Ser Leu Glu Glu Ile
        195                 200                 205

Glu Ser Ile Asp Gln Glu Ile Lys Ile Leu Arg Glu Arg Asp Ser Ser
    210                 215                 220

Arg Glu Ala Ser Thr Ser Asn Ser Ser Arg Gln Glu Arg Pro Pro Val
225                 230                 235                 240

Lys Pro Phe Ile Leu Thr Arg Asn Met Ala Gln Ala Lys Val Phe Gly
                245                 250                 255

Ala Gly Tyr Pro Ser Leu Pro Thr Met Thr Val Ser Asp Trp Tyr Glu
            260                 265                 270

Gln His Arg Lys Tyr Gly Ala Leu Pro Asp Gln Gly Ile Ala Lys Ala
        275                 280                 285

Ala Pro
290

<210> SEQ ID NO 12
<211> LENGTH: 379
<212> TYPE: PRT
<213> ORGANISM: Homo Sapiens

<400> SEQUENCE: 12

Met Glu Thr Leu Glu Ser Glu Leu Thr Cys Pro Ile Cys Leu Glu Leu
1               5                   10                  15

Phe Glu Asp Pro Leu Leu Leu Pro Cys Ala His Ser Leu Cys Phe Asn

```
                20                  25                  30
Cys Ala His Arg Ile Leu Val Ser His Cys Thr Asn Glu Ser Val
         35                  40                  45

Glu Ser Ile Thr Ala Phe Gln Cys Pro Thr Cys Arg His Val Ile Thr
     50                  55                  60

Leu Ser Gln Arg Gly Leu Asp Gly Leu Lys Arg Asn Val Thr Leu Gln
65                  70                  75                  80

Asn Ile Ile Asp Arg Phe Gln Lys Ala Ser Val Ser Gly Pro Asn Ser
                85                  90                  95

Pro Ser Glu Thr Arg Arg Glu Arg Ala Phe Asp Ala Asn Thr Met Thr
            100                 105                 110

Ser Ala Glu Lys Val Leu Cys Gln Phe Cys Asp Gln Asp Pro Ala Gln
        115                 120                 125

Asp Ala Val Lys Thr Cys Val Thr Cys Glu Val Ser Tyr Cys Asp Glu
    130                 135                 140

Cys Leu Lys Ala Thr His Pro Asn Lys Lys Pro Phe Thr Gly His Arg
145                 150                 155                 160

Leu Ile Glu Pro Ile Pro Asp Ser His Ile Arg Gly Leu Met Cys Leu
                165                 170                 175

Glu His Glu Asp Glu Lys Val Asn Met Tyr Cys Val Thr Asp Asp Gln
            180                 185                 190

Leu Ile Cys Ala Leu Cys Lys Leu Val Gly Arg His Arg Asp His Gln
        195                 200                 205

Val Ala Ala Leu Ser Glu Arg Tyr Asp Lys Leu Lys Gln Asn Leu Glu
    210                 215                 220

Ser Asn Leu Thr Asn Leu Ile Lys Arg Asn Thr Glu Leu Glu Thr Leu
225                 230                 235                 240

Leu Ala Lys Leu Ile Gln Thr Cys Gln His Val Glu Val Asn Ala Ser
                245                 250                 255

Arg Gln Glu Ala Lys Leu Thr Glu Glu Cys Asp Leu Leu Ile Glu Ile
            260                 265                 270

Ile Gln Gln Arg Arg Gln Ile Ile Gly Thr Lys Ile Lys Glu Gly Lys
        275                 280                 285

Val Met Arg Leu Arg Lys Leu Ala Gln Gln Ile Ala Asn Cys Lys Gln
    290                 295                 300

Cys Ile Glu Arg Ser Ala Ser Leu Ile Ser Gln Ala Glu His Ser Leu
305                 310                 315                 320

Lys Glu Asn Asp His Ala Arg Phe Leu Gln Thr Ala Lys Asn Ile Thr
                325                 330                 335

Glu Arg Val Ser Met Ala Thr Ala Ser Ser Gln Val Leu Ile Pro Glu
            340                 345                 350

Ile Asn Leu Asn Asp Thr Phe Asp Thr Phe Ala Leu Asp Phe Ser Arg
        355                 360                 365

Glu Lys Lys Leu Leu Glu Cys Leu Asp Tyr Leu
    370                 375

<210> SEQ ID NO 13
<211> LENGTH: 149
<212> TYPE: PRT
<213> ORGANISM: Homo Sapiens

<400> SEQUENCE: 13

Leu Ser Gln Arg Gly Leu Asp Gly Leu Lys Arg Asn Val Thr Leu Gln
1               5                  10                  15

Asn Ile Ile Asp Arg Phe Gln Lys Ala Ser Val Ser Gly Pro Asn Ser
```

```
                    20                  25                  30
Pro Ser Glu Thr Arg Arg Glu Arg Ala Phe Asp Ala Asn Thr Met Thr
                35                  40                  45
Ser Ala Glu Lys Val Leu Cys Gln Phe Cys Asp Gln Asp Pro Ala Gln
         50                  55                  60
Asp Ala Val Lys Thr Cys Val Thr Cys Glu Val Ser Tyr Cys Asp Glu
 65                  70                  75                  80
Cys Leu Lys Ala Thr His Pro Asn Lys Lys Pro Phe Thr Gly His Arg
                 85                  90                  95
Leu Ile Glu Pro Ile Pro Asp Ser His Ile Arg Gly Leu Met Cys Leu
                100                 105                 110
Glu His Glu Asp Glu Lys Val Asn Met Tyr Cys Val Thr Asp Asp Gln
            115                 120                 125
Leu Ile Cys Ala Leu Cys Lys Leu Val Gly Arg His Arg Asp His Gln
    130                 135                 140
Val Ala Ala Leu Ser
145

<210> SEQ ID NO 14
<211> LENGTH: 101
<212> TYPE: PRT
<213> ORGANISM: Homo Sapiens

<400> SEQUENCE: 14

Leu Ser Gln Arg Gly Leu Asp Gly Leu Lys Arg Asn Val Thr Leu Gln
 1               5                  10                  15
Asn Ile Ile Asp Arg Phe Gln Lys Ala Ser Val Ser Gly Pro Asn Ser
                20                  25                  30
Pro Ser Glu Thr Arg Arg Glu Arg Ala Phe Asp Ala Asn Thr Met Thr
             35                  40                  45
Ser Ala Glu Lys Val Leu Cys Gln Phe Cys Asp Gln Asp Pro Ala Gln
         50                  55                  60
Asp Ala Val Lys Thr Cys Val Thr Cys Glu Val Ser Tyr Cys Asp Glu
 65                  70                  75                  80
Cys Leu Lys Ala Thr His Pro Asn Lys Lys Pro Phe Thr Gly His Arg
                 85                  90                  95
Leu Ile Glu Pro Ile
                100

<210> SEQ ID NO 15
<211> LENGTH: 56
<212> TYPE: PRT
<213> ORGANISM: Homo Sapiens

<400> SEQUENCE: 15

Thr Met Thr Ser Ala Glu Lys Val Leu Cys Gln Phe Cys Asp Gln Asp
 1               5                  10                  15
Pro Ala Gln Asp Ala Val Lys Thr Cys Val Thr Cys Glu Val Ser Tyr
                20                  25                  30
Cys Asp Glu Cys Leu Lys Ala Thr His Pro Asn Lys Lys Pro Phe Thr
             35                  40                  45
Gly His Arg Leu Ile Glu Pro Ile
         50                  55

<210> SEQ ID NO 16
<211> LENGTH: 113
<212> TYPE: PRT
<213> ORGANISM: Homo Sapiens
```

<400> SEQUENCE: 16

Met Glu Thr Leu Glu Ser Glu Leu Thr Cys Pro Ile Cys Leu Glu Leu
1               5                   10                  15

Phe Glu Asp Pro Leu Leu Leu Pro Cys Ala His Ser Leu Cys Phe Asn
                20                  25                  30

Cys Ala His Arg Ile Leu Val Ser His Cys Ala Thr Asn Glu Ser Val
            35                  40                  45

Glu Ser Ile Thr Ala Phe Gln Cys Pro Thr Cys Arg His Val Ile Thr
    50                  55                  60

Leu Ser Gln Arg Gly Leu Asp Gly Leu Lys Arg Asn Val Thr Leu Gln
65                  70                  75                  80

Asn Ile Ile Asp Arg Phe Gln Lys Ala Ser Val Ser Gly Pro Asn Ser
                85                  90                  95

Pro Ser Glu Thr Arg Arg Glu Arg Ala Phe Asp Ala Asn Thr Met Thr
            100                 105                 110

Ser

<210> SEQ ID NO 17
<211> LENGTH: 185
<212> TYPE: PRT
<213> ORGANISM: Homo Sapiens

<400> SEQUENCE: 17

Cys Ala Leu Cys Lys Leu Val Gly Arg His Arg Asp His Gln Val Ala
1               5                   10                  15

Ala Leu Ser Glu Arg Tyr Asp Lys Leu Lys Gln Asn Leu Glu Ser Asn
                20                  25                  30

Leu Thr Asn Leu Ile Lys Arg Asn Thr Glu Leu Glu Thr Leu Leu Ala
            35                  40                  45

Lys Leu Ile Gln Thr Cys Gln His Val Glu Val Asn Ala Ser Arg Gln
    50                  55                  60

Glu Ala Lys Leu Thr Glu Glu Cys Asp Leu Leu Ile Glu Ile Ile Gln
65                  70                  75                  80

Gln Arg Arg Gln Ile Ile Gly Thr Lys Ile Lys Glu Gly Lys Val Met
                85                  90                  95

Arg Leu Arg Lys Leu Ala Gln Gln Ile Ala Asn Cys Lys Gln Cys Ile
            100                 105                 110

Glu Arg Ser Ala Ser Leu Ile Ser Gln Ala Glu His Ser Leu Lys Glu
    115                 120                 125

Asn Asp His Ala Arg Phe Leu Gln Thr Ala Lys Asn Ile Thr Glu Arg
130                 135                 140

Val Ser Met Ala Thr Ala Ser Ser Gln Val Leu Ile Pro Glu Ile Asn
145                 150                 155                 160

Leu Asn Asp Thr Phe Asp Thr Phe Ala Leu Asp Phe Ser Arg Glu Lys
                165                 170                 175

Lys Leu Leu Glu Cys Leu Asp Tyr Leu
            180                 185

<210> SEQ ID NO 18
<211> LENGTH: 299
<212> TYPE: PRT
<213> ORGANISM: Homo Sapiens

<400> SEQUENCE: 18

Cys Ala Leu Cys Lys Leu Val Gly Arg His Arg Asp His Gln Val Ala
1               5                   10                  15

```
Ala Leu Ser Glu Arg Tyr Asp Lys Leu Lys Gln Asn Leu Glu Ser Asn
             20                  25                  30

Leu Thr Asn Leu Ile Lys Arg Asn Thr Glu Leu Glu Thr Leu Leu Ala
         35                  40                  45

Lys Leu Ile Gln Thr Cys Gln His Val Glu Val Asn Ala Ser Arg Gln
 50                  55                  60

Glu Ala Lys Leu Thr Glu Glu Cys Asp Leu Leu Ile Glu Ile Ile Gln
65                  70                  75                  80

Gln Arg Arg Gln Ile Ile Gly Thr Lys Ile Lys Glu Gly Lys Val Met
                 85                  90                  95

Arg Leu Arg Lys Leu Ala Gln Gln Ile Ala Asn Cys Lys Gln Cys Ile
            100                 105                 110

Glu Arg Ser Ala Ser Leu Ile Ser Gln Ala Glu His Ser Leu Lys Glu
            115                 120                 125

Asn Asp His Ala Arg Phe Leu Gln Thr Ala Lys Asn Ile Thr Glu Arg
130                 135                 140

Val Ser Met Ala Thr Ala Ser Ser Gln Val Leu Ile Pro Glu Ile Asn
145                 150                 155                 160

Leu Asn Asp Thr Phe Asp Thr Phe Ala Leu Asp Phe Ser Arg Glu Lys
                165                 170                 175

Lys Leu Leu Glu Cys Leu Asp Tyr Leu Thr Ala Pro Asn Pro Pro Thr
            180                 185                 190

Ile Arg Glu Glu Leu Cys Thr Ala Ser Tyr Asp Thr Ile Thr Val His
            195                 200                 205

Trp Thr Ser Asp Asp Glu Phe Ser Val Val Ser Tyr Glu Leu Gln Tyr
210                 215                 220

Thr Ile Phe Thr Gly Gln Ala Asn Val Val Ser Leu Cys Asn Ser Ala
225                 230                 235                 240

Asp Ser Trp Met Ile Val Pro Asn Ile Lys Gln Asn His Tyr Thr Val
                245                 250                 255

His Gly Leu Gln Ser Gly Thr Lys Tyr Ile Phe Met Val Lys Ala Ile
            260                 265                 270

Asn Gln Ala Gly Ser Arg Ser Ser Glu Pro Gly Lys Leu Lys Thr Asn
            275                 280                 285

Ser Gln Pro Phe Lys Leu Asp Pro Lys Ser Ala
            290                 295

<210> SEQ ID NO 19
<211> LENGTH: 473
<212> TYPE: PRT
<213> ORGANISM: Homo sapiens

<400> SEQUENCE: 19

Cys Ala Leu Cys Lys Leu Val Gly Arg His Arg Asp His Gln Val Ala
1                5                  10                  15

Ala Leu Ser Glu Arg Tyr Asp Lys Leu Lys Gln Asn Leu Glu Ser Asn
             20                  25                  30

Leu Thr Asn Leu Ile Lys Arg Asn Thr Glu Leu Glu Thr Leu Leu Ala
         35                  40                  45

Lys Leu Ile Gln Thr Cys Gln His Val Glu Val Asn Ala Ser Arg Gln
 50                  55                  60

Glu Ala Lys Leu Thr Glu Glu Cys Asp Leu Leu Ile Glu Ile Ile Gln
65                  70                  75                  80

Gln Arg Arg Gln Ile Ile Gly Thr Lys Ile Lys Glu Gly Lys Val Met
                 85                  90                  95
```

```
Arg Leu Arg Lys Leu Ala Gln Gln Ile Ala Asn Cys Lys Gln Cys Ile
            100                 105                 110

Glu Arg Ser Ala Ser Leu Ile Ser Gln Ala Glu His Ser Leu Lys Glu
            115                 120                 125

Asn Asp His Ala Arg Phe Leu Gln Thr Ala Lys Asn Ile Thr Glu Arg
130                 135                 140

Val Ser Met Ala Thr Ala Ser Ser Gln Val Leu Ile Pro Glu Ile Asn
145                 150                 155                 160

Leu Asn Asp Thr Phe Asp Thr Phe Ala Leu Asp Phe Ser Arg Glu Lys
                165                 170                 175

Lys Leu Leu Glu Cys Leu Asp Tyr Leu Thr Ala Pro Asn Pro Pro Thr
            180                 185                 190

Ile Arg Glu Glu Leu Cys Thr Ala Ser Tyr Asp Thr Ile Thr Val His
            195                 200                 205

Trp Thr Ser Asp Asp Glu Phe Ser Val Val Ser Tyr Glu Leu Gln Tyr
210                 215                 220

Thr Ile Phe Thr Gly Gln Ala Asn Val Val Ser Leu Cys Asn Ser Ala
225                 230                 235                 240

Asp Ser Trp Met Ile Val Pro Asn Ile Lys Gln Asn His Tyr Thr Val
                245                 250                 255

His Gly Leu Gln Ser Gly Thr Lys Tyr Ile Phe Met Val Lys Ala Ile
            260                 265                 270

Asn Gln Ala Gly Ser Arg Ser Ser Glu Pro Gly Lys Leu Lys Thr Asn
            275                 280                 285

Ser Gln Pro Phe Lys Leu Asp Pro Lys Ser Ala His Arg Lys Leu Lys
290                 295                 300

Val Ser His Asp Asn Leu Thr Val Glu Arg Asp Glu Ser Ser Ser Lys
305                 310                 315                 320

Lys Ser His Thr Pro Glu Arg Phe Thr Ser Gln Gly Ser Tyr Gly Val
                325                 330                 335

Ala Gly Asn Val Phe Ile Asp Ser Gly Arg His Tyr Trp Glu Val Val
            340                 345                 350

Ile Ser Gly Ser Thr Trp Tyr Ala Ile Gly Leu Ala Tyr Lys Ser Ala
            355                 360                 365

Pro Lys His Glu Trp Ile Gly Lys Asn Ser Ala Ser Trp Ala Leu Cys
370                 375                 380

Arg Cys Asn Asn Asn Trp Val Val Arg His Asn Ser Lys Glu Ile Pro
385                 390                 395                 400

Ile Glu Pro Ala Pro His Leu Arg Arg Val Gly Ile Leu Leu Asp Tyr
                405                 410                 415

Asp Asn Gly Ser Ile Ala Phe Tyr Asp Ala Leu Asn Ser Ile His Leu
            420                 425                 430

Tyr Thr Phe Asp Val Ala Phe Ala Gln Pro Val Cys Pro Thr Phe Thr
            435                 440                 445

Val Trp Asn Lys Cys Leu Thr Ile Ile Thr Gly Leu Pro Ile Pro Asp
450                 455                 460

His Leu Asp Cys Thr Glu Gln Leu Pro
465                 470
```

<210> SEQ ID NO 20
<211> LENGTH: 196
<212> TYPE: PRT
<213> ORGANISM: Homo sapiens

<400> SEQUENCE: 20

```
Arg Ser Ser Glu Pro Gly Lys Leu Lys Thr Asn Ser Gln Pro Phe Lys
1               5                   10                  15

Leu Asp Pro Lys Ser Ala His Arg Lys Leu Lys Val Ser His Asp Asn
            20                  25                  30

Leu Thr Val Glu Arg Asp Glu Ser Ser Lys Lys Ser His Thr Pro
        35                  40                  45

Glu Arg Phe Thr Ser Gln Gly Ser Tyr Gly Val Ala Gly Asn Val Phe
    50                  55                  60

Ile Asp Ser Gly Arg His Tyr Trp Glu Val Val Ile Ser Gly Ser Thr
65                  70                  75                  80

Trp Tyr Ala Ile Gly Leu Ala Tyr Lys Ser Ala Pro Lys His Glu Trp
                85                  90                  95

Ile Gly Lys Asn Ser Ala Ser Trp Ala Leu Cys Arg Cys Asn Asn Asn
                100                 105                 110

Trp Val Val Arg His Asn Ser Lys Glu Ile Pro Ile Glu Pro Ala Pro
            115                 120                 125

His Leu Arg Arg Val Gly Ile Leu Leu Asp Tyr Asp Asn Gly Ser Ile
    130                 135                 140

Ala Phe Tyr Asp Ala Leu Asn Ser Ile His Leu Tyr Thr Phe Asp Val
145                 150                 155                 160

Ala Phe Ala Gln Pro Val Cys Pro Thr Phe Thr Val Trp Asn Lys Cys
                165                 170                 175

Leu Thr Ile Ile Thr Gly Leu Pro Ile Pro Asp His Leu Asp Cys Thr
                180                 185                 190

Glu Gln Leu Pro
        195

<210> SEQ ID NO 21
<211> LENGTH: 35
<212> TYPE: DNA
<213> ORGANISM: Homo sapiens

<400> SEQUENCE: 21
tcgaattcgc aatggccaac accatgacct ccgcc                              35

<210> SEQ ID NO 22
<211> LENGTH: 34
<212> TYPE: DNA
<213> ORGANISM: Homo sapiens

<400> SEQUENCE: 22
ggtagcagac taactcggtt aaactcagct gcca                               34

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: Description of artificial sequence: synthetic
      oligonucleotide
<220> FEATURE:
<221> NAME/KEY: misc_feature
<222> LOCATION: (20)..(21)
<223> OTHER INFORMATION: n=combined DNA/RNA sequence

<400> SEQUENCE: 23
guaccuuuug gugccagcgn n                                             21

<210> SEQ ID NO 24
```

```
<211> LENGTH: 21
<212> TYPE: DNA
<213> ORGANISM: Artificial Sequence
<220> FEATURE:
<221> NAME/KEY: source
<223> OTHER INFORMATION: Description of artificial sequence: synthetic
      oligonucleotide
<220> FEATURE:
<221> NAME/KEY: misc_feature
<222> LOCATION: (20)..(21)
<223> OTHER INFORMATION: n=combined DNA/RNA sequence

<400> SEQUENCE: 24
cgcuggcacc aaaagguacn n                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: Description of artificial sequence: synthetic
      oligonucleotide
<220> FEATURE:
<221> NAME/KEY: misc_feature
<222> LOCATION: (20)..(21)
<223> OTHER INFORMATION: n=combined DNA/RNA sequence

<400> SEQUENCE: 25
uucuccgaac gugucacgun n                                              21

<210> SEQ ID NO 26
<211> LENGTH: 21
<212> TYPE: RNA
<213> ORGANISM: Artificial Sequence
<220> FEATURE:
<221> NAME/KEY: source
<223> OTHER INFORMATION: Description of artificial sequence: synthetic
      oligonucleotide
<220> FEATURE:
<221> NAME/KEY: misc_feature
<222> LOCATION: (20)..(21)
<223> OTHER INFORMATION: n=combined DNA/RNA sequence

<400> SEQUENCE: 26
acgugacacg uucggagaan n                                              21
```